US006369098B1

(12) United States Patent
Pershadsingh et al.

(10) Patent No.: US 6,369,098 B1
(45) Date of Patent: Apr. 9, 2002

(54) DITHIOLANE DERIVATIVES

(75) Inventors: Harrihar A. Pershadsingh, Bakersfield, CA (US); Mitchell A. Avery, Oxford, MS (US)

(73) Assignee: Bethesda Pharmaceuticals, Inc., Bakersfield, CA (US)

( * ) Notice: Subject to any disclaimer, the term of this patent is extended or adjusted under 35 U.S.C. 154(b) by 0 days.

(21) Appl. No.: 09/684,738

(22) Filed: Oct. 4, 2000

Related U.S. Application Data

(60) Provisional application No. 60/157,890, filed on Oct. 5, 1999, provisional application No. 60/185,347, filed on Feb. 26, 2000, and provisional application No. 60/225,907, filed on Aug. 17, 2000.

(51) Int. Cl.$^7$ ..................... A61K 31/385; C07D 339/02
(52) U.S. Cl. ..................... 514/440; 549/32; 549/35; 549/39
(58) Field of Search ..................... 514/440; 549/35, 549/39, 32

(56) References Cited

U.S. PATENT DOCUMENTS

| | | | |
|---|---|---|---|
| 5,925,668 A | 7/1999 | Biewenga et al. | 514/440 |
| 6,013,663 A | 1/2000 | Fujita et al. | 514/440 |
| 6,046,228 A | 4/2000 | Rice et al. | 514/441 |
| 6,090,842 A | 7/2000 | Packer et al. | 514/440 |
| 6,127,394 A * | 10/2000 | Pershadsingh et al. | 514/369 |
| 6,204,288 B1 * | 3/2001 | Pershadsingh et al. | 514/440 |
| 6,288,106 B1 * | 9/2001 | Pearson et al. | 514/440 |

FOREIGN PATENT DOCUMENTS

| | | |
|---|---|---|
| WO | WO00/53601 | 9/2000 |

OTHER PUBLICATIONS

Yanagisawa, H. et al., "Novel Oximes Having 5–Benzyl–2, 4–thiazolidinedione as Antihyperglycemic Agents: Synthesis and Structure—Activity Relationship," *Bioorganic & Medicinal Chemistry Letters*, 10:373–375 (2000).

Nomura, M. et al., "(3–Substituted Benzyl)thiazolidine–2, 4–diones as Structurally New Antihyperglycemic Agents," *Bioorganic & Medicinal Chemistry Letters*, 9:533–538 (1999).

Prabhakar, C. et al., "Synthesis and Biological Activity of Novel Thiazolidinediones," *Bioorganic & Medicinal Chemistry Letters*, 8:2725–2730 (1998).

Murakami, K. et al., "Evidence for Direct Binding of Fatty Acids and Eicosanoids to Human Peroxisome Proliferators–Activated Receptor α," *Biochemical and Biophysical Research Communications*, 260:609–613 (1999).

Willson, T. M. et al., "The PPARs: From Orphan Receptors to Drug Discovery," *Journal of Medicinal Chemistry*, 43(4):527–550 (2000).

Shinkai, H. et al., "Isoxazolidine–3,5–dione and Noncyclic 1,3–Dicarbonyl Compounds as Hypoglycemic Agents," *J. Med. Chem.*, 41:1927–1933 (1998).

Schoonjans, K. et al., "Thiazolidinediones: an update," *The Lancet*, 355;1008–1010 (2000).

Pershadsingh, H.A., "Pharmacological peroxisome proliferators–activated receptors–γ ligands: emerging clinical indications beyond diabetes," *Exp. Opin. Invest. Drugs*, 8(11):1–14 (1999).

Haigh, D. et al., "Non–thiazolidinedione Antihyperglycaemic Agents. Part 3: The Effects of Stereochemistry on the Potency of α–Methoxy–β–phenylpropanoic Acids," *Bioorganic & Medicinal Chemistry*, 7:821–830 (1999).

* cited by examiner

*Primary Examiner*—Deborah C. Lambkin
(74) *Attorney, Agent, or Firm*—Townsend and Townsend and Crew LLP

(57) ABSTRACT

The present invention describes methods for synthesizing novel dithiolane derivatives, ligands with high affinity for the nuclear hormone receptors, peroxisome proliferator-activated receptor-γ (PPARγ) and/or PPARα. Methods for using these compounds in the treatment of endocrine, skin, cardiovascular, immunological, neurological, neuropsychiatric, neoplastic and chronic viral diseases of various organs, including the eye are described. Methods of treating proliferative and inflammatory diseases, degenerative diseases, and age-related dysregulations, caused by an hereditary (genetic) condition or an environmental insult are also provided. In addition, methods are provided for treating conditions and diseases comprising the step of administering to a human or an animal in need thereof a therapeutic amount of pharmacological compositions comprising a pharmaceutically acceptable carrier, a PPARα agonist, and a second agent selected from the following: a PPARγ ligand, or an RXR ligand (rexinoid), or a PPARγ/RXR ligand, effective to reverse, slow, stop, or prevent the pathological inflammatory or degenerative process.

42 Claims, 22 Drawing Sheets

R-Lipoic Acid, n = 4, 1
S- Lipoic Acid, n = 4, 2
rac-Lipoic Acid, n = 4, 3
R-Norlipoic Acid, n = 3, 4
S-Norlipoic Acid, n = 3, 5
rac-Norlipoic Acid, n = 3, 6
R-Dinorlipoic Acid, n = 2, 7
S-Dinorlipoic Acid, n = 2, 8
rac-Dinorlipoic Acid, n = 2, 9

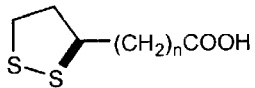

R-Homolipoic Acid, n = 5, 10
S- Homolipoic Acid, n = 5, 11
rac-Homolipoic Acid, n = 5, 12
R-Trinorlipoic Acid, n = 1, 13
S-Trinorlipoic Acid, n = 1, 14
rac-Trinorlipoic Acid, n = 1, 15
R-Tetranorlipoic Acid, n = 0, 16
S-Tetranorlipoic Acid, n = 0, 17
rac-Tetranorlipoic Acid, n = 0, 18

Isohomolipoic Acid, n = 5, 19
Isolipoic Acid, n = 4, 20
Isonorlipoic Acid, n = 3, 21

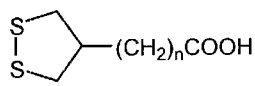

Isodinorlipoic Acid, n = 2, 22
Isotrinorlipoic Acid, n = 1, 23
Isotetranorlipoic Acid, n = 0, 24

*FIG. 1*

Isolipoic Acid, 19-23

DITHIOLANE DERIVATIVES

CROSS-REFERENCES TO RELATED APPLICATIONS

This application claims priority to U.S. patent application Ser. No. 60/157,890, filed Oct. 5, 1999; U.S. patent application Ser. No. 60/185,347, filed Feb. 26, 2000; and U.S. patent application Ser. No. 60/225,907, filed Aug. 17, 2000; the disclosures of which are all incorporated by reference in their entireties for all purposes.

BACKGROUND OF THE INVENTION

The peroxisome proliferator-activated receptors (PPARs) are members of the steroid/thyroid/retinoid nuclear receptor superfamily of ligand-activated transcription factors. Three subtypes of PPARs have been cloned from the mouse and human, i.e., PPARγ and PPARδ. In humans, PPARγ and PPARα are differentially expressed in organs and tissues (see, Willson et al. *J Med. Chem.* 43:527–50 (2000)).

Nuclear receptors like PPAR possess DNA binding domains (DBDs) that recognize specific DNA sequences (called response elements) located in the regulatory regions of their target genes (see, Mangelsdorf, et al. *Cell* 83:835–839 (1995)); Perlmann, et al. *Cell* 90:391–397 (1997)). Activation of PPARs modulates the expression of genes containing the appropriate respective perixosome proliferator response elements (PPRE) in its promoter region.

In the past, the genes regulated by PPARs were believed to be predominantly associated with lipid and glucose metabolism. Thiazolidinediones, which are a class of oral insulin-sensitizing agents that improve glucose utilization without stimulating insulin release, are selective PPAR agonists. U.S. Pat. No. 4,287,200, discloses certain thiazolidine derivatives having the ability to lower blood glucose levels. In addition, U.S. Pat. No. 4,572,912, discloses thiazolindinedione derivatives having the ability to lower blood lipid and blood glucose levels. These compounds were shown to have the ability to decrease the levels of blood lipid peroxides, blood triglycerides and blood cholesterol. A PPARγ antagonist that inhibits adipocyte differentiation has also been synthesized (see, Oberfield, et al., *Proc Natl Acad Sci USA* 96:6102–6 (1999)).

However, recent discoveries suggest that the genes regulated by PPAR receptors also play a role in other processes. Binding of ligands to PPARs induce changes in the transcriptional activity of genes that modulate inflammatory processes, angiogenesis, cellular proliferation and differentiation, apoptosis, and the activities of iNOS, MMPases and TIMPs. These findings suggest that regulation of the action of PPAR may have a therapeutic role in treating diseases such as occlusive vascular diseases (e.g. atherosclerosis), hypertension, neovascular diseases (e.g. diabetic retinopathy), inflammatory diseases (e.g. inflammatory bowel disease and psoriasis), and neoplastic diseases (carcinogenesis).

The precise contribution of each particular PPAR subtype to transcriptional activation of particular genes is difficult to predict. DNA response elements for both PPARα and PPARγ have been found in the promoter regions of a variety of genes, including a number involved in lipid and fatty acid metabolism. For example, in fetal rat brown adipocytes, expression of the uncoupling proteins UCP-1, UCP-2 and UCP-3 is controlled via both PPARα and PPARγ activation. Activation of PPARγ elicited 5- and 3-fold increases in UCP-1 and UCP-3, respectively. In contrast, activation of PPARα increased UCP-1 ten-fold, but decreased UCP-3. Interestingly, when both PPAR and were activated, a synergistic interaction occurred in regulation of UCP-3.

These differential and synergistic effects may be mediated by co-activator recruitment, suppression of co-repressor proteins, or direct interaction at the level of the PPRE (see, Teruel, et al. *Biochem Biophys Res Commun.* 273(2):560–4 (2000)). It is not known whether the nuclear receptor coactivators or corepressors identified to date are selective for particular PPAR receptors (see, Spiegelman, et al., *Diabetes* 47:507–514 (1998)). Many coactivators or corepressors have multiple modes of action and hence it is not clear which cofactors are more important for the function of any particular receptor (see, Puigserver, et al. *Science* 286:1368–1371 (1999). Furthermore, the tremendous specificity of biological actions of the individual nuclear receptors (see, Spiegelman, et al. *Diabetes* 47:507–514 (1998)), strongly suggests that the full spectrum of nuclear cofactors that regulate the transcriptional activity of PPARγ and/or PPARα remains to be defined.

Due to this lack of understanding of PPARγ and PPARα-related activity and mechanisms, as well as the differential expression of PPARγ and PPARα in cells, it is difficult to ascertain the potential effects of concurrent activation of PPAR gamma and alpha receptors on both cellular processes relevant to disease. For example, PPARα or PPARγ may either have similar or disparate effects. It is known that inflammatory activation of human aortic smooth-muscle cells is inhibited by PPARα, but not by PPARγ. Apoptosis in human monocyte-derived macrophages is induced by activation of either PPARα and PPARγ (see, Staels et al. *Nature* 393:790–3 (1998)); Chinetti, et al. *J Biol Chem.* 273:25573–80 (1998)). However, PPARγ activation by troglitazone or 15-deoxy-Δ-12–14-prostaglandin J2 protects cerebellar granule cells from cytokine-induced apoptotic cell death (see, Heneka, et al. *J Neuroimmunol* 100:156–68 (1999)).

To summarize, PPAR subtypes exhibit differential patterns of tissue expression, different actions on different response elements, differential effects on co-activators and co-repressors, and differential regulation of access to the core transcriptional machinery. This complexity of PPAR regulation makes it extremely difficult to predict precisely which genes will ultimately be activated (transcribed) or inactivated (suppressed) as a result of activation by a particular combination of an agonist or an antagonist of PPARγ or PPARα. As a consequence, it is impossible to predict with certainty the way in which a tissue expressing PPARγ and PPARα may respond to a particular ligand, or whether a particular pathological state will be attenuated, arrested, accentuated or worsened by said ligand. This is especially the case in which a single ligand activates both PPARγ and PPARα to similar degrees.

In view of this complex interplay between PPARγ and PPARα, it is desirable to synthesize compounds, which bind both receptors and can take advantage of potential synergistic effects. For example, PPARγ and PPARα activation has been shown to inhibit proliferation (see, Ellis, et al. *Arch Dermatol.* 136:609–616 (2000)) and promote differentiation of epidermal keratinocytes, respectively (see, Komuves et al. *J Invest Dermatol.* 115:353–360 (2000)).

The syntheses of thiazolidine dithiolane derivatives with affinity for PPARγ have been described in WO 00/53601, published Sep. 14, 2000. Despite the advances of WO 00/53601, what is needed in the art are non-thiazolidinedione (non-TZD) dithiolane derivatives with high affinity for PPARγ that function either as PPARγ agonists, PPARγ antagonists, or mixed PPARγ agonist/antagonists. Methods to synthesize these non-TZD compounds with high affinity for both PPARγ and PPARδ, antagonists, mixed (partial) agonist/antagonists, or mixed PPARγ/PPARδ agonists are also needed. The present invention remedies such needs.

SUMMARY OF THE INVENTION

The present invention provides novel dithiolane derivatives which can be used to ameliorate PPARγ-mediated diseases such as inflammatory and proliferative diseases and those that are characterized by inappropriate activation of nuclear transcription factors.

As such, in one embodiment, the present invention provides compounds of Formula A:

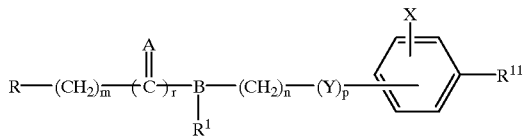

In Formula A, R is a functional group including, but not limited to R or S or racemic 1,2-dithiolan-3-yl, or achiral 1,2-dithiolan-4-yl, R or S or racemic 1-(1,3-dithiopropanyl); R or S or racemic S,S'-Diacyl-[1-(1,3-dithiopropanyl)], R or S or racemic or achiral 2-(1,3-dithiopropanyl), R or S or racemic or achiral S,S'-Diacyl-[2-(1,3-dithiopropanyl)]; and optionally substituted 3R or 3S or racemic 3H-benzo[d]1,2-dithiolen-6-yl (or also named as a 3H-benzo[1,2]dithiol-6-yl) moieties. The term "diacyl" as used herein means the either one sulfur or both sulfurs are substituted with an acyl group. In a preferred embodiment, the "diacyl group" are amino acid derivatives and thus, the compounds of Formula A are soluble in aqueous solution.

$R^1$, in Formula A, is a functional group including, but not limited to, hydrogen, alkyl, arylalkyl and aryl.

$R^{11}$, in Formula A, is a functional group including, but not limited to R, S or racemic—$CH_2(Z)CHCO_2R^2$, —$CH_2CO_2R^{12}$, —$CO_2R$. R is a functional group including, but not limited to, hydrogen, alkyl, arylalkyl and aryl.

A, in Formula A, is oxygen or, in an alternative embodiment, A, together with the carbon to which it is bound is a methylene group.

B, in Formula A, is a functional group including, but not limited to, N, O and S, provided that when B is O or S then $R^1$ is absent.

X, in Formula A, is a functional group including, but not limited to, hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$. $R^3$ and $R^{10}$ are each independently functional groups including, but not limited to hydrogen, alkyl, arylalkyl and aryl.

Y, in Formula A, is a functional group including, but not limited to oxygen, S, SO, $SO_2$, $SO_2NH$, $SO_2NR^{12}$, $SO_3$, NH, $NR^{12}$. $R^{12}$ is a functional group including, but not limited to hydrogen, alkyl, arylalkyl and aryl.

Z, in Formula A, is a functional group including, but not limited to, R S-phenyl, S S-phenyl, racemic S-phenyl, $SCH_3$, $SCH_2CH_3$, O-phenyl, $OCH_3$, $SCH_2CH_3$, propyl, butyl, pentyl, hexyl, benzyl, haloalkyl, $NHR^{13}$, $NR^{13}R^{14}$. $R^{13}$ and $R^{14}$ are each independently functional groups including, but not limited to, —(CO)alkyl, optionally substituted —(CO)aryl, optionally substituted —(CO)arylalkyl, optionally substituted —(CO)heteroaryl and —CHO.

In Formula A, in the index "m" is an integer from 1 to 8 inclusive, r is 0 or 1; n is 0,2,3,4; and p is 0 or 1.

In Formula A, when n is 0 then Y is not O, S, N, as this would result in N-O, N-S, and N-N bonds.

Formula I, II, IV, and V are preferred embodiments of Formula A.

In another embodiment, the present invention provides compounds of Formula

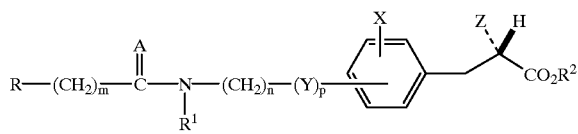

In Formula I, R is a functional group including, but not limited to R or S or racemic 1,2-dithiolan-3-yl, or achiral 1,2-dithiolan-4-yl, R or S or racemic 1-(1,3-dithiopropanyl); R or S or racemic S,S'-Diacyl-[1-(1,3-dithiopropanyl)], R or S or racemic or achiral 2-(1,3-dithiopropanyl), R or S or racemic or achiral S,S'-Diacyl-[2-(1,3-dithiopropanyl)]; and optionally substituted 3R or 3S or racemic 3H-benzo[d]1,2-dithiolen-6-yl (or also named as a 3H-benzo[1,2]dithiol-6-yl) moieties.

$R^1$, in Formula I, is a functional group including, but not limited to hydrogen, alkyl, arylalkyl and aryl.

$R^2$, in Formula I, is a functional group including, but not limited to hydrogen, alkyl, arylalkyl and aryl.

A, in Formula I, is oxygen or, in an alternative embodiment, A, together with the carbon to which it is bound is a methylene group.

X, in Formula I, is a functional group including, but not limited to, hydrogen, halogen, $OR^3$, $NH^2$ $NHR^3$, $NR^3$ $R^{10}$, $SR^3$, $SOR^3$, $SONH_2$, $SONHR_3$, $SO_2NH_2$, $SO_2R_3$, $SO_2NHR^3$ and $SO_3R^3$. $R^3$ and $R^{10}$ are each independently functional groups including, but not limited to, hydrogen, alkyl, arylalkyl and aryl. In a preferred embodiment, "X" is meta to the fixed functional group, i.e., the group comprising "Z".

Y, in Formula I, is a functional group including, but not limited to, oxygen, S, SO, $SO_2$, $SO_2NH$, $SO_2NR^3$, $SO_3$, NH, $NR^3$. $R^3$, in Formula I, is a functional group including, but not limited to, hydrogen, alkyl, arylalkyl and aryl. In a preferred embodiment, "Y" is para to the fixed functional group, i.e., the group comprising "Z".

Z, in Formula I, is a functional group including, but not limited to, R S-phenyl, S S-phenyl, racemic S-phenyl, $SCH_3$, $SCH_2CH_3$, O-phenyl, $OCH_3$, $SCH_2CH_3$, propyl, butyl, pentyl, hexyl, benzyl and haloalkyl.

In Formula I, the index "m" is an integer from 1 to 8 inclusive.

In Formula I, the index "n" is 0, 2, 3, 4 and the index "p" is 0 or 1.

In Formula I, when n is 0 then Y is not O, S, N, as this would result in N—O, N—S, and N—N bonds.

In another embodiment, the present invention provides a compound of Formula II:

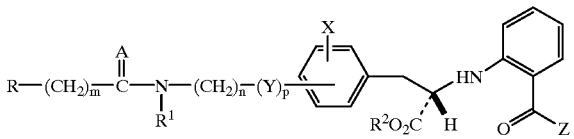

In Formula II, R is a functional group including, but not limited to, R or S or racemic 1,2-dithiolan-3-yl, or achiral 1,2-dithiolan-4-yl, R or S or racemic 1-(1,3-dithiopropanyl); R or S or racemic S,S'-Diacyl-[1-(1,3-dithiopropanyl)], R or S or racemic or achiral 2-(1,3-dithiopropanyl), R or S or racemic or achiral S,S'-Diacyl-[2-(1,3-dithiopropanyl)]; and optionally substituted 3R or 3S or racemic 3H-benzo[d]1,2-dithiolen-6-yl (or also named as a 3H-benzo[1,2]dithiol-6-yl) moieties.

$R^1$, in Formula II, is a functional group including, but not limited to, hydrogen, alkyl, arylalkyl and aryl.

$R^2$, in Formula II, is a functional group including, but not limited to, hydrogen, alkyl, arylalkyl and aryl.

A, in Formula II, is oxygen or, in an alternative embodiment, A, together with the carbon to which it is bound is a methylene group.

X, in Formula II, is a functional group including, but not limited to, hydrogen, halogen, $OR^3$, $NH_2$, $NHR^3$, $NR^3R^{10}$, $SR^3$, $SOR^3$, $SONH_2$, $SONHR^3$, $SO_2NH^2$, $SO_2R^3$, $SO_2NHR^3$ and $SO_3R^3$. $R^3$ and $R^{10}$, are each independently functional groups including, but not limited to hydrogen, alkyl, arylalkyl and aryl. In a preferred embodiment, "X" is meta to the fixed functional group, i.e., the group comprising "Z".

Y, in Formula II, is a functional group including, but not limited to, oxygen, S, SO, $SO_2$, $SO_2NH$, $SO_2NR^3$, $SO_3$, NH, $NR^3$. $R^3$ is a functional group including, but not limited to, hydrogen, alkyl, arylalkyl and aryl. In a preferred embodiment, "Y" is para to the fixed functional group, i.e., the group comprising "Z".

Z, in Formula II, is a functional group including, but not limited to, R S-phenyl, S S-phenyl, racemic S-phenyl, $SCH_3$, $SCH_2CH_3$, O-phenyl, $OCH_3$, $SCH_2CH_3$, propyl, butyl, pentyl, hexyl, benzyl and haloalkyl.

In Formula II, the index "m" is an integer from 1 to 8 inclusive, the index "n" is 0, 2, 3 or 4; and the index "p" is 0 or 1. In Formula II, when n is 0 then Y is not O, S, N, as this would result in N—O, N—S, and N—N bonds.

In yet another embodiment, the present invention provides a compound of Formula III:

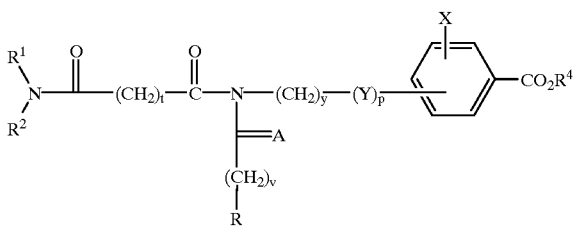

In Formula III, R is a functional group including, but not limited to, R or S or racemic 1,2-dithiolan-3-yl, or achiral 1,2-dithiolan-4-yl, R or S or racemic 1-(1,3-dithiopropanyl); R or S or racemic S,S'-Diacyl-[1-(1,3-dithiopropanyl)], R or S or racemic or achiral 2-(1,3-dithiopropanyl), R or S or racemic or achiral S,S'-Diacyl-[2-(1,3-dithiopropanyl)]; and optionally substituted 3R or 3S or racemic 3H-benzo[d]1,2-dithiolen-6-yl (or also named as a 3H-benzo[1,2]dithiol-6-yl) moieties.

$R^1$, in Formula III, is a functional group including, but not limited to hydrogen, alkyl, arylalkyl and aryl.

$R^2$, in Formula III, is a functional group including, but not limited to, hydrogen, alkyl, arylalkyl, and aryl.

$R^4$, in Formula III, is a functional group including, but not limited to hydrogen and alkyl.

A, in Formula III, is a member selected from the group consisting of oxygen or, in an alternate embodiment, A, together with the carbon to which it is bound is a methylene group.

X, in Formula III, is a functional group including, but not limited to hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$. $R^3$ and $R^{10}$ are each independently a functional group consisting of hydrogen, alkyl, arylalkyl and aryl. In a preferred embodiment, "X" is meta to the fixed functional group, i.e., the group comprising "$R^4$".

Y, in Formula III, is a functional group including, but not limited to oxygen, S, SO, $SO_2$, $SO_2NH$, $SO_2NR^3$, $SO_3$, NH, $NR^3$, wherein $R^3$ is a functional group including, but not limited to hydrogen, alkyl, arylalkyl and aryl. In a preferred embodiment, "Y" is para to the fixed functional group, i.e., the group comprising "$R^4$".

In Formula III, the index "t" is an integer from 1 to 5 inclusive; the index "v" is an integer from 2 to 8 inclusive; and the index "y" is an integer from 2 to 4 inclusive; and the index "p" is 0 or 1.

In still yet another embodiment, the present invention provides a compound of Formula IV:

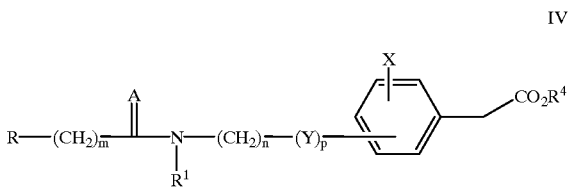

In Formula IV, R is a functional group including, but not limited to R or S or racemic 1,2-dithiolan-3-yl, or achiral 1,2-dithiolan-4-yl, R or S or racemic 1-(1,3-dithiopropanyl); R or S or racemic S,S'-Diacyl-[1-(1,3-dithiopropanyl)], R or S or racemic or achiral 2-(1,3-dithiopropanyl), R or S or racemic or achiral S,S'-Diacyl-[2-(1,3-dithiopropanyl)]; and optionally substituted 3R or 3S or racemic 3H-benzo[d]1,2-dithiolen-6-yl (or also named as a 3H-benzo[1,2]dithiol-6-yl) moieties.

$R^1$, in Formula IV, is a functional group, including, but not limited to, hydrogen, alkyl, arylalkyl and aryl.

$R^4$, in Formula IV, is a functional group including, but not limited to, hydrogen and alkyl.

A, in Formula IV, is oxygen or together with the carbon to which it is bound is a methylene group.

X, in Formula IV, is a functional group including, but not limited to, hydrogen, halogen, $OR^3$, $NH_2$, $NHR^3$, $NR^3R^{10}$, $SR^3$, $SOR^3SONH^2$, $SONHR^3$, $SO_2NH_2$, $SO_2R^3$, $SO_2NHR^3$ and $SO_3R^3$. $R^3$ and $R^{10}$ are each independently functional group including, but not limited to, hydrogen, alkyl, arylalkyl and aryl. In a preferred embodiment, "X" is meta to the fixed functional group, i.e., the group comprising "$R^4$".

Y, in Formula IV, is a fuinctional group including, but not limited to, oxygen, S, SO, $SO_2$, $SO_2NH$, $SO_2NR^3$, $SO_3$, NH, $NR^3$, wherein $R^3$, is a functional group including, but not limited to, hydrogen, alkyl, arylalkyl and aryl. In Formula IV, the index "m" is an integer from 1 to 8 inclusive; the index "n" is 0, 2, 3 or 4; and the index "p"0 is 0 or 1. In Formula IV, when n is 0 then Y is not O, S, N, as this would result in N—O, N—S, and N—N bonds. In a preferred embodiment, "Y" is para to the fixed functional group, i.e., the group comprising "R⁴".

In still yet another embodiment, the present invention provides a compound of Formula V:

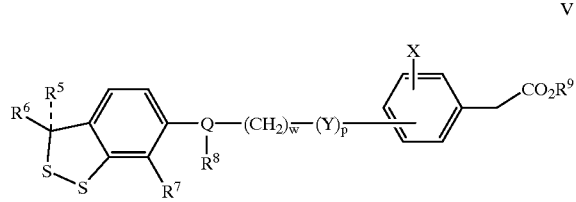

V

In Formula V, $R^5$ and $R^6$ are each independently functional groups including, but not limited to, hydrogen, alkyl, arylalkyl and aryl, and where C-3 is either R, S, racemic or achiral.

$R^7$, in Formula V, is a functional group including, but not limited to, hydrogen and alkyl.

$R^8$, in Formula V, is a functional group including, but not limited to, hydrogen and alkyl or is absent.

In an alternative aspect, $R^7$ and $R^8$ and the atoms to which they are bound, join to form a 5-, or 6-membered aryl or heteroaryl ring.

$R^9$, in Formula V, is a functional group including, but not limited to, hydrogen and alkyl.

Q, in Formula V, is a functional group including, but not limited to, O, S, NH and NCH₃.

X, in Formula V, is a functional group including, but not limited to, hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$. $R^3$ and $R^{10}$ are each independently a functional group including, but not limited to, hydrogen, alkyl, arylalkyl and aryl. In a preferred embodiment, "X" is meta to the fixed functional group, i.e., the group comprising "R⁹".

Y, in Formula V, is a functional group including, but not limited to, oxygen, S, SO, SO₂, SO₂NH, SO₂NR¹, SO₃, NH, $NR^3$. $R^3$ is a functional group including, but not limited to, hydrogen, alkyl, arylalkyl and aryl. In a preferred embodiment, "Y" is para to the fixed functional group, i.e., the group comprising "R⁹".

In Formula V, the index "w" is an integer from 2 to 6 inclusive; and the index "p" is 0 or 1.

In other aspects, the present invention relates to a pharmaceutical composition comprising a compound of the present invention or a pharmaceutically acceptable salt or solvate thereof; and a pharmaceutically acceptable carrier.

In another aspect, the present invention relates to a method of treating a PPARγ mediated disease or oxidative stress, comprising administering a therapeutically effective amount of a compound of the present invention or mixtures thereof to an individual suffering from a PPARγ-mediated disease.

In other aspects, this invention provides methods for synthesizing the compounds of Formula A I, II, III, IV, and V. These and other aspects and advantages will become more apparent hen read with the detailed description and drawings which follow.

BRIEF DESCRIPTION OF THE DRAWINGS

FIG. 1 illustrates dithiolanes for synthesis of certain compounds of the present invention.

GLOSSARY

Figure 2:
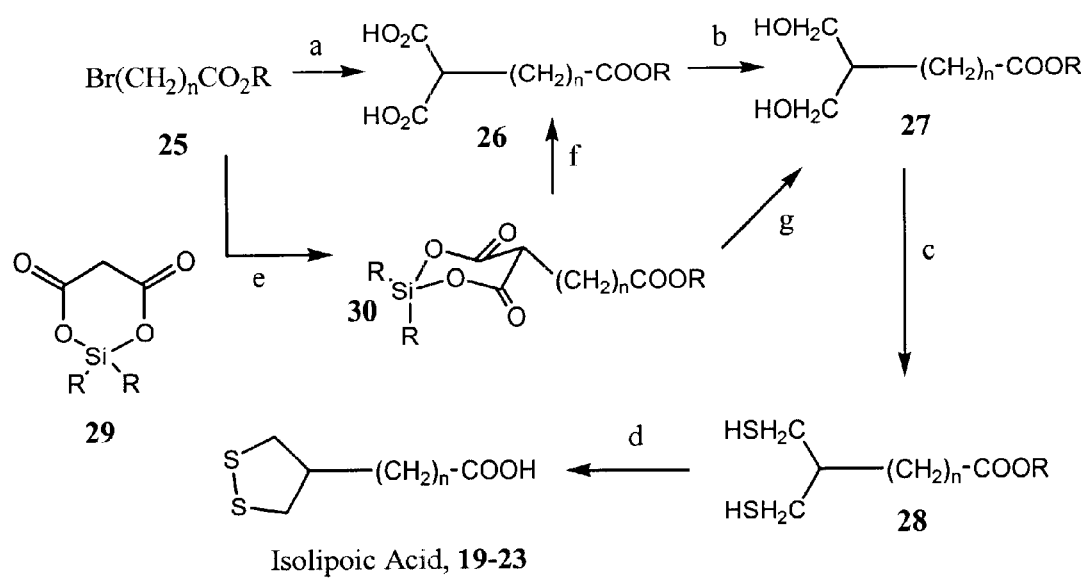
FIG. 2 illustrates a general synthetic scheme for the production of isolipoic acids 19–23. The key to the reagents is as follows: a) malonic acid, 2NaH, n-BuLi, THF; 25; b) BH₃, THF, 0° C.; c) CH₃SO₂Cl, pyridine; then NaSH; d) NaOH, O₂, EtOH; e) NaH, THF, 25; f) TBAF, THF; g) (RO)$_m$AlH$_n$Li, THF or NaBH₄, THF.

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

The term "alkylene" refers to a divalent alkyl group as defined above, such as methylene (—CH$_2$—), propylene (—CH$_2$CH$_2$CH$_2$—), chloroethylene (—CHClCH$_2$—), 2-thiobutene—CH$_2$CH(SH)CH$_2$CH$_2$1-bromo-3-hydroxyl-4-methylpentene (—CHBrCH$_2$CH(OH)CH (CH$_3$)CH$_2$—), and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aryl" denotes a chain of carbon atoms which form at least one aromatic ring having preferably between about 6–14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "acyl" denotes the —C(O)R group, wherein R is alkyl or aryl as defined above, such as formyl, acetyl, propionyl, or butyryl.

The term "alkoxy" denotes —OR—, wherein R is alkyl.

The term "amido" denotes an amide linkage: —C(O)NR—(wherein R is hydrogen or alkyl).

The term "amino" denotes an amine linkage: —NR—, wherein R is hydrogen or alkyl.

The term "3H-benzo[d]1,2-dithiolen-6-yl" and "3H-benzo[1,2]dithiol-6-yl" are used interchangeably and may be optionally substituted with alkyl, alkenyl, alkoxy, amino, halo, aryl, etc. These moieties also include structures wherein the disulfide group (S-S) has been reduced to the dithiol (—SH —SH). Further, the dithiol group can be optionally substituted with acyl (—COS—), carbonate (—OCOS—), carbamate (—NHCOS—), alkyl, alkenyl, alkoxy, amino, halo, aryl, etc.

The term "carboxyl" denotes —C(O)O—, and the term "carbonyl" denotes —C(O)—.

The term "carbonate" indicates —OC(O)O—.

The term "carbamate" denotes —NHC(O)O—, and the term "urea" denotes—NHC(O)NH—.

The term "R or S or racemic 1,2-dithiolan-3-yl or 1,2-dithiolan-4-yl refer to a 5-membered heterocyclic ring consisting of two sulfur atoms at the 1 and 2 positions and carbon atoms at the remaining positions. The point of attachment can either be the C-3 or C-4 position, where these carbon atoms can be chiral, racemic or achiral.

The term "1-(1,3-dithiopropanyl); R or S or racemic S,S'-Diacyl-[1-(1,3-dithiopropanyl)], 2-(1,3-dithiopropanyl), S,S'-Diacyl-[2-(1,3-dithiopropanyl" refer to the corresponding reduced dithiolanes [(HSCH$_2$)$_2$CH—] or [(HSCH$_2$CH$_2$(HS)CH—)] and the corresponding thioesters and other acyl derivatives of the thiol groups such as a diacetate [(CH$_3$COSCH$_2$)$_2$CH—] or [(CH$_3$COSCH$_2$CH$_2$(CH$_3$COS)CH—)], a disuccinate [(HOOCCH$_2$CH$_2$COSCH$_2$)$_2$CH—] or [(HOOCCH$_2$CH$_2$COSCH$_2$CH$_2$(HOOCCH$_2$CH$_2$COS)CH—)], or its metal salt; a diglycinate [(ClNH$_3$CH$_2$COSCH$_2$)$_2$CH—] or [(ClNH$_3$CH$_2$COSCH$_2$CH$_2$(ClNH$_3$CH$_2$COS)CH)], or mixed esters such as a mono-glycinate-mono-propionate (ClNH$_3$CH$_2$COSCH$_2$)(CH$_3$CH$_2$COSCH$_2$)CH—] or [(ClNH$_3$CH$_2$COSCH$_2$CH$_2$(CH$_3$CH$_2$COSCH$_2$)CH—)] or [(CH$_3$CH$_2$COSCH$_2$CH$_2$(ClNH$_3$CH$_2$COSCH$_2$)CH—)]. The term "diacyl" as used herein means that either one sulfur or both sulfurs are substituted with an acyl group i.e., S—C(O)R, (e.g. S—C(O)R[15, 16, 17] in FIG. 20) wherein R is hydrogen, optionally substituted alkyl or optionally substituted aryl as defined above and includes such as groups as formyl, acetyl, propionyl, or butyryl. Alternatively, the acyl group is an amino acid, an aminoalkyl group, a carboxyalkyl, a carboxyalkyl ester, an aminoarylalkyl, a carboxylarylalkyl and ester. See FIG. 20 for an example of a diacyl compound 132(b, c, d).

The term "amino acid derivative" refers to an amino acid wherein the hydrogen on the oc-carboxylic acid function has been removed to generate a carboxyl group. (See, WO 00/53601, published Sep. 14, 2000). Amino acids include, but are not limited to, the term amino acid as used herein refers to naturally occurring amino acids, amino acid analogs, and amino acid mimetics that function in a manner similar to the naturally occurring and analog amino acids. Naturally occurring amino acids are those encoded by the genetic code, as well as those amino acids that are later modified, e.g., hydroxyproline, γ-carboxyglutamate, and O-phosphoserine. Amino acid analogs refers to synthetic amino acids that have the same basic chemical structure as a naturally occurring amino acid, i.e., an α-carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Both naturally occurring and analog amino acids can be made synthetically by methods well known to those skilled in the art. Amino acid mimetics refer to chemical compounds that have a structure that is different from the general chemical structure of an amino acid, but that function in a manner similar to a naturally occurring amino acid. In a preferred embodiment, the "diacyl group" are amino acid derivatives and thus, the compounds of Formulae A, I-V are soluble in aqueous solution.

The term "$EC_{50}$" refers to the concentration of a compound required to activate 50% of the receptors that bind the compound present in a sample or a subject. Thus, in the present invention, the $EC_{50}$ of a PPARγ modifier is the concentration of the modifier that activates 50% of the PPARγ present in the sample or organism. The term "activate" has its ordinary meaning, i.e., cause to function or act.

The term "peroxisome proliferator activating receptor-gamma" or "PPARγ" refers to either the $\gamma_1$, $\gamma_2$ or $\gamma_3$ isotypes or a combination of all isotypes of PPARγ. PPARs are nuclear receptors which naturally bind to fatty acids and which have been implicated in adipocyte differentiation (see, Perlmann et al., *Cell*, 90:391–397 (1997)).

The term "peroxisome proliferator activating receptor-alpha" is also referred to as "PPARα".

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described.

The terms "cancer, neoplasm or malignancy" include primary and metastatic disease. So, for example, cervical cancer includes the neoplasm at the primary site (cervix) and metastatic cervical cancer, regardless of site of metastasis, such as skeleton, brain, etc.

The term "inflammatory disease" includes diseases (treatable or preventable with compounds described in this invention) including, but not limited to, a. T-lymphocyte activation and other T-lymphocyte-related disorders b. inflammatory cytokine (e.g. TNF-alpha, interleukin (IL)-1-alpha, IL-1-beta, IL-2, IL-6) production c. activation of nuclear factors that promote transcription of genes encoding inflammatory cytokines. Examples of these nuclear transcription factors include but are not restricted to: nuclear factor-kappaB (NF-kappaB), activated protein-1 (AP-1), nuclear factor of activated T cells (NFAT)

The term "diabetes," unless stated or qualified otherwise, refers to all variant forms of diabetes mellitus (DM), including type 1 DM, type 2 DM, gestational diabetes, juvenile diabetes, etc.

As used herein, the term "oxidative stress" refers to diseases or conditions that involve generation of active oxygen species and free radicals, resulting in the imposition of oxidative stress concomitant with the disease state. Examples of diseases imposing oxidative stress are dyslipidemias, diabetes mellitus and insulin resistant states, chronic viral infections (e.g. HIV, CMV, HSV, HBV, HCV infections), neurodegenerative diseases (e.g. Alzheimer's disease, multiple sclerosis, Parkinson's disease), cardiovascular disease (e.g. atherosclerosis, atherogenesis, vascular restenosis, congestive heart failure), diseases or conditions involving hypoxemia and hypoxic stress (stroke, vascular occlusive disease, MI, atherosclerosis, retinitis, retinal vein occlusion, hypoxic retinopathy, macular degeneration).

DETAILED DESCRIPTION OF THE INVENTION AND PREFERRED EMBODIMENTS

I. COMPOUNDS AND SYNTHESIS

The synthetic preparation of the compounds of the present invention are presented in the figures. In preferred aspects, the dithiolanes in FIG. 1 are used. Racemic compounds (3, 6, 9) can be resolved into either R or S enantiomer by conventional means (e.g. crystallization from a diastereomeric mixture using the ammonium salt of chiral amine such as ephedrine), or using chiral chromatography supports.

The lipoic acids 1,2, and 3 are known compounds (see, Biewenga, G. P., et al., *Antioxidants in Health and Disease*, Vol. 6 (1997); Fadnavis, N. W., et al., *Tetrahedron: Asymmetry*, 9(23):4109–4112 (1998)). R-Lipoic acid 1 is the naturally occurring form of lipoic acid, while rac-lipoic acid 3 is currently sold as a dietary supplement. S-Lipoic acid 2 has been described as well. The synthesis of shorter chain versions of 3 have been reported, such as norlipoic acid 6 (see, Moreau, W. M., *German Patent* DE 2132063 (1972)) dinorlipoic acid 9 (see, Shih, J. C. H., et al., *J Heterocycl. Chem.*, 11(2):119–23 (1974)) trinorlipoic acid 15 (see, Hoyle, N. R., *German Patent* DE 3,900,649 (1990)) and tetranorlipoic acid 18 (see, Schepkin, V., et al., *Free Rad. Res.*, 25(3):195–205 (1996)). The longer chain caproate version, or racemic 1,2-dithiolane-3-hexanoic acid 12, is also known (see, Loeffelhardt, S., et al., *Biochim. Biophys. Acta*, 1297(1):90–98 (1996); Loeffelhardt, S., et al., *Bio-* chem. Pharmacol, 50(5):637–46 (1995); Kumagai, M., et al., Japanese Pat. JP 630708 (1963)). On the other hand, other than tetranorisolipoic acid 24 (see, Morimoto, K., et al., Japanese Patent JP 63,104,051 (1988)), the other isolipoic acids 19–23 do not appear to have been prepared. Potential precursors to the isolipoic acids have been reported (see, Jones, W. T., et al., PCTInt. Appl. (1993)).

A general synthetic figure for the production of isolipoic acids 19–23 is shown in FIG. 2. As shown therein, ethyl bromoalkanoates 25, where n=1, 2, 3, 4 or 5, are alkylated by malonic acid trianion to furnish 26 after careful acidification. Borane reduction of the acid moieties occurs much more rapidly than reduction of the ester group to give the diols 27 (see, Choi, Y. M., et al., J Org. Chem., 54:1194–1198 (1989)). In certain instances, particularly where n=1 and 2, lactonization occurs, and in these instances, the unwanted lactones can be recycled back to the ester-diols 27 by alcoholysis. With diols 27 in hand, simple functional group interconversion to dithiol 28 occurs in a one pot procedure by mesylation followed by treatment with NaSH or related inorganic sulfides such as sodium disulfide. Air oxidation will effect conversion of the 1,3-dithiol to 1,2-dithiolane, thus ester hydrolysis under oxygen generates the desired isolipoic acids 19–23.

Alternatively, a silicon version of Meldrums Acid, 29, is straightforward to prepare from malonic acid itself, and will effect Sn2 displacement of bromides 25. The resulting adduct 30 will then readily undergo mild desilylation with fluoride ion to give acid 26, or will itself undergo facile selective reduction, particularly when R is a bulky alkyl group. Additionally, conversion of malonate acids into mixed anhydrides allows for borohydride reduction to alcohol 27, again without effecting the ester moiety (see, Fadel, A., et al., Tetrahedron Lett., 30:6687–6690 (1989)).

Once the acids have been prepared, amide formation with the appropriate amines will provide the desired target compounds.

In one aspect, the present invention provides compounds of Formula A:

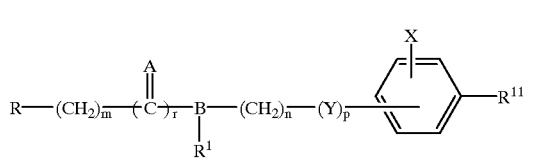

A wherein R, $R^1$, $R^2$, $R^{11}$, A, B, X, Y, Z, m, r, n, and p have been defined above. Formula I, II, IV, and V are preferred embodiments of Formula A.

In certain aspects, preferred compounds of Formula A have structures of Formula I:

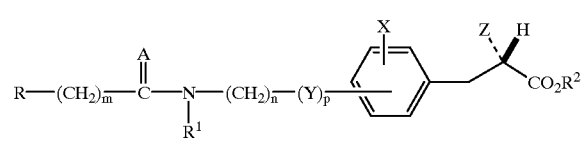

I wherein R, $R^1$, $R^2$, A, X, Y, Z, m, n, and p have been defined above.

Figure 3:
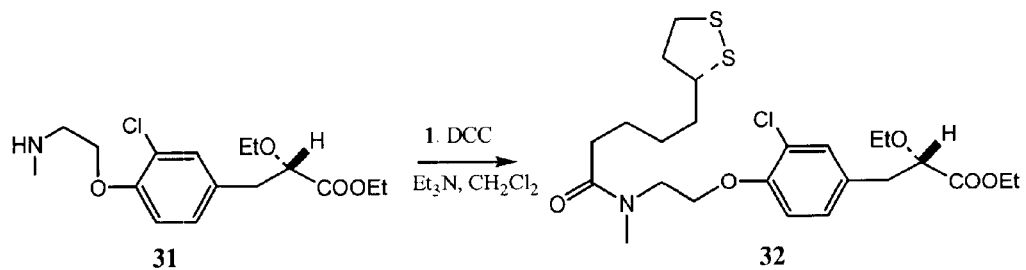
FIG. 3 illustrates a method to synthesize compounds of Formula I of this invention.
Figure 4:
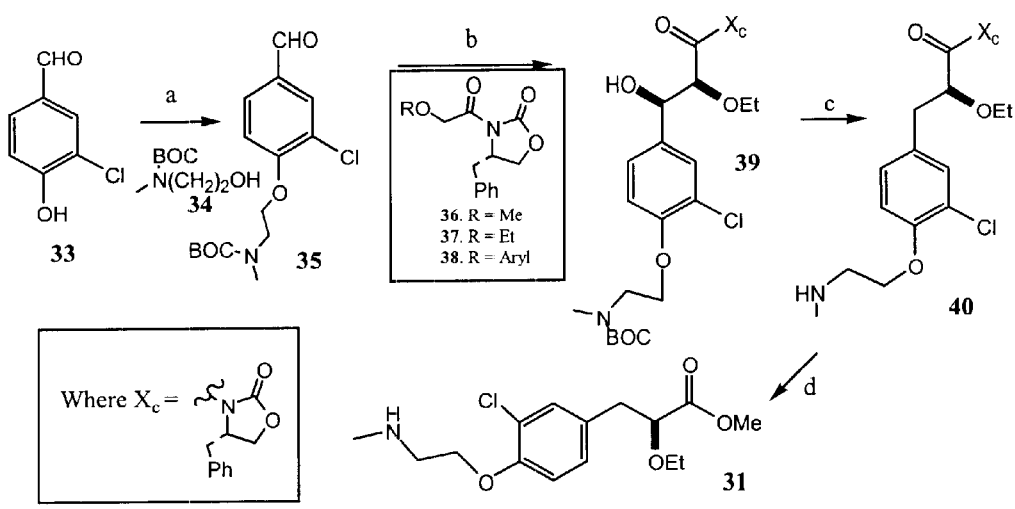
FIG. 4 illustrates a method to synthesize compounds of Formula I of this invention. The key to the reagents is as follows: a 34, MsCl, pyridine, CH₂Cl₂; add to 33+NaH; b) 37, Bu₂BOTf, 1.2 Et₃N, CH₂Cl₂; c) Et₃SiH, CF₃COOH; d) NaOMe, MeOH.

FIG. 3 shows a preferred embodiment of Formula I. As shown therein, the amine 31 is linked with R-lipoic acid to give the target 32. The corresponding amine 31 is prepared by a modification of reported work as shown in FIG. 4, involving Evans Aldol condensation of BOC-aldehyde 35 with the boron enolate of 37, to give 39 as precedented (see, Haigh, D., et al., Tetrahedron: Asymmetry, 10:1353–1367 (1999)). Benzylic hydrogenolysis of 39 with trialkylsilane and TFA gives, with simultaneous BOC deprotection, the propionate 40. Transesterification with recycling of the serine-based oxazolidinone chiral auxiliary $X_c$ will occur upon reaction with NaOMe in MeOH, giving the penultimate intermediate 31.

Figure 5:
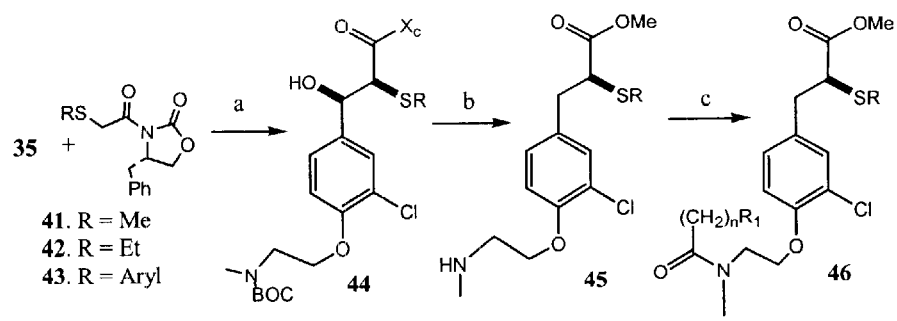
FIG. 5 illustrates a method to synthesize compounds of Formula I of this invention. The key to the reagents is as follows: a) 41–43, 1.1 Bu₂BOTf, 1.2 Et₃N, CH₂Cl₂; b) i) Et₃SiH, CF₃COOH, CH₂Cl₂; ii) 1.1 NaOMe, MeOH; c) Acids 1–24, DCC, Et₃N, CH₂Cl₂; then 45.

Any of the dithiolanes 1–24 will undergo coupling with 31 to furnish the target compounds. Furthermore, the procedure will work for the corresponding thioglycolate derivatives 39 by analogy to FIG. 4, as shown in FIG. 5. Thioglycolic acids are coupled with the oxazolidineone $X_c$ to provide various acyloxazolidineones 41–43. As before, these can be converted to the corresponding boron enolates with a borontriflate, and the resulting transient intermediates coupled with aldehdyes such as 35 to furnish syn-thioglycols 44. As before, hydrogenolysis with a silane and an acid will result in simultaneous BOC deprotection to furnish amine 45. Finally, coupling as before to lipoic acids 1–24 generates targets 46 from Formula I.

Figure 6:
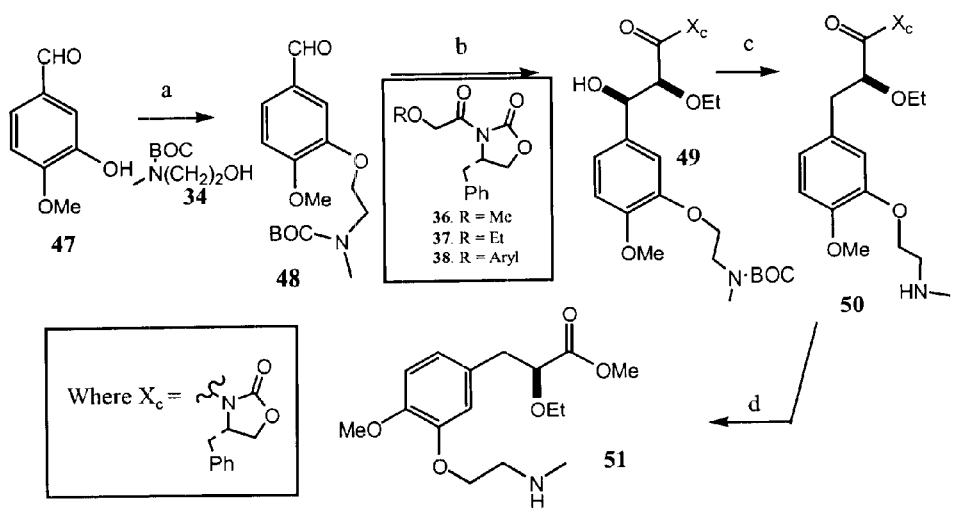
FIG. 6 illustrates a method to synthesize compounds of Formula I of this invention. The key to the reagents is as follows: a) 34, MsCl, pyridine, CH₂Cl₂; add to 47+NaH; b) 37, 1.1 Bu₂BOTf, 1.2 Et₃N, CH₂Cl₂; c) Et₃SiH, CF₃COOH; d) 1.1 NaOMe, MeOH.

In certain preferred respects, FIG. 6 shows a similar strategy is employed to prepare targets from Formula I wherein (Y)p is oriented meta. The amine 51 is prepared from isovanillin 47 by following a similar strategy as in FIG. 3. Coupling isovanillin with 34 provides 48 which can be coverted to 49. Silyl reduction in trifluoroacetic acid provides amine 50. The chiral auxillary is removed to be recycled and 50 coverted to the amine 51. Coupling the amine 51 with lipoic acids (1–24) furnishes preferred compounds of Formula I.

Figure 7:
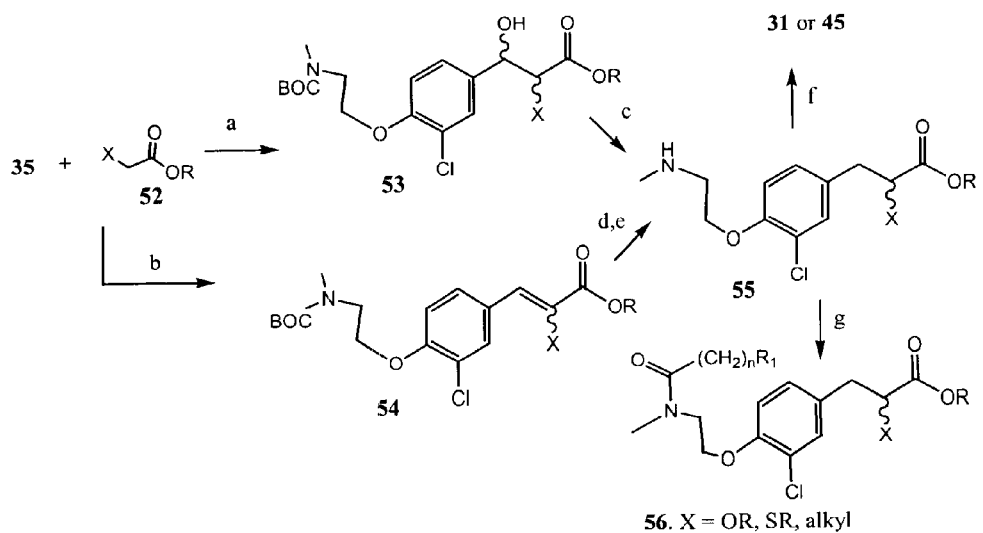
FIG. 7 illustrates a method to synthesize compounds of Formula I of this invention. The key to the reagents is as follows: a) LICA, THF, –78° C.; b) R₂NH₂OAc, toluene, 35; c) Et₃SiH, CF₃COOH, CH₂Cl₂; d) H₂, Pd/C, MeOH; e) TFA, CH₂Cl₂; f] i) NaOH, MeOH, water; ii) ephedrine, recrystallize; or chiral chromatography; or *R. delemar* lipase cleavage; iii) CH₂N₂; alternatively, *P. fluorescens* lipase, vinyl acetate; g) R₁ (CH₂)$_n$COOH, DCC, Et₃N, CH₂Cl₂; then 55 or 31 or 45.
Figure 8:
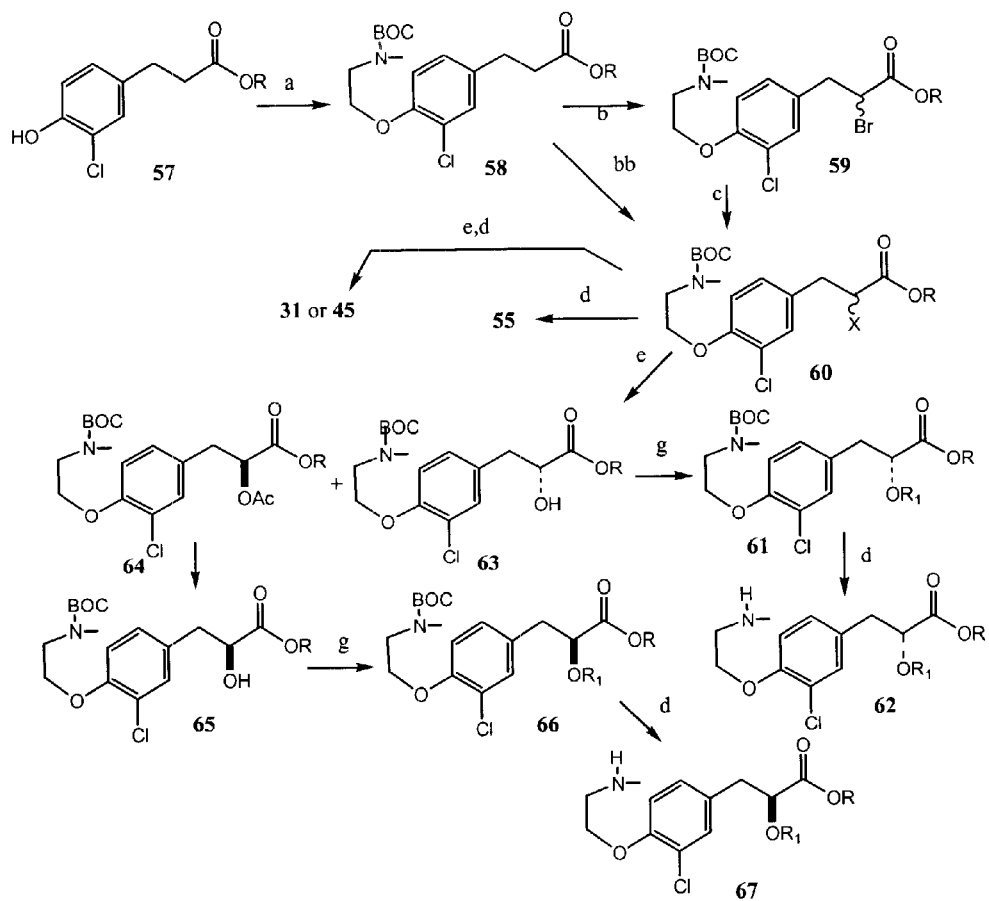
FIG. 8 illustrates a method to synthesize compounds of Formula I of this invention. The key to the reagents is as follows: a) 35, MsCl, pyridine, CH₂Cl₂; add to 57+NaH; b) R₁R₂NLi, THF, –78° C.; then NBS; bb) R₁R₂NLi, THF, –78° C.; then R₁-I (X becomes alkyl); c) RSNa; or ROK, ROH (Ag⁺¹); d)TFA; e] i) NaOH, MeOH, water; ii) ephedrine, recrystallize; or chiral chromatography; or *R. delemar* lipase cleavage; iii) CH₂N₂; e) when X=OH, *P. fluorescens* lipase, vinyl acetate; separate; f) NaHCO₃, MeOH; or Tosic acid, MeOH; g) R₁X, NaH, NaI, THF.

Other routes to functionalization of the propionate α-position have been described by more conventional achiral methodology (see, Haigh, D., et al., J Bioorg. Med. Chem., 7:821–830 (1999); Buckle, D. R., et al., Bioorg. Med. Chem. Lett., 6(17):2127–2130 (1996)). For example, as shown in FIG. 7, glycolate, thioglycolate, and alkanoate esters 52 (X is OR, SR, or R) can be deprotonated with lithium isopropylcyclohexylamide (LICA) and condensed with aldehydes such as 35 to give achiral aldol adducts 53 that can be hydrogenolyzed to the a-propionates 55 with simultaneous deprotection of BOC group by treatment with triethylsilane and acid, as before. Alternatively, especially in cases where X is OR or R, condensation under acid catalyzed conditions leads to cinnamate esters 54, whose hydrogenation should give the same α-propionates 55. The achiral product 55 will be amidated as in FIG. 3 by DCC coupling of acids 1–24, to furnish the target compounds 56. Alternatively, resolution of the corresponding acids of 55, and re-esterification will give chiral intermediates such as 31 and 45, both of which should also undergo coupling to active esters of 1–24, as shown in FIG. 3.

Another approach involves α-bromination of the appropriate dihydrocinnamates, and subsequent Sn2 displacement by nucleophiles to arrive at appropriate intermediates for coupling to lipoic acids, as shown in FIG. 7 (see, Buckle, D. R., et. al., Bioorg. Med. Chem. Lett., 6(17):2121–2126 (1996)). Thus, as before in FIG. 4, coupling of a phenol (e.g. 57) to the BOC-amino alcohol 35 affords the cinnamate 58. Generation of the enolate derived from 58 with LICA, following by in situ bromination of the enolate with N-bromosuccinimide (NBS) affords the a-bromocinnamate 59.

Figure 9:
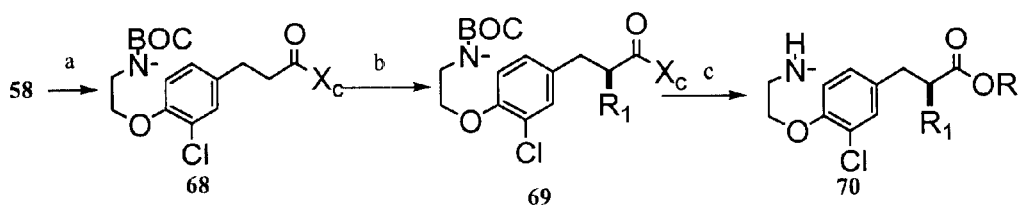
FIG. 9 illustrates a method to synthesize compounds of Formula I of this invention. The key to the reagents is as follows: a] i) NaOH, MeOH, HOH; ii) oxalyl chloride, pyridine, ether; iii) Prolinol, DMAP, CH₂Cl₂; b) 2LDA, then R₁X; c] i) NaOMe, MeOH; ii) TFA; alternatively, i) dil. HCl to 70, R=H; ii) EtO₂CCl, Et₃N, DMAP, ROH; iii) TFA.

Alkylation of the enolate with $R_1$-I will provides achiral X, where X is alkyl. Displacement of the bromo moiety in 59 occurs readily with thiolate salts, e.g. PhSNa prepared from NaH and PhSH, but may require exchanging conditions for alkoxides such as potassium salt in polar protic media. With the thioethers or alkoxides 60 in hand, deprotection of the BOC group then affords the N-methyl amines 55. As before, resolution of 60 is possible, leading to chiral intermediates en route to products linked to lipoic acids 1–20 24. Thus, 60 is selectively hydrolyzed, diastereomeric salt formed with ephedrine, and crystallized to give enantiomerically pure acid corresponding to 60; esterification gives R or S 60. Alternatively, *R. delemar* lipase cleavage of ester 60 leads to a mixture of enantiomerically pure acid plus enantiomerically pure ester, readily separated now on the basis of acidity; esterification gives R or S 60. Another approach when X=OH (e.g, X is OH) is to selectively acetylate one of the alcohols with *P. fluorescens* lipase, ultimately allowing the mixture to be separated by chromatography (acetate vs. alcohol). Subsequent deacylation will then lead to each R or S alcohol of 60 (X=OH), 63 and 65. When X is OH, alkylation with $R_1X$ gives analogs having $R_1O$ groups a to the carbonyl. For the examples where the group adjacent to the carboxy moiety is alkyl (FIG. 9, e.g. where $R_1$ is Et, Pr, or $PhCH_2CH_2CH_2$—), chirality can be induced by alkylation of the enolate of the Prolinol auxiliary, giving 69 (see, Evans, D. A., et al., *J Amer. Chem. Soc.*, 103:2876–2878 (1981)).

The auxiliary will be recycled and the alkyl ester regenerated in one pot, as before, by methanolysis (or alcoholysis) with NaOMe furnishing 69. If retention of chirality is an issue in these alkyl cases, more mild conditions are employed (e.g., dilute HCl, reflux, then $NaHCO_3$ quench) (see, Evans, D. A., et al., *J Amer. Chem. Soc.*, 103:2876–2878 (1981)) to give the acid (R is H) initially, and mild esterification via active ester should then afford the configurationally secure S adducts 69. Removal of the BOC group from the side chain amine may occur during prolinol removal, or may require a separate step to give the free amine 70 ready for coupling to lipoic acids.

In another aspect, preferred compounds of Formula A relate to compounds of Formula II:

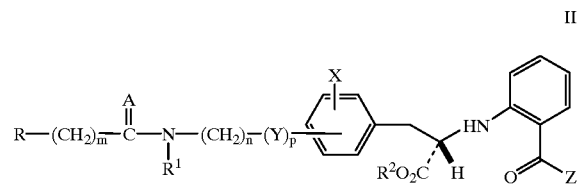

wherein R, $R^1$, $R^2$, A, X, Y, Z, m, n, and p have been defined above.

Figure 10:
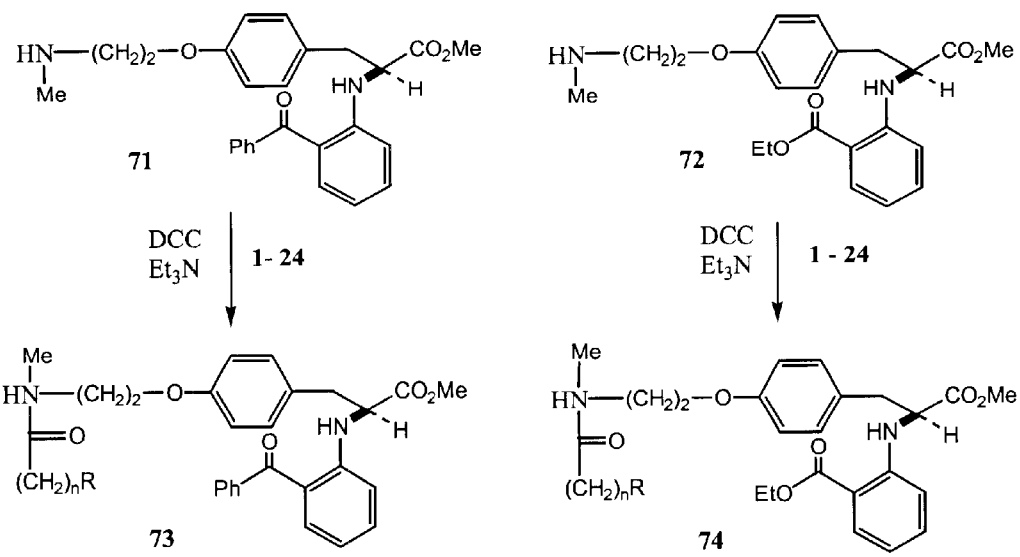
FIG. 10 illustrates a method to synthesize compounds of Formula II of this invention.

With reference to FIG. 10, the amine 71 required for coupling to lipoic acids 1–24 has been described starting from naturally occurring S-tyrosine methyl ester (see, Henke, B. R., et al., *J Med. Chem.*, 41(25):5020–5036 (1998)). On the other hand, the anthranilate 72 has not been described as an intermediate, even though final adducts having this functionality are described (see, Cobb, J. E., et al., *J Med. Chem.*, 41(25):5055–5069 (1998)). Coupling of these amines (71 and 72) as before (see, FIG. 3) will provide access to the prodrug esters 73 and 74 as shown in FIG. 10.

Adaptation of other schemes illustrated in the figures for the preparation of 72 and related structures are based on related literature examples. Instead of using the known procedure of coupling 75 with 76 to give the anthranilate 77, use of the corresponding BOC-amino alcohol side-chain as described herein can be used.

Figure 11:
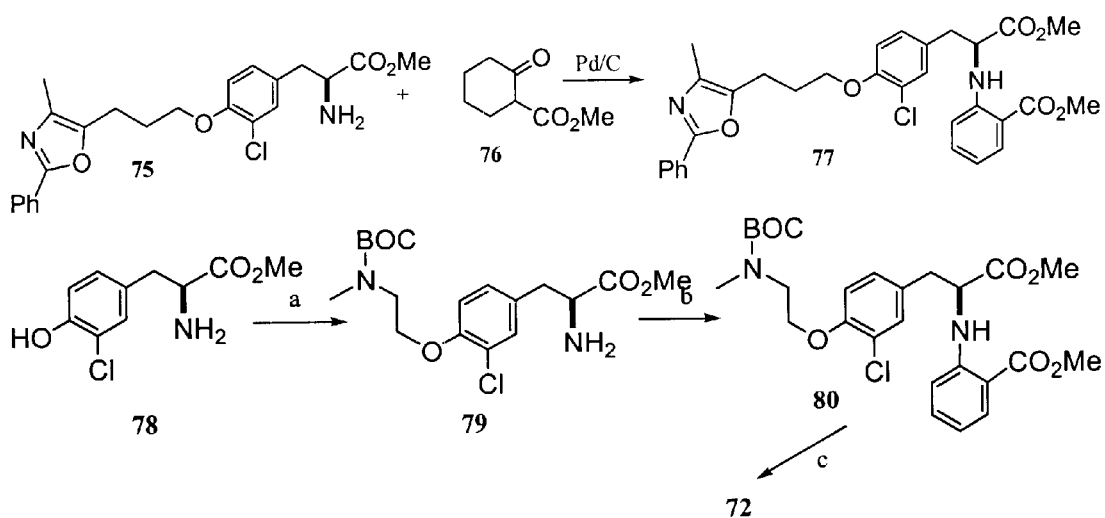
FIG. 11 illustrates a method to synthesize compounds of Formula II of this invention. The key to the reagents is as follows: a) 35+MsCl; then 78+NaH; b) 76, solvent, heat; then Pd/C, anisole, 190° C.; c) TFA.
Figure 12:
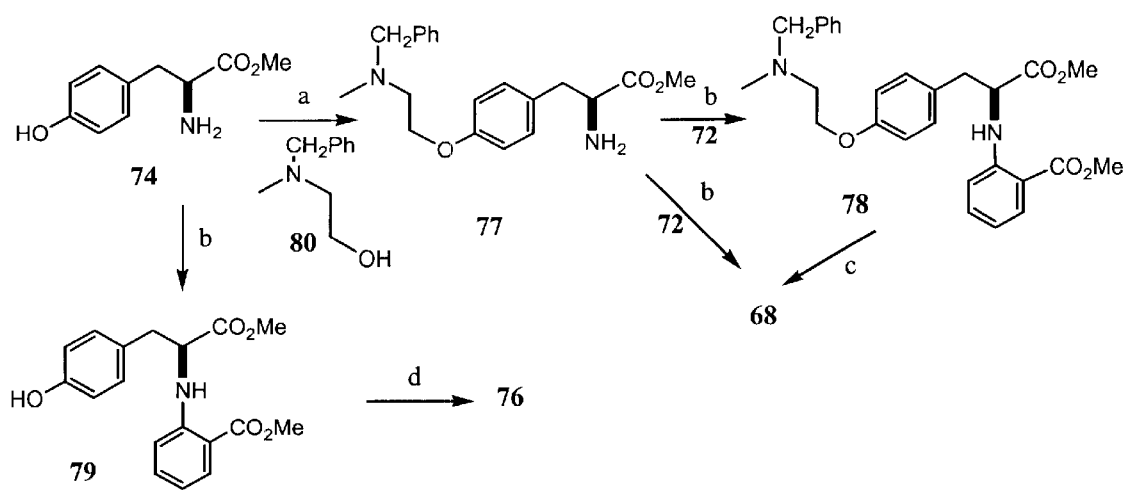
FIG. 12 illustrates a method to synthesize compounds of Formula II of this invention. The key to the reagents is as follows: a) 80+MsCl; then 74+NaH; b) 72, solvent, heat; then 10% Pd/C, anisole, 190° C.; then c) H₂; d) 35+MsCl; then 79+NaH.

With reference to FIG. 11, alkylation of the sodium salt of tyrosine methyl ester 78 with the mesylate derived from BOC-alcohol 35 provides 79. Condensation of carbomethoxycyclohexanone 76 with amine 79 first in toluene, is then followed by adding anisole and heating in the presence of 10% Pd/C to effect dehydrogenation to the anthranilate 80. Finally, deprotection affords the amine 72, ready for coupling to lipoic acids. Alternatively, different protection schemes can be employed in the preparation of 72. Tyrosine methyl ester can be directly converted to the anthranilate-phenol 83, and then coupled with 84 or 35. Also, groups other than BOC protection could be envisaged such as a N-benzyl group, which should be labile to the aromatization conditions, or if not, could be readily removed after aromatization by in situ addition of hydrogen gas as shown in FIG. 12. This chemistry works for the o-chlorotyrosine methyl ester as well (e.g. X is m—Cl in Formula II).

Figure 13:
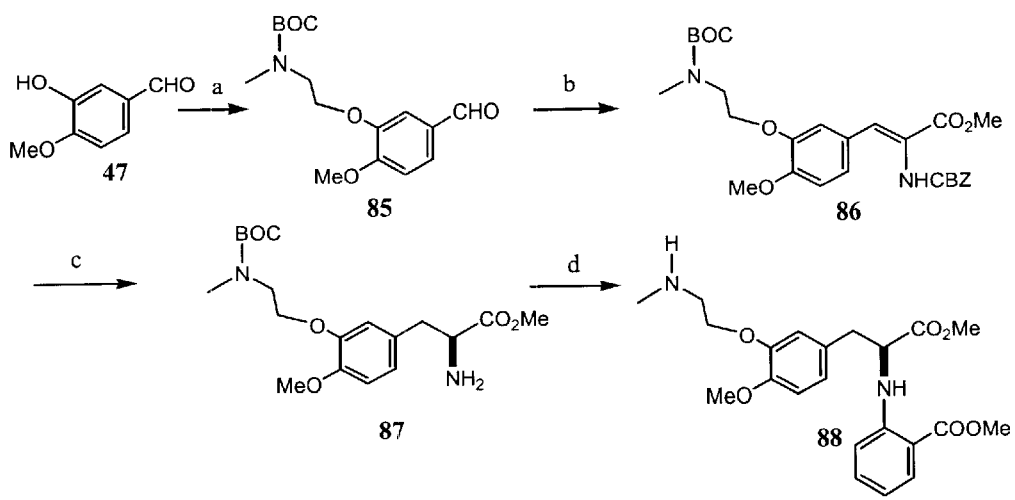
FIG. 13 illustrates a method to synthesize compounds of Formula II of this invention. The key to the reagents is as follows: a) 31+MsCl; then 47+NaH; b) 85+CBZNHCH₂CO₂Me, Piperidine solvent, heat; c)10% Pd/C, H₂; d) 76, toluene, anisole, Pd/C, TFA.

FIG. 13 is a representative example for the meta oriented targets in FIG. II (e.g, X is p—OMe). The amine 88 is prepared by converting isovanillin 47 to the ether 85 by alkylating with the mesylate. Condensation with glycinate followed by enantioselective reduction gives 87 which on condensation with carbomethoxycyclohexanone 76 as before (FIG. 12) in toluene followed by treatment with anisole and heating in the presence of 10% Pd/C gives the anthranilate. Finally deprotection gives 88 ready for coupling with lipoic acids.

In both Formula I and II, it has been demonstrated how to establish linkage of the antioxidant dithiolane (or reduced dithiol) moiety, through an amide bond, to arylpropionates (see, FIGS. 2–13). However, when the amide functionality is replaced by an amine, as indicated when A is a methylene group, a dramatic shift in the physiochemical and pharmacodynamic properties occurs such as increased water solubility, oral bioavailability, changes in transport, metabolism, and so on. In contrast to the amide cases discussed above (A is O), modification to the chemical routes is required for the amines (A is methylene).

Figure 14:
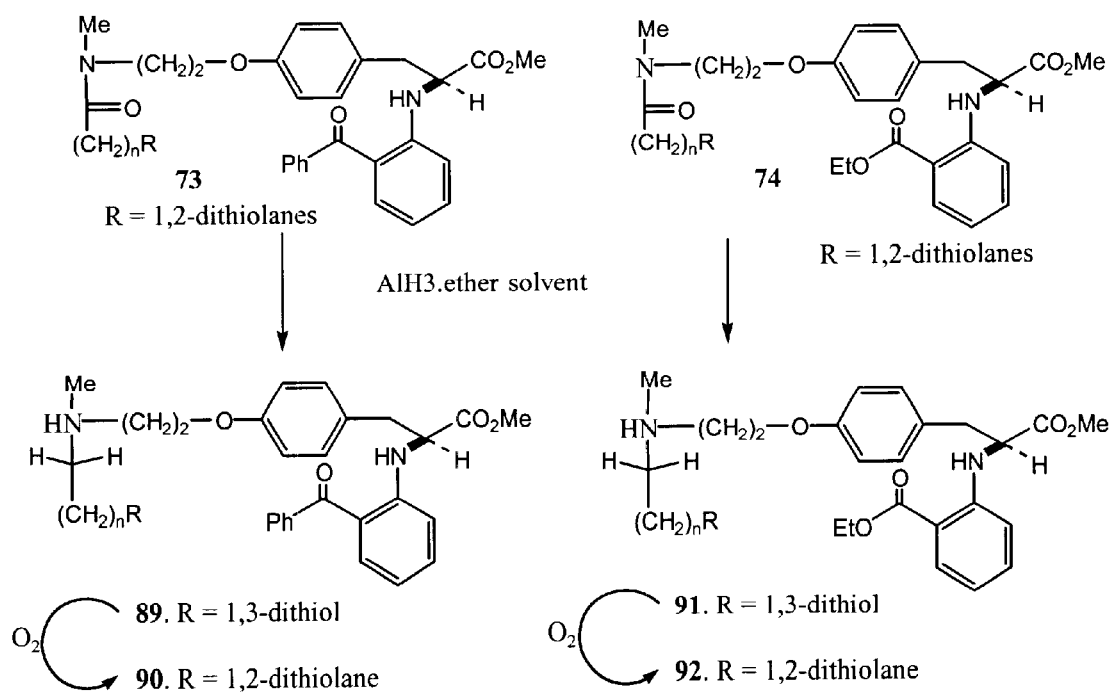
FIG. 14 illustrates a method to synthesize compounds of Formula II of this invention.

As shown in FIG. 14, it is possible to reduce an amide functional group to an amine group with reagents such as $LiAlH_4$. With alane, or $AlH_3$, it is possible to selectively reduce an amide group within systems having other functionality such as esters (see, Martin, S. F., et al., *J Amer. Chem. Soc.*, 109:6124–6134 (1987)). For example, treatment of 73 with alane gives the desired target 90 without reduction of either ketone or ester moieties. The 1,2-dithiolane ring is cleaved to a dithiol 89 initially, and the dithiols can be used as separate products, or can be allowed to undergo facile air oxidation back to the dithiolanes (e.g. 90). This is the general approach to the amine targets (A is methylene) in Formulae I and II, two representative cases being shown in FIG. 14. Alternatively, the dithiols can be acylated by conventional methodology to generate S,S'-diacyldithiols. For example, treatment of 89 with two equivalents of acetic anhydride or acetyl chloride affords the S,S'-diacetate.

In other aspects, it is desirable to carry out the reduction before coupling the side-chain dithiolane-aamine to the propionic acid derivative. If an aminoalcohol such as a N-methylaminoethanol 93 is coupled to any of the lipoic acids 1–24, the resulting alcohols 94 is reduced down to the tertiary amines 96 as shown in FIG. 15.

With the aminoalcohols 96 in hand, coupling to the phenols corresponding to the different structural classes is straightforward. Thus, mesylation of 96 in situ gives 97 and Sn2 reaction of 97 with the sodium phenoxide prepared from 83 and NaH generates adduct 92. The reduced dithiol 91 is then be available by mild reduction with sodium borohydride. Indeed, this scheme is of general utility in preparing the amino-linked compounds; whereas aminoethanol was exemplified in FIG. 15, one can use N-methylaminopropanol to afford compounds of Formulae I and II where n is 3, or N-methylaminobutanol for n is 4.

Figure 15:
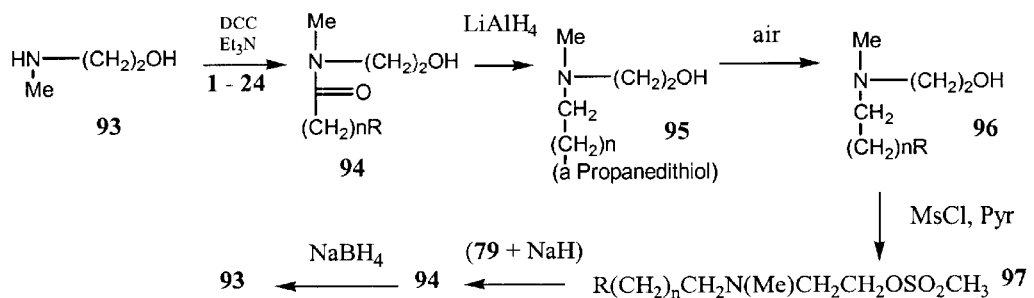
FIG. 15 illustrates a method to synthesize compounds of Formula II of this invention.

In addition to the tyrosine-anthranilate "head group" derived from phenol 83, other phenols are processed in a similar fashion to FIG. 15 to give the amino-linked products. For example, the tyrosine-benzophenone 98 also undergoes coupling, via its sodium salt, with the mesylate 97 to provide 90, as another example of the general class 99.

Figure 16:
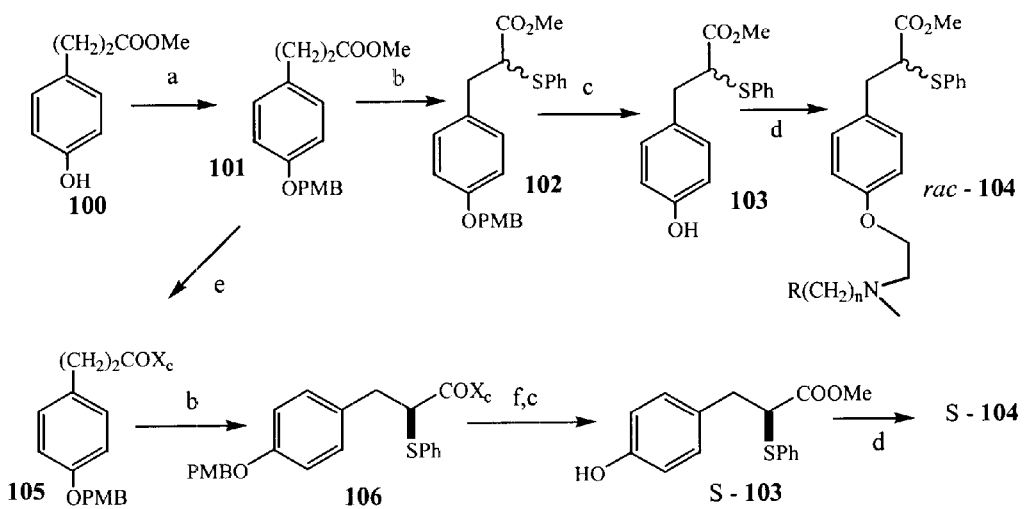
FIG. 16 illustrates a method to synthesize compounds of Formula II of this invention. The key to the reagents is as follows: a) PMB-Br, NaH, DMF; b) LICA, THF; then PhSSPh; c) DDQ; d) NaH, DMF; then 97; e] i) NaOH, aq. MeOH; ii) DCC, Et$_3$N, CH$_2$Cl$_2$; then Prolinol; f) NaOMe, MeOH; alternatively, dil. HCl, then NaHCO$_3$ to furnish carboxylic acid; followed by ether, CH$_2$N$_2$.

Examples of 99 have been given (e.g. 83) involving tethering of a blocked aminoalcohol to the phenolic group. Simple reordering of these schemes allows for the production of all such structures 91 in which X is OR, SR, NHR, and R. This is accomplished by require protection of the phenolic oxygen atom, with deprotection at the appropriate stage as shown in FIG. 16. For example, the dihydrocinnamate 100 is protected as the para-methoxybenzyl ether (PMB) using PMB-Br and NaH to give 101. For the racemate, trap of the enolate with PhSSPh gives 102, needing only to be deprotected en route to alkylation with mesylate 97, furnishing rac-104. As before, chiral 104 is obtained by alkylation of the Prolinol amide derived from 101 (see, FIG. 9).

Thus, exchange of the methyl ester for prolinol amide, 105, is followed by enolate thiophenylation to give 106. Re-exchange of the chiral auxiliary for a methyl ester is possible using methoxide in methanol. Epimerization is accomplished using mild hydrolysis of the prolinol amide with dil. HCl, followed by bicarbonate quench should give an intermediate acid. Careful esterification, such as with diazomethane, restores the ester to provide, after PMB deblocking, S-103. Finally, ether formation gives the target amine S-104. This approach demonstrates how the previous routes can be adapted for installation of the amine side-chain via phenoxide coupling of mesylate 97.

In yet another aspect, the present invention provides compounds of Formula III:

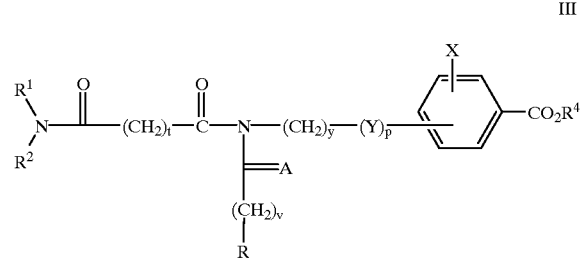

III wherein R, $R^1$, $R^2$, R4, A, X, Y, t, v, y, and p have been defined above.

Figure 17:
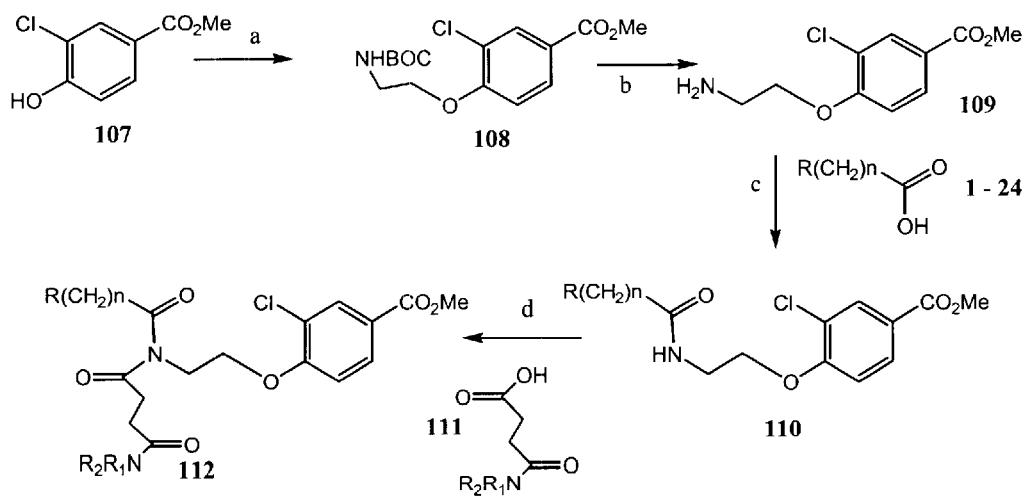
FIG. 17 illustrates a method to synthesize compounds of Formula II of this invention. The key to the reagents is as follows: a) BOCNECH$_2$CH$_2$OMs, NaH; b) HCl, dioxane; c) Et$_3$N, then 1–24, DCC, Et$_3$N, CH$_2$Cl$_2$; d) NaH, oxalyl chloride, DMAP, CH$_2$Cl$_2$.
Figure 18:
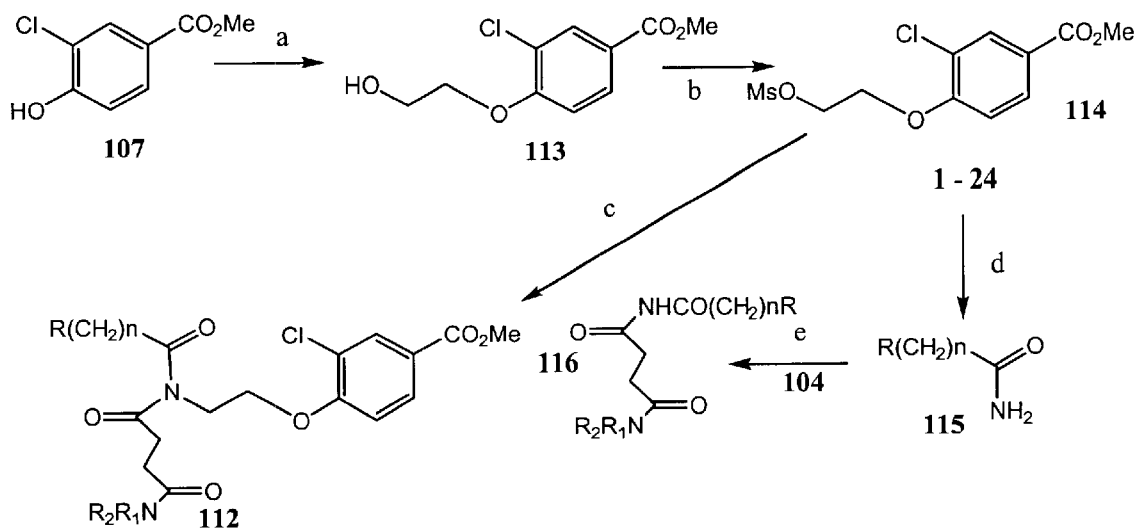
FIG. 18 illustrates a method to synthesize compounds of Formula II of this invention. The key to the reagents is as follows: a) ethylene oxide, NaH; b) MsCl, pyridine; c) 116, KH, DMF, then 114; d) 1–24, DCC, Et$_3$N, CH$_2$Cl$_2$; then dry NH$_3$; e) 104, DCC, Et$_3$N, CH$_2$Cl$_2$.

As shown in FIG. 17, acylation of an appropriate amine 109 is followed by N-acylation of the resulting amide 110, giving the diacylated amine 112. As before, reaction of the mesylate BOCNH(CH$_2$)$_2$OMs with phenoxide from 107 gives 108, which after deprotection with HCl, gives 109. Acylation of amine 109 with lipoic acids 1–24 gives 110 where R is a dithiolanyl moiety. The intermediate 110 is useful compounds in themselves, but second acylation with the succinamide derivative 111 affords adduct 112. Another related approach to FIG. 17 shown in FIG. 18 allows for the alkylation of a mesylate such as 114 with a N,N-diacylamine 116 to access the products 112.

Figure 19:
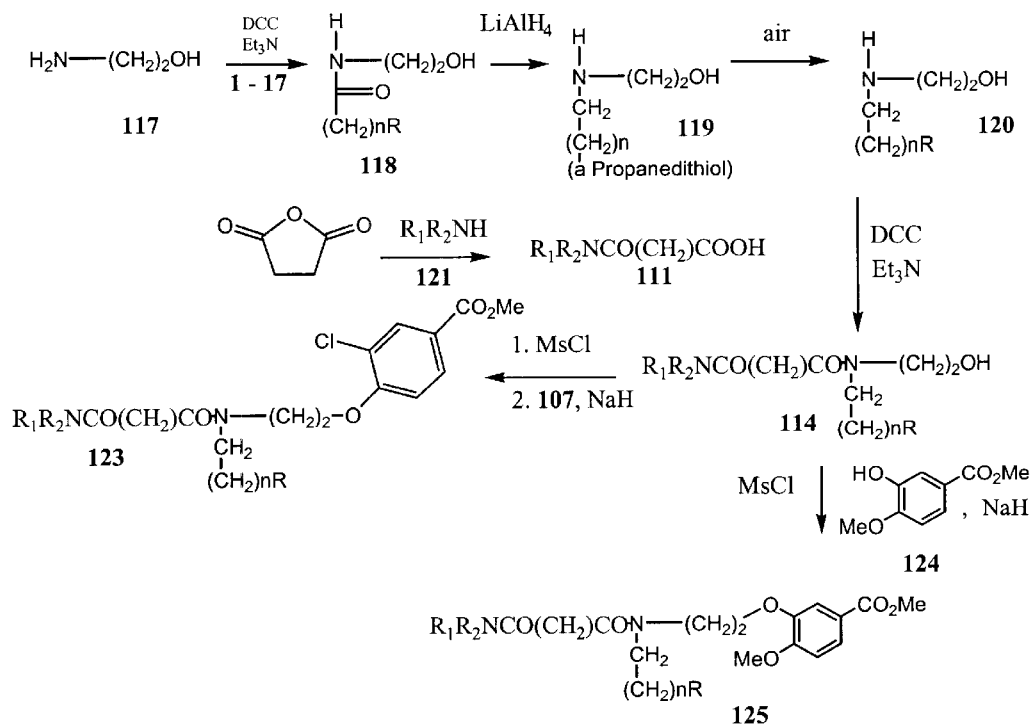
FIG. 19 illustrates a method to synthesize compounds of Formula III of this invention.

As was the true for the syntheses in Formulae I and II, the chemistry for preparation of examples in Formulae III is also adaptable for construction of amino-linked dithiolanes and dithiols as shown in a representative example in FIG. 19. Aminoethanol is coupled with a lipoic acid derivative to give 118, and reduced to the dithiol-aminoalcohols 119. Air oxidation gives the dithiolanes 120, ready for coupling to amide-acids 111, such as that prepared from succinic anhydride and dibenzylamine, 121. Once 111 is activated for coupling, addition of 120 provides the intact side-chain 122. Now, mesylation of 122 as before, and coupling to ap-phenoxybenzoate salt (107) or m—phenoxybenzoate salt (124), gives the requisite products 123 and 125.

Finally, all of the forgoing products such as 123 are reduced to 1,3-dithiols, purified and formulated under inert atmosphere in gel-caps or other suitable technology to maintain the drug in an oxygen free environment prior to administration. Alternatively, the dithiols can be acylated by conventional methodology to generate S,S'-diacyldithiols. For example, treatment of reduced-123 with two equivalents of acetic anhydride or acetyl chloride should afford the S,S'-diacetate.

In still yet another aspect, preferred compound of Formula A relate to a compound of Formula IV:

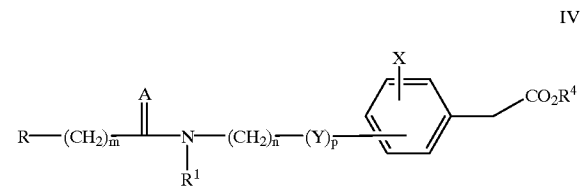

IV wherein R, $R^1$, $R^4$, A, X, Y, m, n, and p have been defined before.

Figure 20:
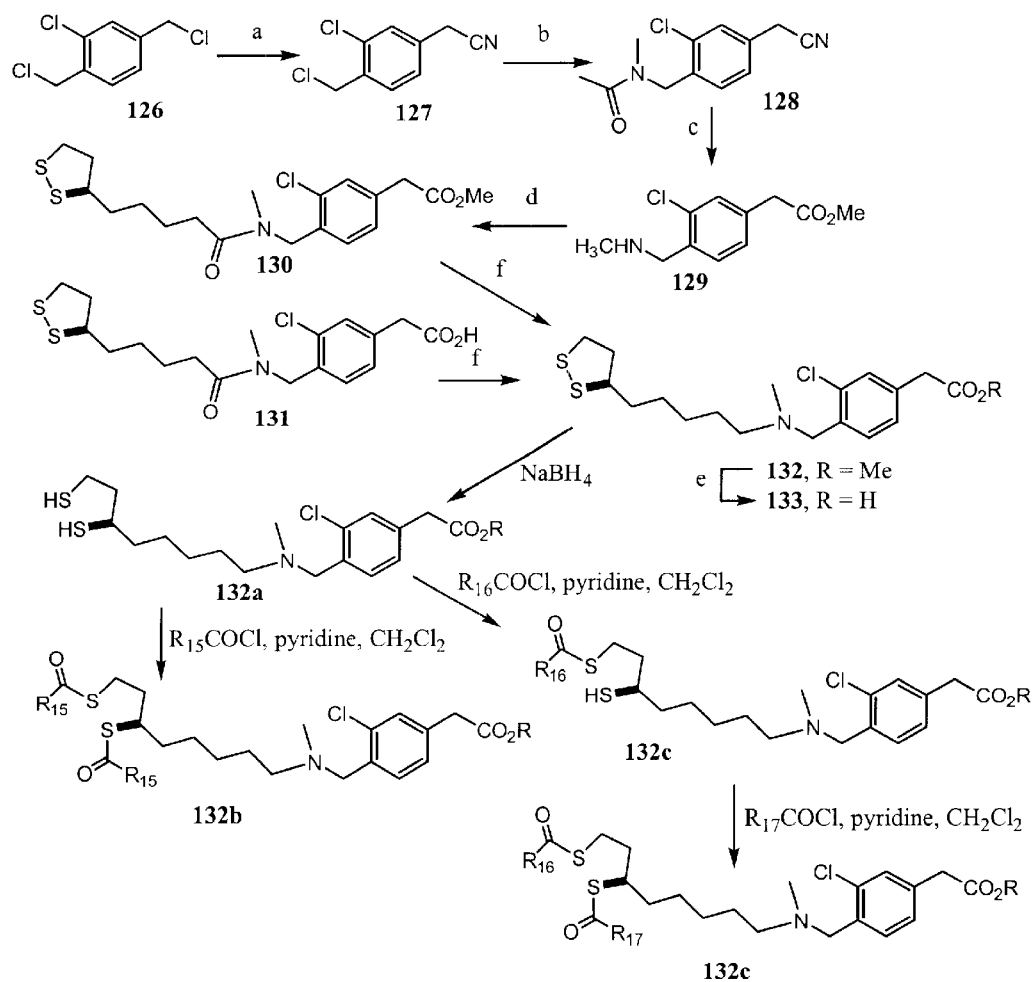
FIG. 20 illustrates a method to synthesize compounds of Formula IV of this invention. The key to the reagents is as follows: a) NaCN, THF; b) MeNHCOCF$_3$, NaH, DMF; c) MeOH, H$_2$SO$_4$ then NaHCO$_3$, MeOH; d) 1–24, DCC, Et$_3$N, CH$_2$Cl$_2$; then 129; e) NaOH, MeOH, HOH; f) (i) N-Methyl lipoamide, NaH, DMF; then 127; (ii) MeOH, H$_2$SO$_4$; g) AlH$_3$, THF.

Compounds of Formula IV relate to arylacetic acids, similar to those reported by Berger et al. (see, Berger, J., et al., *J Biol. Chem.*, 274:6718–6725 (1999)) known to possess PPAR-γ activating properties such as L-796449. The synthesis of a specific example is shown in FIG. 20 (structure 131). In FIG. 20, $R^{15}$ $R^{16}$ $R^{17}$ are each independently selected from the group of hydrogen, optionally substituted alkyl or optionally substituted aryl. Alternatively, the acyl group is an amino acid derivative, an aminoalkyl group, a carboxyalkyl, a carboxyalkyl ester, an aminoarylalkyl, a carboxylarylalkyl and ester. Key intermediates 128 and 129 afford related approaches to attachment of the lipoate moiety; Sn2 displacement of the benzylic chloride with N-trifluoroacetamide anion followed by amide transesterification in methanol provides the amine 129. Simple amide formation via DCC coupling with lipoic acid (rac or R or S) and amine 129 affords the amide 130. The esteramide 130 is a prodrug version of the acid 131, available from ester 120 by simple alkaline hydrolysis. Alternatively, N-methyllipoamide (prepared from lipoic acid, DCC, and excess methylamine) is converted to its anion with NaH and used to displace chloride from 128 to furnish 130 directly.

The amides can be reduced to afford the tertiary amines under mild conditions, without disturbing the ester or acid functionality, with alane. In certain preferred aspects, the tertiary amines 132 and 133 have superior water solubility compared to amides, and can exist as ammonium salts or in the case of 133, as a zwitterionic species. Alternatively, selective reduction of the dithiolane moiety to a dithiol can be followed by acylation by conventional methodology to generate S,S'-diacyldithiols.

In another aspect, preferred compounds of Formula A relate to compounds of Formula V:

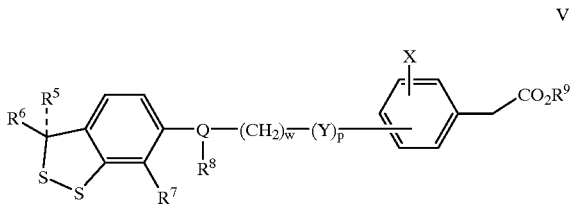

wherein $R^5$, $R^6$, $R^7$, $R^8$, $R^9$, Q, X, Y, w, and p have been described herein.

Figure 21:
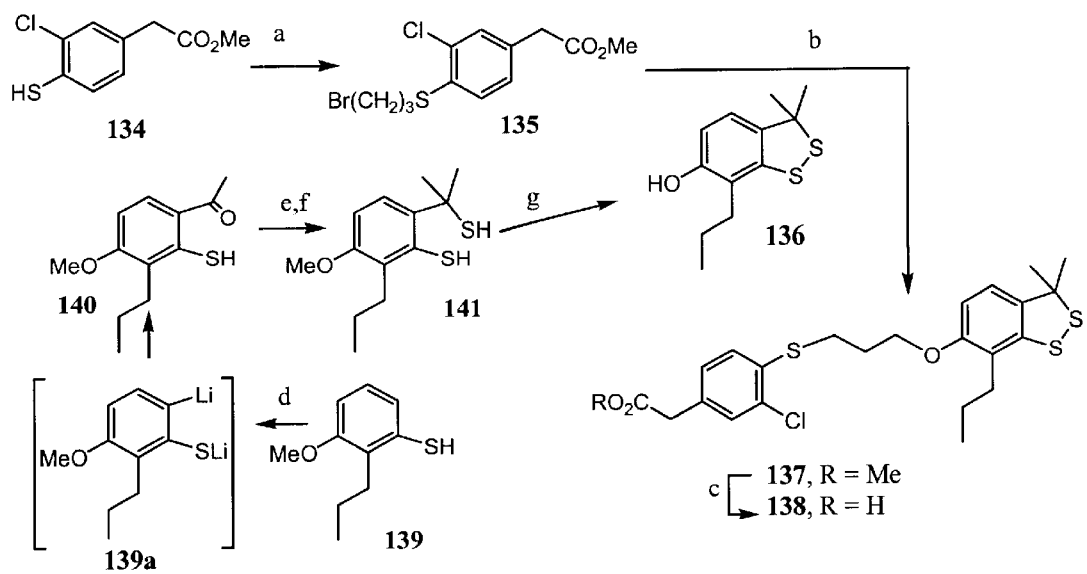
FIG. 21 illustrates a method to synthesize compounds of Formula V of this invention. The key to the reagents is as follows: a) NaH, DMF; then 1,3-dibromopropane; b) 136, NaH; then 135; c) NaOH, MeOH, HOH; d) AcCl, AlCl$_3$, benzene; e) MeMgBr, THF; f) HSH, p-TsA, CH$_2$Cl$_2$; g) PrSK, THF.
Figure 22:
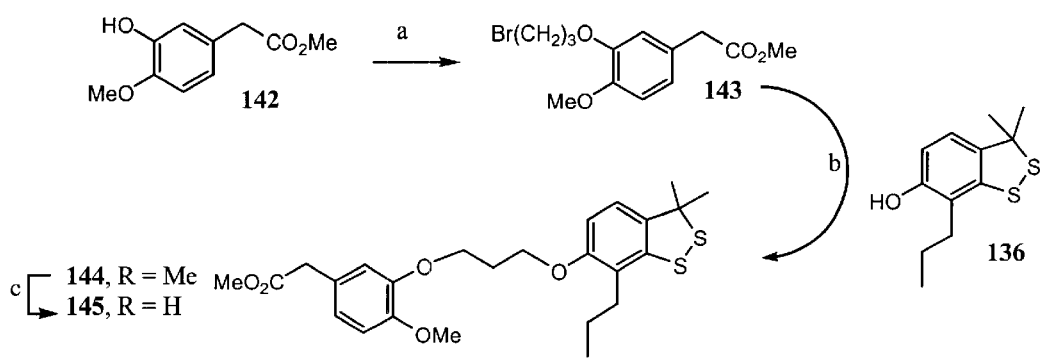
FIG. 22 illustrates a method to synthesize compounds of Formula V of this invention. The key to the reagents is as follows: a) NaH, DMF; then 1,3-dibromopropane; b) 136, NaH; then 135; c) NaOH, MeOH, HOH.

Compounds of Formula V are exemplified by structure 138 wherein R, $R_1$=Me, $R_2$=propyl, $R_3$=naught, $R_4$=H, A=S, n=3, Y=O, p=1, and X=Cl. The synth of example 138 follows in FIG. 21, beginning from the benzenethiol derivative 134. Alkylation of the thiolate anion with excess 1,3-dibromopropane affords the bromopropyl derivative 135. Simple ether formation with the phenoxide anion generated from the phenol 136 then gives the ester 137, hydrolysis of which under alkaline conditions furnishes the target 138. For synthesis of complex benzodithiole 136, acylation of the known resorcinol derivative 139 can be effected adjacent to the free phenol to give ketone 140. Addition of methyl magnesium bromide then gives the phenolic-benzylic diol. Under acidic conditions in the presence of hydrogen sulfide, exchange of the phenol and benzylic alcohol occurs. Finally, O-demethylation is effected with thiolate anion (e.g. propanethiol, KH, HMPA) to afford the phenol 136.

Phenol 142 is treated with excess 1,3-dibromopropane in the presence of NaH to provide 143 Condensation of 143 with 136 provides methyl phenylacetate 144. Hydrolysis of the ester will provide acid 145 a meta oriented target of Formula V.

As an alternative, the process in FIG. 19 is adapted for trapping of the dilithiosulfide 139a with other carbonyl compounds such as benzaldehydes, to give monosubstituted rac-3-aryl-3H-1,2-benzodithioles such as 146.

At the end of the synthesis, selective reduction of the benzodithiole moiety to a dithiol can be followed by acylation by conventional methodology to generate S,S'-diacyldithiols.

As will be apparent to one of skill in the art, certain compounds of the present invention possess asymmetric carbon atoms (optical centers) or double bonds; the racemates, diastereomers, enantiomers, geometric isomers and individual isomers are all intended to be encompassed within the scope of the present invention.

II. CHARACTERIZATION AND PURIFICATION OF THE TARGETS

The synthetic chemistry outlined above can be carried out by standard methods apparent to those skilled in the art, and employ purification of reaction products by chromatography and/or crystallization. Product homogeneity can be ascertained by high performance liquid chromatography. A variety of colunis (normal phase silica gel, reverse phase C-18, etc.) are available, as are computer workstations to analyze the results. Once reaction products are deemed greater than 99.5% HPLC pure, they can be analyzed by elemental analysis, NMR spectroscopy, FTIR, UV and EI or CI mass spectroscopy. Exact mass determinations will be possible and particularly applicable to intermediates. Other physical properties can be determined and recorded such as solubility, melting point, stability, etc. A careful study of chemical stability can be performed and suitable formulation for the oral route of administration can be examined.

III. BIOLOGICAL ASSAY

In certain aspects, compounds of the present invention are activators of PPARγ, PPARα or activators of both PPARγ, PPARα. Using the assay methods of the present invention is possible to distinguish compounds that are PPARγ modulators, PPARa modulators, or compounds which or both PPARγ and PPARα modulators.

As described hereinbelow, a transient cotransfection assay can be used to screen for PPAR activity. In this assay, chimeras are constructed that fuse the ligand binding domains of each PPAR subtype to the DNA binding domain of the yeast transcription factor GAL4. Expression plasmids for the GAL4-PPAR chimeras are then transfected into cells with a reporter construct. This general assay system identifies compounds of Formulae A, I, II, III, IV, and V which are activators of PPARγ and/or PPARα (see, Lehmann et al., *J Biol. Chem.* 270:12953–12956 (1995) and Murakami, K et al., *Biochem. Biophys. Res. Commun.* 260: 609–613 (1999) for specific protocols).

IV. COMPOSITIONS AND METHODS

In another aspect, the present invention provides a pharmaceutical composition comprising a compound of Formulae A, I, II, III, IV, V or mixtures thereof, or a pharmaceutically acceptable salt or solvate thereof, and a pharmaceutically acceptable carrier.

In another aspect, the present invention relates to a method of treating a PPARγ mediated disease or oxidative stress, comprising administering to a subject a therapeutically effective amount of a compound of the of the Formulae A, I, II, III, IV, V and mixtures thereof, thereby treating said PPARγ mediated disease or oxidative stress.

In certain aspects, the compounds, composition and methods of the present invention can be used to treat diseases involving tissues that express PPARγ, PPARα and PPARδ, and more particularly, can be used for treating inflammatory, proliferative, degenerative diseases of multiple organs and tissues, and diseases involving pathological angiogenesis and neovascularization. Advantageously, the compounds can be used for treatment of diseases, tissues and organs regardless of etiological agent. For example, the treatment of corneal injury or ulceration caused by unrelated etiological agents is possible; these include, but are not limited to: 1) foreign body (e.g. contact lens), infectious agent (e.g. candida albicans, chlamydia trachomatis, cytomegalovirus or human immunodeficiency virus), physical agent (e.g. UV radiation), chemical agent (e.g. acids, caustic solvents) chronic systemic disease (e.g. autoimmune or collagen vascular diseases). Methods of the present invention for treating these diseases comprise the administration of an effective amount of any natural or synthetic substance that modifies the activity of PPARγ and/or PPARα.

In one embodiment, the methods of treatment are practiced by administering to a human in need thereof a dose of a compound (or pharmaceutically acceptable salts and solvates thereof in acceptable pharmaceutical excipients) that modifies the activity of PPARγ. The terms "modify and modulate" are defined to include its usually accepted meaning and includes treating a human subject prophylactically to alter inflammation, apoptosis, proliferation, angiogenesis, neovascularization, immune dysfunction, and expression of oncogenes and other genes controlling cell metabolism. The present method includes both medical therapeutic and/or prophylactic treatment, as necessary.

The compounds and methods described herein have clinical utility in the treatment of dermatological diseases (Table I), psychiatric disorders (Table II), neurodegenerative diseases (Table III), diseases associated with allograft transplantation (Table IV), inflammatory or degenerative diseases in multiple organ systems (Table V), neoplastic diseases (Table VIa, Table VIb), diseases caused by naked or coated DNA and RNA viruses (Table VII), diseases associated with human immunodeficiency virus (HIV) infection (Table VIII), inflammatory, proliferative and degenerative diseases of the eye (Tables IXa, IXb, IXc, IXd, IXe), and clinical conditions associated with injury and age-related dysfunctions (Table X).

In certain other aspects, the compound and methods of the present invention are useful in treating diseases including but not limited to, a T lymphocyte-mediated inflammatory disease involving pathological apoptosis, a T lymphocyte-mediated disease such as allograft transplant rejection and complications thereof, an inflammatory disease such as a complication of allograft rejection, a T lymphocyte-mediated disease such as a neurodegenerative inflammatory disease, wherein neurodegenerative inflammatory disease is multiple sclerosis, Alzheimer's disease, or Parkinson's disease. Those of skill in the art will know of other T lymphocyte-mediated diseases and inflammatory diseases suitable for treatment using the present methods and compounds.

In certain aspects, the methods of the present invention are practiced by administering to a mammal a dose of a compound, or a pharmaceutically acceptable salt, ester, solvate or tautomer thereof, a therapeutic amount that activates PPAR$\gamma$ and/or PPAR$\alpha$. The specific diseases and associated disorders that can be treated with the compounds are listed in Tables I through X. Using a method of the invention, therapeutic compounds are typically administered to human patients topically to the skin or mucous membranes, by extra-ocular application, intraocularly (by chemical delivery system or invasive device), or systemically (e.g. sublingually, by suppository, by oral ingestion, intradermally, by inhalation, intramuscularly, intra-articularly, intravenously, or other parenteral route). Parenteral administration by a particular route is used in appropriate circumstances apparent to the practitioner. Oral administration is the preferred route for chronic diseases. Topical administration is the preferred route for dermatological diseases. Extra-ocular application is the preferred route for ocular diseases involving the anterior segment of the eye, or chronic diseases. Preferably, the compositions are administered in unit dosage forms suitable for single administration of precise dosage amounts.

To prepare a topical formulation for the treatment of ophthalmological or dermatological or other disorders described herein, a therapeutically effective concentration of the compound is placed in a dermatological vehicle as is known in the art. The amount of the therapeutic compound to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

The therapeutic compound is optionally administered topically by the use of a transdermal therapeutic system (see, Barry, Dermatological Formulations, p. 181 (1983) and literature cited therein). While such topical delivery systems have been designed largely for transdermal administration of low molecular weight drugs, by definition they are capable of percutaneous delivery. They can be readily adapted to administration of the therapeutic compounds of the invention by appropriate selection of the rate-controlling microporous membrane.

For ophthalmic applications the therapeutic compound is formulated into solutions, suspensions, and ointments appropriate for use in the eye. The concentrations are usually as discussed above for topico-local preparations. For ophthalmic formulations, see Mitra (ed.), Ophthalmic Drug Delivery Systems, Marcel Dekker, Inc., New York, N.Y. (1993) and also Havener, W. H., Ophthalmic Pharmacology, C. V. Mosby Co., St. Louis (1983).

The concentration of the therapeutic compound used depends on the mode of delivery. For topical ophthalmic and extraocular formulations, the concentration of the therapeutic compound is in the range of about 0.01% weight/weight (w/w) to about 10% w/w. Typically, the concentration of the therapeutic compound for this mode of delivery is in the range of about 0.025% w/w to about 2.5% w/w. Solid dispersions of the therapeutic compound as well as solubilized preparations can be used. For intraocular formulations (chemical delivery or delivery by invasive device), the therapeutic compound is delivered at a concentration high enough to achieve a final concentration in the range of about 0.1 $\mu$mol/L to about 10 $\mu$mol/L within the target ophthalmic compartment (e.g. the posterior chamber for the treatment of retinal diseases). Typically, for this mode of delivery, the final concentration of the therapeutic compound is in the range of about 0.25 $\mu$mol/L to about 5 $\mu$mol/L. Solid dispersions of the therapeutic compound as well as solubilized preparations can be used. Thus, the precise concentration is subject to modest but not undue experimental manipulation well within the skill of the ordinary medical practitioner in order to optimize the therapeutic response. Suitable vehicles include oil-in-water or water-in-oil emulsions for preparation of ointments using mineral oils, petrolatum, lanolin, glycerin and the like as well as gels such as hydrogel. A preferred embodiment of the present invention involves administration of semi-solid or solid implants containing PPAR$\gamma$ agonists.

In certain other aspects, the methods of the present invention include the use of all existing synthetic and naturally occurring PPAR$\gamma$ agonists and those yet to be discovered. Preferred PPAR$\gamma$ agonists useful for the application of methods described herein include the novel compounds described in the following submitted patent applications: Pershadsingh HA, Avery MA. 1,2-Dithiolane Derivatives, U.S. patent application Ser. No. 09/520,208), and/or other drugs, which may be in slow release form for topical or systemic delivery. This may be accomplished in a preferred embodiment by using instrumentation and techniques described in U.S. Pat. No. 5,817,075 and U.S. Pat. No. 5,868,728.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound of interest with an inert pharmaceutical diluent and filling the mixture into a hard gelatin capsule of appropriate size. Soft gelatin capsules are prepared by machine encapsulation of a slurry of the compound of interest with an acceptable vegetable oil, light liquid petrolatum or other inert oil. Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill. Usually, the therapeutic compound is prepared in an aqueous solution (discussed below) in a concentration of from about 1 to about 100 mg/ml. More typically, the concentration is from about 10 to 60 mg/ml or about 20 mg/ml. Concentrations below 1 mg/ml may be necessary in some cases depending on the solubility and potency of the compound selected for use. The formulation, which is sterile, is suitable for various topical or parenteral routes including sublingual, by suppository (e.g. per-rectum or vaginal application), oral, intravascular, intradermal, by inhalation, intramuscular, intra-articular, intravenous, or other parenteral route.

In addition to the therapeutic compound, the compositions may include, depending on the formulation and mode of delivery desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or nontoxic, nontherapeutic, nonimmunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives and excipients are those amounts which are effective to obtain a pharmaceutically acceptable formulation in terms of solubility, biological activity, etc.

In certain preferred aspects, a composition of the invention includes a therapeutic compound which may be formulated with conventional, pharmaceutically acceptable, vehicles for topical, oral or parenteral administration. Formulations may also include small amounts of adjuvants such as buffers and preservatives to maintain isotonicity, physiological and pH stability. Means of preparation, formulation and administration are known to those of skill. See generally Remington's Pharmaceutical Science 15th ed., Mack Publishing Co., Easton, Pa. (1980).

Slow Release Delivery

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound. Such slow release systems are applicable to formulations for delivery via topical, intraocular, oral, and parenteral routes.

Delivery by Invasive Device

As mentioned above, delivery intravascularly, intra-articularly, intramuscularly, intra-articularly, intradermally, or other parenteral route can be accomplished by injection, cannula or other invasive device designed to introduce precisely metered amounts of a desired formulation to a particular compartment or tissue. For example, delivery to certain areas within the eye, in situ, can be accomplished by injection, cannula or other invasive device designed to introduce precisely metered amounts directly or contained in a reservoir for slow release in situ, of a desired formulation to a particular compartment or tissue within the eye (e.g. anterior or posterior chamber, uvea or retina). Preferably, a solid or semisolid implant can be delivered subretinally using the instrumentation and methods described in U.S. Pat. Nos. 5,817,075 and 5,868,728.

Routes of Administration

In certain aspects, therapeutic agents of the present invention are delivered or administered topically for treating disorders involving the eye that are listed in Tables I through X. Oral administration is preferred for disorders in Tables I through X that cannot be treated effectively by topical therapy. Additionally, the agents can be delivered parenterally, especially for treatment of retinitis and degenerative retinal diseases, and for other conditions in Tables I through X, that do not respond to oral or topical therapy, or for conditions where oral or topical therapy is not feasible. Parenteral therapy is typically oral, intraocular, transcutaneous, intradermal, intrathecal, intramuscular, intra-articular, by inhalation, intravascular, sublingual, by suppository (e.g. per-rectum or vaginal application), by inhalation, or other parenteral route.

A preferred way to practice the invention for dermatological or ophthalmic disorders in Tables I through XI to which this method is applicable, is to apply the compound of interest, in a cream, lotion, ointment, or oil based carrier, directly to the lesion. Typically, the concentration of therapeutic compound in a cream, lotion, or oil is 0.1 to 2.5%. In general, the preferred route of administration is oral, topical, intraocular or parenteral. Topical administration is preferred in treatment of lesions of the skin as in psoriasis, external eye as in conjunctivitis, keratitis, scleritis, squamous cell carcinoma, corneal erosion, dry eye syndrome, and anterior compartment of the eye as in glaucoma, uveitis and other diseases of the uveal tract, where such direct application is practical and clinically indicated.

Oral administration is a preferred alternative for treatment of other lesions discussed in Tables I through XI, where direct topical application is not useful as in the treatment of chronic or acute systemic diseases, and diseases of the posterior segment of the eye, as in retinitis and other retinal degenerative diseases. Intravascular (intravenous being the preferred route) administration may be necessary in disorders that cannot be effectively treated by topical or oral administration.

Intraocular, transcutaneous, intradermal, intrathecal, intramuscular, intra-articular injections or other invasive technique are preferred alternative in cases where the practitioner wishes to treat one or a few specific areas or lesions depending on their location within the eye. Usually, the compound is delivered in an aqueous solution. Additionally, the therapeutic compounds are injected directly into lesions (intra-lesion administration) in appropriate cases. Intradermal administration is an alternative for extraocular lesions. Intra-lesional and intradermal injections are alternative routes of application for certain lesions, e.g. extraocular neoplastic or hyperplastic lesions such as squamous cell carcinoma and condyloma, respectively. Inhalation therapy is preferred for pulmonary diseases, sublingual and intra-rectal suppository is preferred for rapid delivery or in clinical situations where delivery via the oral or intravascular route is inconvenient or problematic. Application via vaginal topical formulation or via suppository formulation is preferred for diseases localized to the vagina or other segment of the urogenital tract.

For pulmonary applications, a chemical delivery system for drug targeting to lung tissue using the 1,2-dithiolane-3-pentyl moiety of lipoic acid as the "targetor moiety". Therefore a preferred therapeutic compound is the 1,2-dithiolane-3-pentyl ester derivative of any PPARγ or PPARα agonist and is formulated into solutions, suspensions, aerosols and particulate dispersions appropriate for application to the pulmonary system. The therapeutic agent may be inhaled via nebulizer, inhalation capsules, inhalation aerosol, nasal solution, intra-tracheal as a solution via syringe, or endotracheally tube as an aerosol or via as a nebulizer solution. In vitro kinetic and in-vivo pharmacokinetic studies have shown that the 1,2-dithiolane-3-pentyl ester moiety provides an effective pulmonary delivery system which, in a sufficiently stable in buffer and biological media, is hydrolyzed rapidly into the respective active parent drugs, with significantly enhanced delivery and retention of the active compound to lung tissue.

The dithiolane derivatives described in this invention have a wide spectrum of solubility properties, where the oil/water diffusion coefficient (o/w). Calculated o/w values ranged from <1 (very hydrophilic) to >6 (very hydrophobic), depending on the group substituted at the sulfur atoms of the dithiolane ring.

Targeting the Lung and the Central Nervous System: The use of redox chemical delivery systems for targeting drugs to the brain has been described. (Prokai L, et al. *Med Res Rev* 2000; 20:367–416). The 1,2-dithiolane derivatives described herein were designed to be incorporated into liposomal preparations to stabilize the liposomal vector, and for the drugs delivery to tissues such as the skin, the posterior segment of the eye, and for drug delivery across the blood brain barrier and delivery to the central nervous system (CNS), A similar approach has been described for targeting drugs to other organs such as the pulmonary system (Saah M, et al. *J Pharm Sci*. 1996; 85:496–504). Structures with the unmodified dithiolane ring or with the sulfurs as dithiols, were more hydrophobic, and are preferred for targeting the brain and lung. dithiolane dimethyl and diethyl esters are candidates for in corporation into liposomes, resins and reservoirs for targeting the skin. Upon penetrating the alveolar membrane or blood brain barrier, they penetrate cells, are hydrolyzed by esterases and are released to form the dithiolane/dithiol equilibrated redox couple intracellularly. The positively charged amide form of these dithiolane derivatives described in this invention are also considered to be good candidates for delivery to the lung and the CNS.

Targeting the Skin: Structures in which the dithiolane ring is unmodified is a preferred form for transdermal delivery. For example, alpha-lipoic acid applied directly to the skin is readily absorbed and reduced in the epidermis to dihydrolipoate (dithiol), the most potent antioxidant form (Podda M, et al. *Biochem Pharmacol* 1996; 52:627–33). The positively charged amide form of these dithiolane derivatives described in this invention are also considered to be good candidates for delivery to the skin.

Targeting the Gut: Similarly, structures in which the dithiol moieties are derivitized as disuccinates or diglycinates are best suited for delivery across the gastrointestinal mucosa. These compounds are freely water soluble and stable.

Dosage and Schedules

An effective quantity of the compound of interest is employed in treatment. The dosage of compounds used in accordance with the invention varies depending on the compound and the condition being treated. For example, the age, weight, and clinical condition of the recipient patient; and the experience and judgment of the clinician or practitioner administering the therapy are among the factors affecting the selected dosage. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer.

Broadly, for a PPAR ligand (PPARα, PPARγ or PPARδ), the oral dose is determined from the following formula:

oral dose (in mg)=(k1)(EC50)(k2) (LBW)(MW);

wherein k1 is a dimensionless constant of 5 to 100;

EC50 is the concentration (amount) of compound required to activate or bind to 50% of the PPAR ligand in the sample or patient and is in mole/L units;

k2 is the fractional water content of the lean body weight (LBW) of the patient=0.72 L/kg, (see, Geigy Scientific Tables, Vol. 1, Lentner (ed.), p217, Giba-Geigy Ltd., Basle, Switzerland (1981); and MW is the molecular weight of the compound in g/mole.

For example, troglitazone is a compound encompassed by the methods of this invention. A man with diagnosis of early stage prostate cancer in situ has a lean body weight (LBW) of 70 kg. If k1=10; the EC50 for troglitazone=2.4×10 −6 mol/L and the molecular weight of troglitazone=442 g/mol, then the oral dose in milligrams=(10)(2.4×10 −6 mol/L) (0.72 L/kg×70 kg) (442 g/mol) or 535 mg. Similarly, an effective dose of rosiglitazone in milligrams for an average man is (10) (0.06×10–6 mol/L) (0.72L/kg×70 kg) (304 g/mole) or 9.2 mg.

Typically, the dosage per day of a thiazolidinedione of this invention will depend on the affinity of the thiazolidinedione for PPARγ. The dosages of compounds with high affinity, e.g., rosiglitazone, will fall between about 0.5 mg to about 100 mg, of compounds of intermediate affinity will fall from about 10 mg to about 500 g and compounds with low affinity, e.g., troglitazone, will fall from about 100 mg to about 5 g.

An oral dosing schedule is typically, a single dose once a day. However, more than one dose can be given per day. Because of the lower incidence of undesirable side effects, the compounds of this invention can be given until improvement in the inflammatory process or disease involving neovascularization is observed.

Because the compounds of this invention are to some degree fat-soluble, in a preferred embodiment, the compounds are administered with food. The fats in food provide a lipid micellular phase in which the PPARγ and/or PPARα modifiers of this invention can solubilize and be more effectively absorbed.

A dosage range for local treatment is about 0.1 % to about 10% (weight/volume) in a suitable solvent applied that permits release of the compound into the prostate tissue. One of skill will realize that the dosage for local treatment will vary depending on the compound used. For example, the thiazolidinediones of this invention have different affinity for PPARα and/or PPARγ, e.g., pioglitazone has a higher affinity for PPARγ than troglitazone. Typically, the greater the affinity, the more effective the compound, and the lower the dosage that is an effective amount. Therefore, a lower concentration of pioglitazone in a unit dosage form comprises an effective amount.

Typically, the local dosage is administered at least once a day until a therapeutic result is achieved. The dosage can be administered twice a day, but more or less frequent dosing can be recommended by the clinician. Once a therapeutic result is achieved, the compound can be tapered or discontinued. Occasionally, side effects warrant discontinuation of therapy.

An effective quantity of the compound of interest is employed in treatment. The dosage of compounds used in accordance with the invention varies depending on the compound and the condition being treated. The age, lean body weight, total weight, body surface area, and clinical condition of the recipient patient; and the experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

Broadly, an oral dosing schedule is from about 0.1 mg to about 1000 mg once or twice a day depending on the binding affinity of the compound for PPARγ. For example, the typical oral dose of the thiazolidinediones, rosiglitazone and pioglitazone, presently approved for the treatment of type 2 diabetes mellitus, is 4 to 8 mg and 15 mg to 45 mg daily, respectively.

Using troglitazone as the prototype agent for the purpose of this invention, a convenient oral dose for an adult patient is 300 to 600 mg once a day. A dosage range for topical treatment is about 0.5% to about 5% (weight/volume) in a gel, cream or ointment, applied twice a day. A usual dose for intramuscular or intraocular injection is 1 to 10 mg, depending on the compartment of the eye to be treated and on the lean body mass of the patient. A typical dosage for intradermal administration is about 5 to 50 mg per injection per site. A typical dosage for intravenous or intramuscular administration in an adult patient would be between 100 and 400 mg per day given in single or divided doses depending on the judgement of the practitioner.

Typically, the dosage is administered at least once a day until a therapeutic result is achieved. Preferably, the dosage is administered twice a day, but more or less frequent dosing can be recommended by the clinician. Once a therapeutic result is achieved, the drug can be tapered or discontinued. Occasionally, side effects warrant discontinuation of therapy. In general, an effective amount of the compound is that which provides either subjective relief of symptoms or an objectively identifiable improvement as noted by the clinician or other qualified observer.

The compounds in this invention can also be given orally in combination with natural or synthetic compounds that bind to or modify the activity of the vitamin D receptor or in combination with compounds that bind to or modify the activity of the retinoid X receptor to provide for a synergistic effect in the treatment or prevention of the disorders listed in Tables I through XI. Examples of such compounds that provide for synergistic effect when given in combination with the drugs encompassed by the current invention include vitamin D analogs, various retinoic acid derivatives, and other ligands for retinoid X receptors or retinoic acid receptors including but not limited to compounds such as LG100268, tazarotene, TTNPB, AGN 190121, adapalene or LGD1069 (Targretin).

Synergistic therapeutic effects can be achieved by oral or topical administration of the drugs encompassed in the current invention together with orally, topically or intravenously administered drugs that bind to and modify the activity of either the vitamin D receptor, the glucocorticoid receptor, the intracellular enzyme calcineurin, the retinoid X receptors, or the retinoic acid receptors. A preferred dosage range for administration of a retinoic acid derivative or retinoid would typically be from 0.1 to 100 mg per square-meter of body surface area, depending on the drug's ability to bind to or modify the activity of its cognate nuclear receptor, given in single or divided doses, orally or by continuous infusion, two or three times per day. For synergistic therapy, the preferred dosages and routes and frequency of administration of the vitamin D analogs or retinoid compounds can be similar to the dosages and routes and frequency of administration ordinarily recommended for these agents when given without PPARγ activators. Examples of effective retinoids are 9-cis-retinoic acid, 13-cis-retinoic acid, all-trans-retinoic acid (at-RA). Preferred retinoids for this purpose would include 13-cis-retinoic acid, tazarotene, or Targretin. A preferred dosage range for systemic administration of a vitamin D analog would typically be from 0.1 to 100 mg per square-meter of body surface area, depending on the drug's ability to bind to and or activate its cognate vitamin D receptor, given in single or divided doses, orally or by continuous infusion, two or three times per day. Examples of effective vitamin D analogs are 1,25-dihydroxy-vitamin D, calcipotriene, calcipotriol and cholecalciferol. The dosage range and routes and frequency of administration of PPARγactivators required to achieve synergistic effects when given with vitamin D or retinoid derivatives are the same as those described elsewhere in this disclosure. The preferred mode of administration of these drugs for synergistic therapeutic purposes would be orally although alternatively one can use topical or parenteral routes of administration. The dosages and the modes and frequency of administration of the vitamin D or retinoid related compounds for synergistic topical therapy would be similar to those ordinarily recommended for these agents when given without PPARγ activators. The dosage range and the modes and frequency required for topical administration of the flavonoid thiazolidine derivatives given in combination with vitamin D or retinoid related compounds are the same as those described elsewhere in this disclosure.

Synergistic therapeutic effects can be achieved by oral or topical administration of the drugs encompassed in the current invention together with orally, topically or intravenously administered natural or synthetic antioxidants. These include ascorbic acid and its derivatives (e.g. vitamin C), the tocopherols (e.g. vitamin E, vitamin E succinate), carotenes and carotenoids (e.g. beta-carotene), alpha-lipoic acid, probucols, flavones, isoflavones and flavonols (e.g. quercetin, genistein, catechin, apigenin, lutein, luteolin), glutathione and its derivatives (e.g. N-acetylcysteine and dithiothreitol), and phytoestrogens and phenolic anthocyanidin and procyanidin derivatives (e.g. resveratrol, cyanidin, cinnamic acid).

The compounds of the instant invention are further useful to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; and allergies, including asthma. The compounds can also function as neuromodulators in the central nervous system, with useful applications in the treatment of Alzheimer's disease and other forms of dementia, pain (as a spinal analgesic), and headaches. Furthermore, in disorders involving myocardial fibrosis, myocardial ischemia, pathological conditions secondary to the autoimmune response to allograft transplantation, the splanchnic blood flow, including hepatic fibrosis, cirrhosis and oesophagal varices, the compounds of the invention can provide cytoprotection.

Synergistic Activation by PPARγ and PPARα Ligands

In certain aspects, the compounds of the present invention are PPARγ, PPARα or both PPARγ and PPARα activators. Activation of both PPARγ and PPARα have effects on metabolic risk factors that lead to chronic systemic inflammation that can result in diabetes, atherosclerosis, congestive heart failure, ulcerative colitis, rheumatoid arthritis, osteoporosis, Alzheimer's disease, multiple sclerosis, and other degenerative diseases (see, Neve et al. *Biochem Pharmacol*, 60:1245–1250 (2000); McGeer et al. *J Neural Transm Suppl.*, 59:53–7 (2000); Bar-Or et al. *J Neuroimmunol.*, 100:252–9 (1999); Papadakis Targan SR. *Annu Rev Med.*, 51:289–98 (2000)). In certain instances, pharmacological co-activation of both isoforms provides for a synergistic therapeutic effect. One aspect of this invention is the treatment of such diseases that involves the simultaneous pharmacological activation of both PPARγ and PPARα. Synergy may be achieved either with a ligand that co-activates both isoforms, or therapeutic compositions comprising a PPARα agonist and a second compound selected from the group of a PPARγ ligand or a RXR ligand or a PPARγ/RXR ligand. Because the PPARs heterodimerize with RXR, activation of RXR provides the synergistic effect in slowing, arresting, reversing or preventing the disease process.

This aspect of the invention is illustrated in the treatment of atherosclerosis or psoriasis, respectively dermatological and vascular (arterial) manifestations of a diseases with a chronic systemic inflammatory character. The pathogenesis of both atherosclerosis and psoriasis involve the inappropriate proliferation (vascular smooth muscle cells in atherosclerosis and epidermal keratinocytes in psoriasis) and expression of inflammatory cytokines, mediated by activation of the inflammatory transcription factors, NF-kappaB, AP-1 and NFAT (see, Neve et al. *Biochem Pharmacol*, 60:1245–1250 (2000) and Ellis et al. *Arch Dermatol*, 136:609–16 (2000), for discussion). Specific activation of PPARγ on the one hand (see, Ellis et al. *Arch Dermatol*;136:609–16 (2000)), and specific activation of PPARα on the other (see, Komuves, LG et al. *J Invest Dermatol*, 115:353–60 (2000)) have been shown to independently stimulate keratinocyte differentiation and inhibit and epidermal proliferation. Similarly, for example, activation of PPARγ inhibits proliferation of VSM cells, and iNOS production and matrix metalloproteinase (MMP) activity in the vessel wall, whereas activation of PPARα decreases the activity of cell adhesion moles and affects lipoprotein metabolism, resulting in a profound anti-dyslipidemic systemic effect (see, Neve, BP, et al. *Biochem Pharmacol*, 60:1245–1250 (2000)). Thus pharmacological co-activation of PPARγ and PPARα provides synergistic therapy in the treatment of atherosclerosis or psoriasis. Moreover, using the assay methods of the present invention is posssible to distinguish PPARγ modulators, PPARα modulators, or compounds which or both PPARγ and PPARα modulors.

Via negative regulation of NF-kappaB and AP-1 signaling pathways, PPARα inhibits expression of inflammatory genes, such as interleukin-6, cyclooxygenase-2, endothelin-1, and the expression of monocyte-recruiting proteins such as vascular cell adhesion molecule (VCAM)-1, and recruitment of monocytes and foam cells in atherosclerotic lesions. Also via negative regulation of NF-kappaB and AP-1 signaling pathways, PPARgamma activation in macrophages and foam cells inhibits the expression of genes encoding iNOS, MMP-9, scavenger receptor A, VCAM-1. Therefore treatment modalities involving the simultaneous activation of PPARγ and PPARα provides a synergistic therapeutic effect and leads to superior improvement, resolution or prevention of systemic cardiovascular inflammation, including atherosclerosis, vascular restenosis, congestive heart failure and myocardial fibrosis (see, Takano H, et al. *Circ Res*, 87:596–602 (2000); Lee H et al. *Circ Res*, 87:516–21 (2000); Fruchart JC, et al. *Curr Opin Lipidol*, 10:245–57 (1999)).

Phenotypic Targeting of PPARγ and PPARα Activators

In certain instances, both PPARγ and PPARα activators have been shown, independently, to suppress expression of inflammatory regulators, inhibit proliferation and promote apoptosis of pathological cellular phenotypes. Paradoxically and unexpectedly, the opposite case occurs wherein the therapeutic compositions are administered in the treatment of degenerative disease such as multiple sclerosis (a neurodegenerative) or retinopathies and retinitis (neuro-retinal degenerative diseases), in which prevention of apoptosis is the operative mechanism. Therefore, in these disease states, activation of PPARγ and PPARα by suppressing transcription of inflammatory cytokines, prevents apoptosis of the target cell and promotes survival of the non-pathological cellular phenotype. For example, in the case of multiple sclerosis, an autoimmune T lymphocyte-mediated disease, the target cell sustaining the pathological insult is the myelin sheath (oligodendrocyte) in the central nervous system. The pathological cellular phenotypes are amnestic T lymphocytes lacking immune recognition of oligodendrocytes, and inappropriately activated microglia, resulting in inappropriately activation and production of harmful inflammatory cytokines (see, Zhang, GX et al. *Mult Scler*, 6:3–13 (2000)). PPARγ activation can inhibit neuronal apoptosis and promote neuronal protection through the upregulation of neuronal apoptosis inhibitory protein (see, Magun R et al. *Diabetes*, 47:1948–52 (1998)). Indeed, PPARγ activation protects cerebellar granule cells from cytokine-induced apoptotic cell death (Heneka, MT et al. *J Neuroimmunol.*, 100:156–68 (1999)). Moreover, PPARα has been shown to suppress inflammatory cytokines and nuclear factors in monocyte/macrophages. A similar mechanism involving suppression of inflammatory cytokine production by microglia would prevent oligodendrocyte apoptosis. Finally, combined PPARγ and PPARα activation promotes Th1/Th2 differentiation as a final common pathway to inhibit apoptosis of the non-pathological phenotype and promotion of neuronal protection (see, Giorgini, AE et al. *Horm Metab Res*, 31:1–4 (1999); Clark, RB et al. *J Immunol.*, 164:1364–71 (2000)).

Ligand-Specific Control of Gene Expression

In certain embodiments, PPARγ interactions with co-activators and co-repressors tend to be ligand-specific. For example, the natural PPARγ ligand, 15-deoxy-delta-12,14-prostaglandin J2 can induce the receptor-ligand complex to interact with the cofactors: SRC-1, TIF2, AIB-1, p300, TRAP220/DRIP205, whereas, under the same conditions the anti-diabetic thiazolidinedione, troglitazone, a synthetic PPARγ ligand does not. Therefore, ligand binding may alter PPARγ structure in a ligand-type specific way, resulting in distinct PPARγ coactivator interactions (see, Kodera, Y et al. *J Biol Chem. Aug.* 15, 2000)). By analogy, a similar mechanism would provide ligand-specific control of gene expression in the case of PPARα activation.

V. EXAMPLES

Example 1

Synthesis of Compound 32

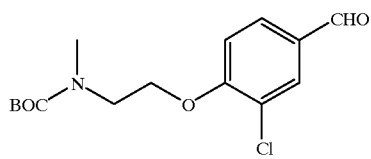

In a 100 ml round-bottomed flask was taken 1 g (5.7 mmol) of 34 in 15 ml of dry methylene chloride and the flask cooled to 0° C. 0.451 g (5.7 mmol) of pyridine was added dropwise followed by 0.65 1 g (5.7 mmol) of methane sulfonylchloride and the mixture stirred at 0° C. for 1 hr. In another round bottomed flask was taken 0.228 g of sodium hydride (pre-washed with anhydrous hexane) in 10 ml Tetrahydrofuran and was cooled to 0° C. 0.89 g (5.7 mmol) of aldehyde 33 was added drop wise and the mixture stirred at this temperature till evolution of hydrogen stopped. The mesylate formed in the first flask was transferred via a cannula into this flask and the combined contents were stirred at room temperature for 5 hrs. Water was added at the end of 5 hrs and the product extracted into ethyl acetate. Concentration of the ethyl acetate layer after drying over sodium sulfate furnished the crude product, which was further purified by column chromatography over silica gel to give 37 in good yield.

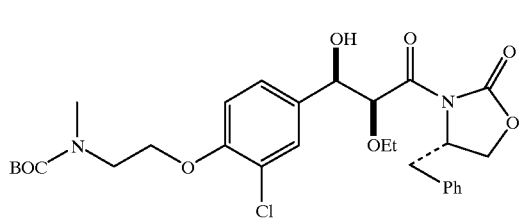

A 50 ml 2-necked flask was charged with 0.420 (1.5 mmol) of 37 in 10 ml dry methylene chloride. The flask was then cooled to 0° C. and at that temperature was added 0.193 g (1.8 mmol) of triethylamine followed by 0.50lg (1.65 mmol) of Bu2BOTf. After stirring for 10 min at this temperature was added 0.5 g (1.5 mmol) of 35 and the mixture was allowed to warm to room temperature and stir for 18 hrs. Water was added and the product was extracted into ether. The ether layer was dried over sodium sulfate and concentrated to afford the crude product, which was further purified by column chromatography over silica gel to provide 39 in moderate yield.

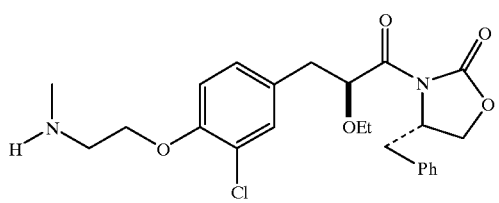

To 0.46 g (0.79 mmol) of 39 in 5 ml of dry methylene chloride was added 0.390 g (3.47 mmol) of trifluoroacetic acid followed by 0.203 g (1.98 mmol) of triethyl silyl hydride and the mixture stirred at room temperature for 4 hrs. 20 ml sat.NaHCO₃ was and the product extracted into ether. The ether layer was successively washed with sat-.NaHCO₃ and brine. The ether layer was dried over sodium sulfate and concentrated to furnish the crude product, which was further purified by column chromatography over silica gel to give 40 in good yield.

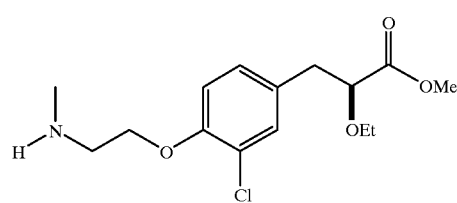

To 0.2 g (0.4 mmol) 40 in 2 ml of methanol was added 0.023 g (0.44 mmol) of sodium methoxide in 2 ml of methanol. The mixture was heated to reflux for 1 hr. The methanol was removed by distillation under aspirator vacuum and the crude product taken up in methylene chloride. The organic layer was dried over sodium sulfate the product further purified over silica gel to furnish the pure amino ester 31.

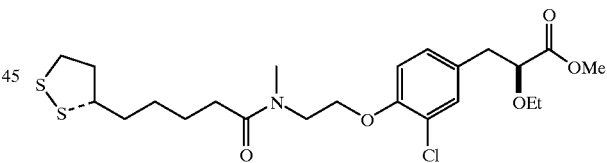

To a solution of 0.110 g (0.35 mmol) of amine 31 and 0.086 g (0.42 mmol) of (+)-lipoic acid in 5 ml dry methylene chloride was added at 0° C., 0.086 g (0.42 mmol) of dicyclohexylcarbodiimide and the mixture stirred for 6 hrs at room temperature. The precipitated urea was filtered off and the methylene chloride concentrated. The product was further purified by column over silica gel to give 32 in excellent yield.

METHODS

Specificities for PPARs

Preferably, the 4-substituted benzodithiolanyl derivatives described in this invention have been designed to bind with high affinity and activate PPARγ. Preferably, the 3-substituted benzodithiolanyl derivatives described in this invention is a modification whereby this compound will bind with high affinity and activate both PPARγ and PPARα (see, Willson et al. *J Med. Chem.*, 43:527–50 (2000)).

A PPARα agonist as specified herein is selected from the group consisting of: a n-3 fatty acid (e.g. alpha-linolenic acid), a n-6 fatty acid (e.g. linoleic acid), conjugated linoleic acid, unconjugated linoleic acid, linolenic acid, palmitic acid, oleic acid, petroselenic acid, erucic acid, lauric acid, eicosapentaenoic acid (EPA) and docosahexaenoic acid (DHA) or 8-(S)-hydroxyeicosatetraenoic acid.

A PPARgamma/RXR ligand (rexinoid) is selected from the group consisting of the retinoids, targretin, LGD 1069 or LG100268 (Ligand Pharmaceuticals), tazarotene, or AGN 4204 (Allergan).

Compounds and their use in Practicing the Invention

Compounds that also apply to the examples given below include rosiglitazone, pioglitazone, KRP 297, MCC 555 and JTT-501. Other compounds relevant to the practice of this invention, including PPARγ, PPARα or PPARγ and PPARα activators are listed in Table 1 in, Willson et al. *J Med. Chem.* 43:527–50 (2000). The activation constants (ED50s) shown in this table may be used to estimate effective doses for administration to humans.

Typical oral doses for some of these compounds are as follows:

Rosiglitazone: 4 mg twice daily

Pioglitazone: 45 mg once daily

KRP 297: 10 mg twice daily

MCC 555: 5 mg twice daily

JTT-501: 10 mg twice daily

Other PPARγ agonists are selected from the group consisting of an alpha-methoxy-beta-phenyl propanoic acid derivative, an N-(2-Benzoylphenyl)-L-tyrosine derivative, a phenylacetic acid derivative or a PPARγ selective cyclopentenone prostaglandin in the A1 or J2 series.

Screening Assays and Cell Systems

In screening for compounds that modify the activity of PPARγ and/or PPARα the following cell systems are employed. Human endothelial cells and vascular smooth muscle (VSM) cells which are known to express both PPARγ and PPARα. Alternatively, isolated human peripheral T lymphocytes from normal healthy donors or a mammalian cell line such as a Jurkat T cell line poorly express PPARalpha and PPARgamma. To test specific PPARgamma activating compounds, lymphocytes or Jurkat cells are transfected with the PPARgamma expression vector. To test mixed PPARalpha and PPARgamma activating compounds, (PPARalpha/PPARgamma co-ligands), lymphocytes or Jurkat cells are transfected with both PPARalpha and PPARgamma expression vectors.

The binding of agonist ligands to the receptor results in changes in the expression level of mRNAs encoded by PPAR target genes. This process, "transactivation", is determined by cell-based assays which monitor this functional activity. Transactivation assays use cells that have been transfected with a vector expressing the receptor as well as a second vector containing a DNA direct repeat (DR-1) response element and a reporter gene, which encodes an enzyme such as chloramphenicol acetyltransferase, secreted placental alkaline phosphatase, or firefly luciferase. Activation of the receptor by agonist ligands leads to induction of reporter enzyme expression, which can be conveniently assayed using standard colorimetric or photometric methods. The procedure used to test the compounds of this invention is the PPAR-GAL4 transactivation assay, which uses chimeric receptors where the PPAR LBD is fused to the DBD of the yeast transcription factor GAL4 and employs a reporter gene containing a GAL4 response element, and has previously been described in detail (Lehmann, J. M. et al. *J Biol. Chem.*, 270, 12953–12956 (1995)). Briefly, cells are incubated with 10% delipidated fetal calf serum and the test compound at the appropriate concentration. After an additional 24 h, cell extracts are prepared and assayed for alkaline phosphatase and beta-galactosidase activity. Alkaline phosphatase activity was corrected for transfection efficiency using the beta-galactosidase activity as an internal standard. Compounds which elicited on average at least 70% activation of PPAR versus rosiglitazone (positive control for PPARgamma specific activation) or versus Wy-14643 (positive control for PPARalpha specific activation) were considered full agonists (Willson, TM, et al. *J Med Chem.*, 43:527–50 (2000); Henke, BR, et al. *J Med Chem.*; 41:5020–36 (1998)).

The scenarios described below employs representative compounds of these classes for screening assays and in examples wherein they are administered to human subjects in the treatment of specified diseases. Compounds of this invention shown in Formula II, e.g. compound 90 or compound 92, are 4-substituted benzodithiolanyl derivatives, are administered to humans at a typical dose of 0.5 to 5 mg once or twice daily, the preferred dose being 2 mg twice daily.

Example 2

Method for Screening for Compounds that Modify the Activity of PPARgamma and PPARalpha Based on Inhibition of NF-kappaB Activation These compounds are tested for the ability to inhibit activity of NF-kappaB. Human endothelial cells and vascular smooth muscle cells (VSMC) are known to express both PPARgamma and PPARalpha (Neve BP et al. *Biochem Pharmacol.*, 60:1245–1250 (2000)). Alternatively, isolated human peripheral T lymphocytes from normal healthy donors or a mammalian cell line such as a Jurkat T cell line transfected with the PPARalpha and/or the PPARgamma expression vector may be used in these experiments. One of these selected cell types is stimulated with a concentration of one or a combination of: phytohemagglutinin/phorbol-12-myristate-13-acetate (PHA/PMA), TNF-alpha, interferon-gamma or some other factor that activates NF-kappaB. Activation of NF-kappaB is determined by electrophoretic mobility shift assay similar to that previously described (Rossi A et al. *Proc Natl Acad Sci USA*, 94:746–50 (1997)). Preincubation of the same cells with 5 micromolar of the test compound 2 hours prior to addition of an activator of NF-kappaB inhibits the activation of NF-kappaB otherwise observed in the absence of the benzodithiolanyl derivative.

Example 3

Method for Screening for Compounds that Modify the Activity of PPARgamma and PPARalpha Based on Inhibition of NFAT Activation Isolated human peripheral T lymphocytes from normal healthy donors or a mammalian cell line such as a Jurkat T cell line transfected with the PPARalpha and/or the PPARgamma expression vector, is stimulated with a concentration of one or a combination of PHA/PMA, TNF-alpha, interferon-gamma or some other factor that activates NFAT. Transcriptional activation of NFAT is determined by electrophoretic mobility shift assay similar to that described by Yang et al. *J Biol Chem.*; 275:4541–4 (2000). Preincubation of the same cells with 5 micromolar of the test compound for 2 hours prior to addition of an activator of NFAT inhibits the activation of NFAT otherwise observed in the absence of said compound.

Example 4

Method for Screening for Compounds that Modify the Activity of PPARgamma and PPARapha Based on Inhibition of IL-2 production Isolated human T lymphocytes or a mammalian cell line such as a Jurkat T cell line transfected with the PPARalpha and/or the PPARgamma expression vector is stimulated with a concentration of one or a combination of PHA/PMA, TNF-alpha, interferon-gamma or some other factor that activates induction of IL-2 gene expression. Production of IL-2 is determined measuring the concentration of IL-2 in the supernatant from cells using Endogen kits (Wolbum), as described by Yang et al. *J Biol Chem.*, 275:4541–4 (2000). Preincubation of the same cells with 5 micromolar of the test compound for 12 hours prior to addition of an activator of IL-2 production inhibits the activation of IL-2 production otherwise observed in the absence of said compound.

Example 5

Methods of Determining the Anti-a poytotic effect of PPARgamma Ligands in PPARalpha or PPARgamma-expressing Cells In human peripheral T lymphocytes from normal healthy donors or a mammalian cell line such as a Jurkat T cell line transfected with the PPARalpha and/or the PPARgamma expression vector, apoptosis (cell death) is induced by adding TNF-alpha (10 ng/ml) and interferon(INF)-gamma (10 ng/ml) (Genzyme, USA). The inhibitory activity of a test compound in preventing this apoptosis is determined by using dexamethasone as the standard, a compound known to have apoptosis inhibitory activity. An aliquot of RPMI-1640 culture medium (containing 10 weight % of fetal bovine serum) is added to each well of a 96-well microplate. Then, a test solution of the candidate compound in dimethylsulfoxide is added to the culture medium to give the desired final concentration (0.1 to 10 micromolar). Subsequently, TNF-alpha (40 ng/ml, final concentration) and INF-gamma (10 ng/ml) are added to the culture medium, and cells incubated for 72 hours at 37 degree C in the presence of 5% carbon dioxide in air. After cultivation, the culture medium is removed from wells by aspiration, and 50 $\mu$l of a 5% (w/v) crystal violet/70% (v/v) methanol solution added to each well to stain living cells. The wells were washed and dried and apoptosis inhibitory activity of the test compound was obtained by determining the optical density by using an absorptiometer [Microplate Reader Model 450, produced by Bio-Rad] at the wavelengths of 570 nm. Dexamethasone standard was compared to the test compound at a final concentration of 1 micromolar.

Example 6

Treatment of a an Optic Neuritis, OR a Retinitis OR a Retinopathy OR a Maculopathy by Oral Administration of Compound 92—A Clinical Trial Early disease: A patient having early ophthalmic manifestations of an optic neuritis (e.g. optic neuritis associated with multiple sclerosis), a retinitis (e.g. retinitis pigmentosa), or a retinopathy (e.g. glaucomatous retinopathy), or a maculopathy (e.g. macular degeneration), is selected for therapy. The patient weighs 70 kilograms, and if female of child-bearing capacity, is given a pregnancy test to confirm that she is not pregnant. Provided that the patient is not pregnant and does not plan to become pregnant during treatment, a compound 92 is administered orally in a dosage of 1 milligram twice daily with a fat-containing meal. The patient is evaluated by an ophthalmologist experienced in the ophthalmic manifestations of retinal diseases at monthly intervals for 3 months. Regression of the disease or improvement in his clinical status is evaluated by monitoring the visual fields, color vision and visual acuity. If regression is not evident or minimal, the dose is increased to 2 mg twice daily. Additionally, a complete blood count, including white cell count and differential, a platelet count, and liver function tests (such as levels of alkaline phosphatase, lactate dehydrogenase, and aminotransferases) are checked prior to treatment and monthly thereafter. The dosage is tapered to a maintenance dose of 1 mg twice daily.

Late disease: A similar patient with late ophthalmic manifestations one of the diseases described, is selected for therapy. The approach is the same as for the foregoing patient, except that the starting dose is 2 mg twice daily. After 12 months at 800 mg, the dose may be decreased to a maintenance dose of 1 mg twice daily.

Example 7

Treatment of an Optic Neuritis, OR a Retinitis, OR a Retinopathy OR a Maculopathy by Oral Administration of Pioielitazone—A Clinical Trial Early disease: A patient having early ophthalmic manifestations of an optic neuritis (e.g. optic neuritis associated with multiple sclerosis), a retinitis (e.g. retinitis pigmentosa), or a retinopathy (e.g. glaucomatous retinopathy), or a maculopathy (e.g. macular degeneration), is selected for therapy. The patient weighs 70 kilograms, and if female of child-bearing capacity, is given a pregnancy test to confirm that she is not pregnant. Provided that the patient is not pregnant and does not plan to become pregnant during treatment, a compound known to activate PPARgamma, namely, the thiazolidinedione, pioglitazone is administered orally in a dosage of 30 milligrams daily. The patient is evaluated by an ophthalmologist experienced in the ophthalmic manifestations of retinal diseases at monthly intervals for 3 months. Regression of the disease or improvement in his clinical status is evaluated by monitoring the visual fields, color vision and visual acuity. If regression is not evident or minimal, the dose is increased to 45 mg daily. Additionally, a complete blood count, white cell count and differential, a platelet count, and liver function tests (such as levels of alkaline phosphatase, lactate dehydrogenase, and aminotransferases) are checked prior to treatment and bimonthly thereafter. After 12 months, the dosage is tapered to a maintenance dose of 30 mg daily.

Late disease: A similar patient with late ophthalmic manifestations one of the diseases described, is selected for therapy. The approach is the same as for the foregoing patient, except that the starting dose is 45 mg twice daily. After 12 months, the dose may be decreased to a maintenance of 30 mg twice daily.

Example 8

An Animal Trial, Therapy for Preventing Acute and Chronic Allograft Rejection A laboratory rat is selected for experimental renal transplantation. An allograft having moderate immunological incompatibility is selected for transplantation. The rat is given compound 92 at a dose of 10 mg/kg daily by gavage for 2 weeks pre-operatively. One kidney is excised and the rat then receives an allograft kidney transplanted from a donor rat of a different strain. Oral therapy with compound 92 is continued post-operatively. One to four weeks later, the rat is sacrificed and the transplanted kidney evaluated histologically for evidence of allograft rejection. The identical experiment is conducted on a control animal given placebo in place of the rosiglitazone or pioglitazone. Histological evidence of rejection is reduced or prevented by treatment with the rosiglitazone or pioglitazone. To monitor the protection from chronic allograft rejection by the test drug, the identical experiment is performed but therapy is continued for 3 to 6 months prior to sacrificing the animals.

Example 9

A Clinical Trial, Therapy for Preventing Acute and Chronic Allograft Rejection A patient who is a candidate for kidney, liver or heart transplantation or other form of organ transplantation is selected for the therapy embodied in this writing. The patient may or may not be receiving other therapies for transplant rejection. A compound that modifies the activity of PPARgamma such as a thiazolidinedione (e.g. rosiglitazone), or compound 92, referred to as the test drug, is orally administered in a dosage effective to achieve suppression of T cell activation as known to those with skill in the art. Therapy is initiated 2 weeks prior to transplantation. Within 24 to 48 hours post-operatively, therapy with the test drug is resumed and the patient is monitored for changes in symptoms and signs consistent with acute (usually occurring within days) or chronic (within 2 to 6 months) rejection, as known to a practitioner skilled in the art of managing post-transplantation allograft rejection/survival. Additionally, a complete blood count, including white cell count and differential, a platelet count, and plasma IL-2 levels, serum creatinine and BUN levels, liver function tests (such as levels of alkaline phosphatase, lactose dehydrogenase, and transaminases), lipid profile, blood glucose, urinary protein and other tests or evaluations known to a practitioner skilled in the art of managing post-transplantation allograft rejection/survival, are checked prior to allograft transplantation, immediately post-operatively (for monitoring acute rejection) and periodically thereafter for the ensuing months, up to 6 months (for monitoring chronic rejection). Administration of the thiazolidinedione or other compound that modifies the activity of PPARgamma or PPARgamma/RXR heterodimers prevents or decreases signs or symptoms of allograft rejection. The administration of the therapy also enables the clinician to decrease the dose of other conventionally used immunosuppressive agents without increasing the risk of allograft rejection. The patient experiences fewer side effects associated with the other conventional immunosuppressive agents.

Example 10

A Clinical Trial, Synergistic (Adjunctive) Therapy for Preventing Acute and Chronic Allograft Rejection The balance between acute rejection and infection after transplantation continues to be of significant clinical concern, especially during the early post-transplantation period. Acute rejection is a significant risk factor for chronic rejection, and chronic rejection is an important cause of late graft loss. Monoclonal antibodies that selectively block the interleukin-2 receptors on activated T-helper cells are used for immunoprophylaxis or anti-lymphocyte globulins for induction therapy to provide reduced dosing of cyclosporine A throughout the early post-transplantation course. In the context of the present invention, a PPARgamma agonist is effective adjunctive therapy for preventing acute and chronic allograft rejection. The PPARgamma agonist is useful for providing reduced dosing of immunosuppressive therapy, including cyclosporine A, tacrolimus, azathioprine, mycophenolate or other related therapy to preventing allograft rejection throughout both early and late phases post-transplantation. The PPARgamma agonist is used with one or more anti-rejection drug, or in combination with a RXR agonist, or a PPARgamma/RXR agonist, and/or a RAR agonist, and/or a vitamin D receptor agonist, and/or a glucocorticoid receptor agonist, and/or an estrogen receptor agonist, and/or an androgen receptor agonist. To achieve a synergistic effect, the treatment can be modified to include combination therapy with a thiazolidinedione (PPARgamma ligand) or rexinoid (e.g. LG100754, a PPARgamma/RXR heterodimer ligand) and another immunosuppressive compound traditionally used for preventing allograft rejection. Examples of such compounds that provide for synergistic effect when given in combination with the drugs encompassed by the current invention include ligands for the glucocorticoid nuclear receptor ligand (e.g. prednisone), inhibitors of purine synthesis (e.g. azathioprine and mycophenolate), and inhibitors of the calcineurin-dependent cytokine synthesis in activated lymphocytes (e.g. cyclosporine, tacrolimus, sirolimus). One or a combination of these compounds are employed (at dosages described above in the section on Dosage and Schedules) in clinical trials similar to the one described above in Examples 5 and 6, or in doses sufficient to prevent or treat allograft rejection. The PPARgamma agonist is selected from the group consisting of: compound 92, 2 mg twice daily; a thiazolidinedione given orally, e.g. rosiglitazone, 4 mg twice daily or pioglitazone, 45 mg once daily). Examples of synergistic combinations are as follows:

a. A PPARgamma agonist is administered in combination with prednisone at an FDA-approved dose.

b. A PPARgamma agonist is administered in combination with prednisone and cyclosporine A or tacrolimus at an FDA-approved dose, or sirolimus at a dose use in clinical trials.

c. A PPARgamma agonist is administered in combination with prednisone and cyclosporine A or tacrolimus or sirolimus, and azathioprine or mycophenolate.

d. A PPARgamma agonist PPARgamma ligand (e.g. an alpha-methoxy-beta-phenyl propanoic acid derivative, an N-(2-Benzoylphenyl)-L-tyrosine derivative, a phenylacetic acid derivative or a PPARgamma-selective cyclopentenone prostaglandin in the A1 or J2 series or prostaglandin-like compound), is administered in combination with one or more FDA-approved immunosuppressive transplant rejection therapeutic compound, as described in examples a, b and c above.

e. A rexinoid PPARgamma/RXR heterodimer ligand (e.g. LG100754) is administered in combination with one or more FDA-approved immunosuppressive transplant rejection therapeutic compound at approved dosages as described in examples a, b and c above.

Example 11

Treatment of Chronic Recalcitrant Multiple Sclerosis by Oral Administration of Pioglitazone— A Clinical Trial The following is an example for treating individuals with chronic recalcitrant multiple sclerosis with an PPARgamma agonists. This method also applies to the treatment of relapsing, remitting multiple sclerosis, to prevent recurrent exacerbations of the disease.

Early disease: The patient presents acutely with the neurological manifestations of multiple sclerosis, and the diagnosis is confirmed by clinical laboratory and pathological diagnostic tests. The patient is evaluated by a neurologist experienced in the clinical and laboratory manifestations of multiple sclerosis lesions. The patient weighs 70 kilograms, and if female of child-bearing capacity, is given a pregnancy test to confirm that she is not pregnant. Provided that the patient is not pregnant and does not plan to become pregnant during treatment, a compound known to activate PPARgamma, namely, the thiazolidinedione, pioglitazone is administered orally in a dosage of 15 milligrams daily during the acute episode, and is titrated up to 30 mg daily then 45 mg daily at weekly intervals. Regression of the disease or improvement in his clinical status is evaluated by monitoring improvement in motor deficits. Reduction of the systemic inflammation associated with the disease is assessed by performing bimonthly measurements of high sensitivity-C-reactive protein (hs-CRP). A reduction in the hs-CRP by 50% within 3 months of initiating therapy is considered to be a positive response to the therapy. Additionally, a complete blood count, white cell count and differential, a platelet count, liver function tests (such as levels of alkaline phosphatase, lactate dehydrogenase, and aminotransferases), erythrocyte sedimentation rate and plasma interleukin-2 levels are checked prior to treatment and monthly thereafter. After 6 months treatment, the dosage is tapered to a maintenance dose of 30 mg.

Late disease: A similar patient with chronic recalcitrant multiple sclerosis, having failed existing approved therapies such as interferon injections, and with late manifestations of the disease, such as weight loss, cachexia, rigidity, vision loss, or quadraplegia, is selected for therapy. The approach is the same as for the foregoing patient, except that the starting dose of 30 mg pioglitazone once daily for 3 months, and is increased to 45 mg thereafter. Regression of the disease or improvement in his clinical status is evaluated by monitoring improvement in motor deficits. A reduction in the hs-CRP by 50% within 3 months of initiating therapy is considered to be a positive response to the therapy.

Example 12

Combination Treatment of a PPAR-Mediated Inflammatory, Proliferative or Degenrative Disease with PPARalpha Agonist and a PPARgamma Agonist—A Clinical Trial The PPAR-mediated disease is selected from one of the following: a degenerative neurological disease (Alzheimer's disease) or a degenerative retinal disease (a retinopathy of any etiology), arthritis (rheumatoid arthritis), atherosclerosis, depression, diabetes mellitus, cardiomyopathy, congestive heart failure, myocardial ischemia, organ fibrosis (hepatic, pulmonary or myocardial), thrombosis, a carcinogenic disease, or other inflammatory, proliferative, or degenerative disease (Horrocks LA and Yeo YK, *Pharmacol Res*, 40:211–25 (1999); Youdim, KA, *Int J Dev Neurosci.*, 18:383–99 (2000); Martinez, M et al. *Rev Neurol*, 28 Suppl 1:S59–64 (1999)).

The PPARalpha ligand is selected from: eicosapentaenoic (EPA, 1 or 2 g twice daily oral dose) and docosahexaenoic (DHA, 1 or 2 g twice daily oral dose) acids. The PPARgamma is selected from: compound 92 (this invention, 1 or 2 mg twice daily oral dose), rosiglitazone (4 mg twice daily oral dose), pioglitazone (30 or 45 mg daily oral dose). These pharmacological compositions may be used to treat acute or chronic disease or may be used prophylactically to prevent the onset of the disease.

The patient presents acutely or chronically with the manifestations of Alzheimer's disease (a neuro-degenerative disease), glaucomatous retinopathy (a neuro-retinal degenerative disease), atherosclerosis (an inflammatory ischemic vascular disease), ulcerative colitis (an inflammatory bowel disease), hepatic fibrosis (a degenerative liver disease), or breast or prostate cancer (a carcinogenic disease). The diagnosis is confirmed by clinical laboratory and pathological diagnostic tests. The patient is evaluated by a specialist experienced in the clinical and laboratory manifestations of the index disease. The patient weighs 70 kilograms, and if female of child-bearing capacity, is given a pregnancy test to confirm that she is not pregnant. Provided that the patient is not pregnant and does not plan to become pregnant during treatment, a compound known to activate PPARgamma, namely, the thiazolidinedione, pioglitazone (Actos, Takeda USA) is administered orally in a dosage of 15 milligrams daily, and is titrated up to 30 mg daily then 45 mg daily at weekly intervals. Regression of the disease or improvement in his clinical status is evaluated by monitoring standard clinical indicators. Additionally, a complete blood count, white cell count and differential, a platelet count, liver function tests (such as levels of alkaline phosphatase, lactate dehydrogenase, and aminotransferases), erythrocyte sedimentation rate and plasma high sensitivity-C-reactive protein are checked prior to treatment and monthly thereafter. After 3 to 6 months treatment, the dosage is tapered to a maintenance dose of 30 mg. The patient's response to therapy is monitored by laboratory markers of the respective disease, and inflammatory markers of systemic inflammation to monitor amelioration of the inflammatory response to assess clinical improvement.

Example 13

Treatment of a PPAR-Mediated Inflammatory, Proliferative or Degenerative Disease with Compound which Activates both PPARalpha and PPARgamma—A Clinical Trial This example is identical to Example 11, except that, instead of administering a compound that activates PPARgamma and another that activates PPARalpha, a single compound that significantly activates, i.e. is a co-ligand for PPARgamma and PPARalpha, is the active ingredient of the pharmacological composition used to treat the inflammatory, proliferative or degenerative disease. Examples of such compounds are the 3-substituted benzodithiolanyl derivatives described in this invention (typical doses are 1 to 10 mg twice daily oral dose, the preferred dose being 2 mg twice daily), or MCC 555 (5 mg twice daily oral dose), or KRP 297 (10 mg twice daily oral dose), or JTT-501 (10 mg twice daily oral dose)

Example 14

Combination Treatment of a PPAR-Mediated Inflammatory, Proliferative or Degenerative Disease with PPARgamma Agonist or a Mixed PPARgamma/PPARalpha Agonist (Co-Ligand) and an Estrogen Receptor Ligand—A Clinical Trial The PPAR-mediated disease is selected from one of the following: a degenerative neurological (Alzheimer's disease) or retinal disease, arthritis, atherosclerosis, depression, diabetes mellitus, cardiomyopathy, congestive heart failure, myocardial infarction, organ fibrosis, thrombosis, a carcinogenic disease, or other inflammatory, proliferative, or degenerative disease (Horrocks, LA and Yeo, YK, *Pharmacol Res.*, 40:211–25 (1999); Youdim, KA, *Int J Dev Neurosci.*, 18:383–99 (2000); Martinez, M et al. *Rev Neurol*, 28 Suppl 1: S59–64 (1999)).

The PPARgamma agonist or mixed PPARgamma/PPARalpha agonist or co-ligand are 4-substituted or 3-substituted benzodithiolanyl derivatives, respectively described in this invention, administered at doses of 1 to 2 mg twice daily oral dose. Examples of other mixed PPARgamma/PPARalpha co-ligands are KRP 297 (50 to 500 mg, daily oral dose. The estrogen receptor (ER) ligand is selected from: estradiol (0.5 to 10 mg, daily oral dose, 1.25 mg preferred), tamoxifen or 4-OH-tamoxifen (5 to 50 mg, daily oral dose, 15 mg preferred), clomifene, coumestrol, genistein (10 to 200 mg, daily oral dose, 50 mg preferred), or biochanin A, a genistein precursor (5 to 100 mg, daily oral dose, 20 mg preferred). These pharmacological compositions may be used to treat acute or chronic disease or may be used prophylactically to prevent the onset of the disease.

The patient presents acutely or chronically with the manifestations of Alzheimer's disease (a neuro-degenerative disease), glaucomatous retinopathy (a neuro- retinal degenerative disease), atherosclerosis (an inflammatory ischemic vascular disease), ulcerative colitis (an inflammatory bowel disease), hepatic fibrosis (a degenerative liver disease), or a carcinogenic disease of the breast or prostate. The diagnosis is confirmed by clinical laboratory and pathological diagnostic tests. The patient is evaluated by a specialist experienced in the clinical and laboratory manifestations of the index disease. The patient weighs 70 kilograms, and if female of child-bearing capacity, is given a pregnancy test to confirm that she is not pregnant. Provided that the patient is not pregnant and does not plan to become pregnant during treatment, KRP 297 is administered orally in a dosage of 100 mg twice daily. Regression of the disease or improvement in his clinical status is evaluated by monitoring standard clinical indicators. Additionally, a complete blood count, white cell count and differential, a platelet count, liver function tests (such as levels of alkaline phosphatase, lactate dehydrogenase, and aminotransferases), erythrocyte sedimentation rate and plasma high sensitivity-C-reactive protein are checked prior to treatment and monthly thereafter. The patient's response to therapy is additionally monitored by laboratory markers of the respective disease, and inflammatory markers of systemic inflammation to monitor amelioration of the inflammatory response to determine clinical improvement.

Example 15

Combination Treatment of a PPAR-Mediated Inflammatory, Proliferative Dermatological (Skin) Disease with PPARgamma Agonist or a Mixed PPARaamma/PPARalpha Agonist (Co-Ligand) and a Vitamin D Receptor Ligand—A Clinical Trial The PPAR-mediated disease is an inflammatory, proliferative or degenerative skin disease such as psoriasis, keratitis, hidradenitis, ichthyosis, acne, rosacea, verrucae and other HPV infections, atopic dermatitis, allergic dermatitis, chemical (irritant) dermatitis, seborrheic dermatitis, solar dermatitis, acute and chronic eczema, seborrheic keratosis, senile keratosis, actinic keratosis, photo-induced keratosis, skin aging, thinning skin, dry skin, wrinkle formation, photo-induced skin aging, keloids, lichen planus.

The PPARgamma agonist or mixed PPARgamma/PPARalpha agonist or co-ligand are 4-substituted (e.g. compound 92) or 3-substituted benzodithiolanyl derivatives, respectively described in this invention, administered at doses of 1 to 2 mg twice daily oral dose, or in a pharmaceutical composition for topical administration, with active ingredient at a concentration ranging from 0.01 to 2.0%, 0.25% preferred. Other PPARgamma specific agonists are selected from the group consisting of: a thiazolidinedione given orally, e.g. rosiglitazone, 4 mg twice daily or pioglitazone, 45 mg once daily). Examples of mixed PPARgamma/PPARalpha co-ligands are KRP 297 (50 to 500 mg, daily oral dose). The vitamin D receptor (VDR) ligand is a natural or synthetic vitamin D derivative. An orally administered vitamin D derivative is selected from: dihydrotachysterol (1 mg daily), 1,25-dihydroxycholecalciferol (1 mcg daily), 25-hydroxycholecalciferol (0.1 mg daily), ergocholecalciferol (1.25 mg daily), and cholecalciferol (1 mg daily). Synthetic vitamin D derivatives are administered topically and is selected from the group consisting of calcipotriene and calcitriol (both at a concentration of 0.005% in an ointment or lotion or shampoo). These pharmacological compositions may be used to treat acute or chronic disease or may be used prophylactically to prevent the onset of the disease.

TABLE I

Examples of dermatological disorders treatable using compounds described in this invention Kertinizing skin diseases, keratitis, hidradenitis, ichthyosis
Psoriasis (all forms, including *p. vulgaris, p. guttata, p. discoidea, p. anthropica, p. universalis*)
Acne (all forms, including *a. vulgaris, a. rosacea, a. inversa*, cystic acne)
Warts, verruca (all forms, including common warts, anogenital (venereal) warts, viral warts including human papilloma virus (HPV) infections, conjunctival warts, oral/buccal warts)
Acute and chronic dermatitides (inflammation of the skin), atopic dermatitis, allergic dermatitis, contact dermatitis, cosmetic dermatitis, chemical dermatitis, seborrheic dermatitis, solar dermatitis, acute and chronic eczema, diaper rash, sunburn
Lupus associated skin lesions
Keratoses such as seborrheic keratosis, senile keratosis, actinic keratosis, photo-induced keratosis, skin aging, thinning skin, dry skin, wrinkle formation, photo-induced skin aging, keratosis *follicularis*
Keloids and prophylaxis against keloid formation
Leukoplakia, *lichen planus*
Urticaria, *pruritus*
Androgenic alopecia in men and women, hirsutism in women

TABLE II

Examples of psychiatric disorders treatable using compounds described in this invention Depression, primary depression or depression secondary to chronic diseases and medications
Dysphoric mood disorders
Obsessive compulsive disorder
Dysthymic disorders
Manic depressive (unipolar or bipolar) disorder

TABLE II-continued

Examples of psychiatric disorders treatable using compounds described in this invention Anxiety states including panic disorder and agoraphobia
Post menstrual syndrome
Schizophrenia
Chronic fatigue syndrome
Substance abuse and drug addiction
Anorexia nervosa and anorexia bullemia

TABLE III

Examples of neurological/neurodegenerative disorders treatable using compounds described in this invention Migraine headaches (e.g. vascular headaches, common migraine)
Primary (e.g. Alzheimer's disease) and secondary (e.g. HIV-related) dementias
Degenerative CNS diseases (e.g. Parkinson's disease, amyotropic lateral sclerosis)
Demyelinating diseases (e.g. multiple sclerosis, Guillain-Barre syndrome)
Pain disorders including algesia, hyperalgesia, acute and chronic pain, allodynia
Primary and secondary encephalitis and encephalomyelitis (e.g. auto-immune encephalomyelitis, allergic encephalomyelitis)
Primary and secondary neuritis, autoimmune neuritis
Other autoimmune diseases (e.g. myesthenia gravis, Eaton-Lambert syndrome)
Congenital and secondary ataxias

TABLE IV

Examples of inflammatory and metabolic disorders associated with allograft transplantation treatable using compounds described in this invention The compounds described herein are useful as monotherapy or adjunctive therapy with existing immunosuppressive agents for the promotion and maintenance of allograft survival, post-transplantation.

Examples of inflammatory and proliferative conditions or diseases associated with allograft transplantation and immune suppression include:
1. Acute allograft rejection
2. Chronic allograft rejection
3. Graft versus host disease
4. Post-transplantation de novo malignancy (e.g. lymphoma and epidermal cancers)
5. Osteoporosis and osteopenia
6. Hyperlipidemia
7. Insulin resistance and diabetes mellitus
8. Hypertension
9. Atherosclerosis
10. Endarteritis associated with heart allograft transplantation
11. Glomerulonephritis associated with renal allograft transplantation
12. Cardiomyopathy and congestive heart failure associated with allograft transplantation, in particular heart transplantation

TABLE V

Examples of diseases of various organ systems treatable using compounds described in this invention

| Organ System | Disease/Pathology |
| --- | --- |
| Cardiovascular | Hypertension, vasculo-occlusive diseases including atherosclerosis, arteritis, endarteritis, endocarditis, myocarditis, arterial plaque (fibrous cap) rupture, thrombosis, restenosis after any invasive vascular procedures; acute coronary syndromes such as unstable angina, myocardial infarction, myocardial ischemia and other ischemic cardiomyopathies, non-ischemic cardiomyopathies, post-myocardial infarction cardiomyopathy and myocardial fibrosis, drug-induced cardiomyopathy. |
| Endocrine | Obesity, type 1 diabetes mellitus, type 2 diabetes mellitus, gestational diabetes, impaired glucose tolerance, Cushing's syndrome (e.g. secondary to chronic glucocorticoid therapy), polycystic ovarian syndrome, osteoporosis, osteopenia, accelerated aging of tissues and organs, e.g. Werner's syndrome. |
| Urogenital | Prostatitis, endometritis, endometriosis, benign prostatic hypertrophy, leiomyoma, polycystic kidney disease (e.g. autosomal dominant PKD), acute tubular necrosis, nephrotic syndrome, diabetic nephropathy, glomerulonephritis |
| Pulmonary | Asthma, chronic obstructive pulmonary disease (COPD), reactive airway disease, pulmonary fibrosis, pulmonary hypertension. |
| Connective tissue | |
| Joint | Rheumatoid arthritis, Raynaud's phenomenon/disease, Sjogren's syndrome, systemic sclerosis, systemic lupus erythematosus, inflammatory bowel disease (ulcerative colitis, Crohn's disease) vasculitides, ankylosing spondylitis, osteoarthritis, reactive arthritis, psoriatic arthritis, fibromyalgia, osteoarthritis, sarcoidosis. |
| Liver/Other | Hepatic fibrosis, hepatic cirrhosis, hepatic steatosis, all etiologies, e.g. alcohol-induced (e.g. ethanol), drug-induced (e.g. tylenol), and toxin-induced (e.g. mushroom poisoning)<br>Fibrocystic breast disease, fibroadenoma |

TABLE VIa

Examples of the neoplastic diseases treatable using compounds described in this invention

| Organ System | Malignancy/Cancer type |
| --- | --- |
| Skin | Basal cell carcinoma, melanoma, squamous cell carcinoma; cutaneous T cell lymphoma; Kaposi's sarcoma. |
| Hematological | Acute leukemia, chronic leukemia and myelodysplastic syndromes. |
| Urogenital | Prostatic, renal and bladder carcinomas, anogenital carcinomas including cervical, ovarian, uterine, vulvar, vaginal, and those associated with human papilloma virus infection. |
| Neurological | Gliomas including glioblastomas, astrocytoma, ependymoma, medulloblastoma, oligodendroma; meningioma, pituitary adenoma, neuroblastoma, craniopharyngioma. |
| Gastrointestinal | Colon, colorectal, gastric, esophageal, mucocutaneous carcinomas. |
| Breast | Breast cancer including estrogen receptor and progesterone receptor positive or negative subtypes, soft tissue tumors. |
| Metastasis | Metastases resulting from all neoplasms. |
| Other | Angiomata, angiogenesis associated with the neoplasms. |

TABLE VIb

Examples of neoplastic diseases treatable using compounds described in this invention (cont'd)

| Location | Malignancy/Cancer type |
| --- | --- |
| Various | fibrosarcoma, myxosarcoma, liposarcoma, chondrosarcoma, osteogenic sarcoma, chordoma, angiosarcoma, enthotheliosarcoma, lymphangiosarcoma, lymphangioendotheliosarcoma, synovioma, mesothelimoa, Ewing's tumor, leiomyosarcoma, rhabdomyosarcoma, colon carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. |

TABLE VII

Examples of viral infections and related pathologies treatable according to the methods of this invention

| Virus | Viral infection/cancer or other virus-associated pathology |
| --- | --- |
| HTLV | T-cell leukemia/lymphoma, HTLV-associated arthritides/myelopathies. |
| HPV | Cervical and anogenital cancers; common and anogenital (venereal) warts, including verrucae, condyloma or condyloma acuminata, related non-neoplastic (e.g., keratitis, conjunctivitis) pre-neoplastic and neoplastic (e.g., conjunctival epithelial neoplasms) diseases of the eye. |
| HAV, HBV, HCV | Hepatitis, hepatocellular carcinoma, lymphoma. |
| CMV | Hepatitis, retinitis, meningitis. |
| HSV, VSV | Related mucocutaneous, oropharyngeal and genital diseases, related skin and respiratory infections, varicella-zoster, chicken pox, herpes zoster, post-herpetic neuralgia, conjunctivitis, keratoconjunctivitis, keratitis. |
| HHV | Exanthem subitum, infectious mononucleosis. |
| EBV | Infectious mononucleosis, chronic fatigue syndrome, lymphoma, conjunctivitis, keratitis, and related infections of the eye. |
| Adenoviruses | Upper and lower respiratory tract infections, pneumonia, conjunctivitis. |
| RSV | Upper and lower respiratory tract infections, pneumonia. |
| PMV | Mumps and related manifestations, e.g., conjunctivitis. |
| MV, RV | Measles, Rubella ("German measles") and related manifestations. |
| Coxsackie viruses | Conjunctivitis, diabetes mellitus, respiratory infections. |
| Influenza viruses | Upper and lower respiratory tract infections, pneumonia. |

HIV, Human Immunodeficiency Virus; HTLV, Human T-cell Lymphocyte Virus; HPV, Human Papilloma Virus; HAV, Hepatitis A Virus; HBV, Hepatitis B Virus; HAV, Hepatitis C Virus; CMV, Cytomegalovirus; HSV, Herpes Simplex Virus (Types I & II); HHV, Human Herpes Virus; EBV, Epstein-Barr Virus; RSV, Respiratory Syncytial Virus; VZV, Varicella-Zoster Virus; PMV, Paramyxovirus; MV, Measles (Rubeola) Virus; RV, Rubella Virus

TABLE VIII

HIV related infections and diseases treatable using compounds described in this invention

| Organ system | Viral infection/manifestation or other HIV-associated disease |
| --- | --- |
| Immunologic | AIDS, primary HIV infection. |
| Dermatological | Anogenital cancers including rectal and cervical cancer, Kaposi's sarcoma, atopic dermatitis, squamous cell carcinoma, hairy leukoplakia, molluscum contagiosum, warts (HPV infections), seborrheic dermatitis, psoriasis, xeroderma, HSV and varicella-zoster |

TABLE VIII-continued

HIV related infections and diseases treatable using compounds described in this invention

| Organ system | Viral infection/manifestation or other HIV-associated disease |
|---|---|
| | infections. |
| Hematologic | Non-Hodgkin's lymphoma, B cell lymphoma, anemia, neutropenia, thrombocytopenia. |
| Gastrointestinal | Anorexia, gastroparesis, diarrhea, malabsorption, gastrointestinal CMV infections, esophagitis, colitis, hepatitis, lymphoma. |
| Ophthalmic | Conjunctivitis, keratitis, keratoconjunctivitis, uveitis, retinitis, chorioretinitis, CMV retinitis, iridocyclitis, vitreitis, choroiditis, papilledema, Kaposi's sarcoma, lymphoma, ocular palsies, conjunctival warts, pre-neoplastic and neoplastic diseases of the eye. |
| Cardiac | Myocarditis, endocarditis, pericarditis. |
| Pulmonary | CMV pneumonitis, lymphoid interstitial pneumonitis. |
| Nephrologic | HIV nephropathy, renal cell carcinoma, amyloidosis, uropathy. |
| Rheumatologic | Arthralgia, fibromyalgia, Reiter's syndrome, psoriatic arthritis, vasculitis. |
| Neurologic | Dementia, viral meningitis, viral encephalitis, HIV encephalopathy, progressive multifocal leukoencephalopathy, CNS lymphoma, peripheral and autonomic neuropathies. |
| Psychiatric | Dysphoric mood disorders, depression, depression associated with chronic diseases and medications, bipolar disorder, anxiety disorders, chronic fatigue syndrome; chronic pain, psychoses, substance abuse disorders and drug addiction. |
| General | Lymphoma, metastatic lymphoma, Kaposi's sarcoma, wasting syndrome, psychosis. |

TABLE IXa

Diseases of the eye treatable using compounds described in this invention
1. Inflammatory eye diseases associated with viral infections

| Disease | Virus |
|---|---|
| Blepharitis | HSV, VZV, Vaccinia, HPV, *molluscum contagiosum* |
| Conjunctivitis | HSV, VZV, BBV, Adenovirus, Vaccinia, Variola, HPV, *molluscum contagiosum*, influenza |
| Follicular c. | Newcastle, measles, mumps, rubella, *molluscum contagiosum* |
| Hemorrhagic c. | Enterovirus, coxsackie |
| Catarrhal c | Rubella |
| Keratitis | HSV, VZV, EBV, Adenovirus, Vaccinia, Variola, HPV, *molluscum contagiosum* |
| Kerato-conjunctivitis | HSV, VZV, EBV, Adenovirus, Vaccinia, Variola, HPV, *molluscum contagiosum* |
| Retinitis | CMV |
| Uveitis | HPV |
| Conjunctival warts | HPV |
| C. epithelial neoplasms | HPV |

2. Ocularplastic diseases

Benign tumors: Keratocanthoma, molluscum contagiosum, dermoid cysts, neurofibroma, neurofibromatosis, schwannoma (neurilemoma), pleiomorphic adenoma Malignant tumors: Basal cell carcinoma, squamous cell carcinoma, mucoepidermoid carcinoma, melanoma, retinoblastoma, embryonal rhabdomyosarcoma, meningioma, adenoid cystic carcinoma, lymphoid tumors of the orbit, mesenchymal tumors (fibrous hystiocytoma) of the orbit, nasopharyngeal carcinoma.

Vascular lesions: Hemangioma, lymphangioma.

TABLE XIb

Ophthalmic diseases treatable using compounds described in this invention (cont'd)

| Disease Category | Examples of Diseases, Causes or Associated Conditions |
|---|---|
| Conjunctivitis | Acute allergic conjunctivitis (e.g. drug-related inflammation, hypersensitivity reactions), chronic (vernal) conjunctivitis, contact lens-associated conjunctivitis, e.g. giant papillary conjunctivitis, conjunctival ulceration, including ulceration associated with mucous membrane, conjunctival warts |
| Blepharitis | Inflammatory etiologies, e.g. blepharitis secondary to rosacea |
| Ophthalmic fibrosis | Steven's-Johnson syndrome with progressive fibrosis and scarring, cicatrization and symblepharon. |
| Corneal injury | Corneal abrasion or ulceration (e.g. contact lens-related injury), or corneal injury of any etiology*. |
| Dry eye syndrome | See Table below |
| Pterygium, pinguecula Pemphigoid | Includes ophthalmic pemhigori |
| Scleritis/Episcleritis | Including glaucoma (primary and secondary etiologies) |
| Iridocyclitis Endophthalmitis Uveal tract diseases | Uveitis, uveoretinitis, panuveitis, all etiologies* |
| Vitreitis, retinitis | e.g. congenital. retinitis, retinitis pigmentosa |
| Infectious retinitis | Viral (e.g. herpes, cytomegalovirus, HIV), tuberculous, syphititic, fungal (e.g. histoplasmosis) |
| Chorioretinopathies | Chorioretinitis, choroiditis, vitreitis, |
| Retinopathies | e.g. Diabetic retinopathy, hypertensive retinopathy |
| Maculopathies | age-related-macular degeneration, white dot syndromes |
| Cataract | Related to diabetes, age, collagen vascular diseases |
| Ocular palsies | |

TABLE XIb-continued

Ophthalmic diseases treatable using compounds described in this invention (cont'd)

Disease Category/Examples of Diseases, Causes or Associated Conditions

*Etiologies of Ophthalmic diseases treatable according to the methods of this invention include diseases induced or caused by physical agents (e.g. UV radiation), chemical agents (e.g. acids, caustic solvents) immunological etiologies (e.g. collagen vascular diseases, auto-immune, T lymphocyte-related), infectious agents such as viruses (HSV, CMV, HIV), mycoplasma, tuberculosis, syphilis, fungae (histoplasmosis)

TABLE IXc

Ophthalmic diseases treatable using compounds described in this invention (cont'd) - Etiologies of dry eye syndrome I. Conditions Characterized by Hypofunction of the Lacrimal Gland:
   A. Congenital
      Familial dysautonomia (Riley-Day syndrome), aplasia of the lacrimal gland (congenital alacrima), trigeminal nerve aplasia, ectodermal dysplasia
   B Acquired
      1. Systemic Diseases, e.g. Sjogren's Syndrome, progressive systemic sclerosis, sarcoidosis, leukemia, lymphyoma, amyloidosis, hemochromatosis,
      2. Infection, e.g. mumps
      3. Injury, e.g. surgical removal of lacrimal gland, irradiation, chemical bum
      4. Medications, e.g. antihistamines, antimuscarinics (atropine, scopolamine), general anesthetics (halothane, nitrous oxide), β-adrenergic blockers (timolol, practolol), neurogenic, neuroparalytic (facial nerve palsy)
II. Conditions Characterized by Mucin Deficiency
   Avitaminosis A, Stevens-Johnson syndrome, ocular pemphigoid; chronic conjunctivitis (e.g. trachoma), chemical bums, drugs and medications
III. Conditions Characterized by Lipid Deficiency
   Lid margin scarring, blepharitis
IV. Defective Spreading of Team Film Caused by the Following:
   A. Eyelid abnormalities
      1. Defects, colboma
      2. Ectropion or entropion
      3. Keratinization of lid margin
      4. Decreased or absent blinking secondary to: neurologic disorders, hyperthyroidism, contact lens, drugs and medications, herpes simplex keratitis, leprosy, conjunctival abnonnalities, pterygium, symblepharon, proptosis

TABLE IXd

Ophthalmic diseases treatable using compounds described in this invention (cont'd) - Non-hereditary and hereditary degenerative diseases

| | |
|---|---|
| Macular disorders: | All etiologies and manifestations, including age-related macular degeneration, exudative macular degeneration, atrophic macular degeneration, crystalline retinopathies, retinal toxicosis of systemic medications, idiopathic central serous choroidiopathy, macular edema |
| Retinovascular diseases and retinopathies: | Retinopathy, vasculo-occlusive r., ischemic r., idiopathic r., hypertensive r., proliferative r., diabetic r., vitreoretinopathy, vasculopathies associated with telangiectasias or aneurysms, retinopathies associated with lupus erythematosus, rheumatoid arthritis, multiple sclerosis, myasthenia gravis, uveoretinitis or diabetes mellitus, glaucomatous retinopathies |
| Glaucoma: | All etiologies and manifestations, including primary and secondary open-angle glaucoma, angle-closure glaucoma, glaucoma associated with intraocular inflammation, elevated intraocular pressure associated with acute glaucoma, steroid-induced glaucoma, glaucoma associated with intraocular hemorrhage, pseudoexfoliative syndrome, glaucomatous optic neuropathy and other degenerative changes (e.g. retinopathy) associated with glaucoma |
| Cataract: | All etiologies and manifestations, including age-related (UV radiation) cataract, cataract associated with systemic diseases such as collagen vascular disease, diabetes mellitus, Wilson's disease |
| Other diseases: | Primary or secondary retinal detachment |

TABLE IXe

Ophthalmic diseases treatable using compounds described in this invention (cont'd) - Congenital degenerative retinopathies 1. Primary pigmented retinopathies, all gene types
   Autosomal dominant retinitis pigmentosa, e.g. rod-cone and cone-rod degenerations Autosomal recessive retinitis pignientosa, e.g. rod-cone and cone-rod degenerations, Lenier's amaurosis congenita
   X-linked recessive pigmented retinopathies, e.g. choroideremia
2. Secondary pigmented retinopathies (retinopathies associated with systemic diseases) Autosomal dominant pigmented retinopathies, e.g. Paget's disease, Charcot-Marie-Tooth, disease, Steinert's disease, Pierre-Marie syndrome
   Autosomal recessive pigmented retinopathies, e.g. diabetes mellitus, mannosidoses, mucopolysccharidoses, Batten's d., Refsum's d., Usher syndrome
   X-linked recessive pigmented retinopathies, e.g. Hunter syndrome

TABLE X

Diseases or conditions treatable using compounds described in this invention

I. Promote healing in the following clinical situations:

Surgical or traumatic wounds to healthy tissues or organs
Wounds caused by chemical or physical agents, e.g. ulcers caused by caustic or erosive chemicals, pressure sores, etc.
Wounds associated with disease states, e.g. diabetic ulcers etc.
Wounds in diseased tissues or organs
II. Promote cell survival and prevent apoptosis in neurodegenerative diseases:

Alzheimer's disease
Parkinson's disease
Amyotrophic lateral sclerosis
Spinal cord injury or transection secondary to trauma or disease
III. Attenuation or arrest of the following conditions or processes:

The natural aging of cells and tissues
Aging induced by chemical or physical agents, e.g. sun-induced skin aging
Accelerated aging associated with diseases, e.g. Wemer's syndrome
IV. Vitalization and revitalization of organs and tissues Promoting cell growth and preventing cell death in the aging process
Promoting therapeutic or non-pathological angiogenesis as a therapeutic approach to treating diseases such as congestive heart failure and cardiomyopathy
Promoting growth of organs and tissues for repair or transplantation All publications, patents and patent publications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

The foregoing is offered primarily for purposes of illustration. It will be readily apparent to those of ordinary skill in the art that the operating conditions, materials, procedural steps and other parameters of the invention described herein may be further modified or substituted in various ways without departing from the spirit and scope of the invention. For example, the invention has been described with human patients as the usual recipient, but veterinary use is also contemplated. Thus, the preceding description of the invention should not be viewed as limiting but as merely exemplary.

What is claimed is:

1. A compound having the formula

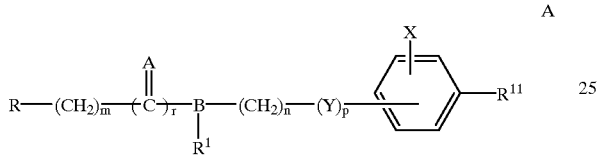

A wherein:

R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

$R^1$ is a member selected from the group consisting of hydrogen, alkyl, arylalkyl and aryl;

$R^{11}$ is a member selected from the group consisting of R, S or racemic—$CH_2(Z)CHCO_2R^{12}$, —$CH_2CO_2R^{12}$, —$CO_2R^{12}$, wherein $R^{12}$ is a member selected from the group consisting of hydrogen, alkyl, arylalkyl and aryl;

A is oxygen or, together with the carbon to which it is bound is a methylene group;

B is a member selected from the group consisting of N, O and S, provided that when B is 0 or S then $R^1$ is absent;

X is a member selected from the group consisting of hydrogen, halogen, $OR^3$, $NH^2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^{12}$, $SO_3$, NH, $NR^{12}$, wherein $R^{12}$ is a member selected form the group consisting of hydrogen, alkyl, arylalkyl and aryl;

Z is a member selected from the group consisting of R S-phenyl, S S-phenyl, racemic S-phenyl, $SCH_3$, $SCH_2CH_3$, O—phenyl, $OCH_3$, $SCH_2CH_3$, propyl, butyl, pentyl, hexyl, benzyl, haloalkyl, $NHR^{13}$, $NR^{13}R^{14}$, wherein $R^{13}$ and $R^{14}$ are each independently a member selected from the group consisting of —(CO) alkyl, optionally substituted —(CO)aryl, optionally substituted —(CO)arylalkyl, optionally substituted —(CO)heteroaryl and —CHO;

m is an integer from 1 to 8 inclusive;

r is 0 or 1;

n is 0, 2, 3, 4; and p is 0 or 1, with the proviso that when n is 0 then Y is not O, S, N, resulting in N-O, N-S, and N-N bonds.

2. A compound according to claim 1, said compound having the formula

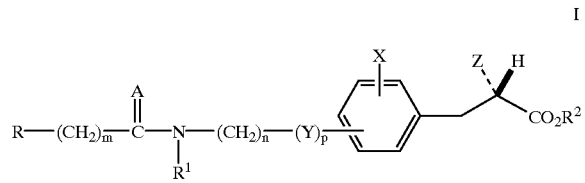

I wherein:

R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

$R^1$ is a member selected from the group consisting of hydrogen, alkyl, arylalkyl and aryl;

$R^2$ is a member selected from the group consisting of hydrogen, alkyl, arylalkyl and aryl;

A is oxygen or, together with the carbon to which it is bound is a methylene group;

X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

Z is a member selected from the group consisting of R S-phenyl, S S-phenyl, racemic S-phenyl, $SCH_3$, $SCH_2CH_3$, O-phenyl, $OCH_3$, $SCH_2CH_3$, propyl, butyl, pentyl, hexyl, benzyl and haloalkyl;

m is an integer from 1 to 8 inclusive;

n is 0, 2, 3, 4; and p is 0 or 1, with the proviso that when n is 0 then Y is not O, S, N, resulting in N—O, N—S, and N—N bonds.

3. The compound according to claim 2, wherein:

R is 1,2-dithiolan-3-yl;

$R^1$ is $(C_1-C_6)$alkyl;

$R^2$ is $(C_1-C_6)$alkyl;

A is oxygen;

X is a member selected from the group consisting of meta-substituted hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of a para-substituted oxygen S, SO, $SO_2$, $SO_2NH$, $SO_2NR^3$, $SO_3$, wherein $R^3$ is a member selected form the group consisting of hydrogen, alkyl, arylalkyl and aryl;

Z is $OCH_2CH_3$;

m is 4;

n is 2; and p is 1.

4. The compound according to claim 3, wherein:

X is a meta-substituted halogen; and

Y is a para-substituted oxygen.

5. The compound according to claim 2, wherein:

R is 1,2-dithiolan-4-yl;

$R^1$ is methyl;

$R^2$ is methyl;

A is oxygen;

X is meta-substituted chlorine;

Y is para-substituted oxygen;

Z is member selected from the group consisting of R S-phenyl, S S-phenyl and racemic S-phenyl, m is 4;

n is 2; and p is 1.

6. A compound according to claim 1, said compound having the formula

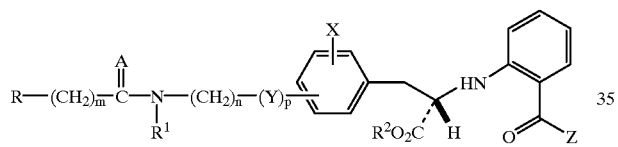

II wherein:

R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

$R^1$ is a member selected from the group consisting of hydrogen, alkyl, arylalkyl and aryl;

$R^2$ is a member selected from the group consisting hydrogen, alkyl, arylalkyl and aryl;

A is oxygen or, together with the carbon to which it is bound is a methylene group;

X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

Z is a member selected from the group consisting of R S-phenyl, S S-phenyl, racemic S-phenyl, $SCH_3$, $SCH_2CH_3$, O-phenyl, $OCH_3$, $SCH_2CH_3$, propyl, butyl, pentyl, hexyl, benzyl and haloalkyl;

m is an integer from 1 to 8 inclusive;

n is 0, 2, 3 or 4; and p is 0 or 1, with the proviso that when n is 0 then Y is not O, S, N, resulting in N—O, N—S, and N-N bonds.

7. The compound according to claim 6, wherein:

R is 1,2-dithiolan-3-yl;

$R^1$ is $(C_1-C_6)$alkyl;

$R^2$ is $(C_1-C_6)$alkyl;

A is oxygen;

X is a member selected from the group consisting of meta-substituted hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of a para-substituted oxygen S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

Z is a member selected from the group consisting of $OCH_2CH_3$ and phenyl;

m is 4;

n is 2; and p is 1.

8. The compound according to claim 7, wherein:

X is a meta-substituted hydrogen; and

Y is a para-substituted oxygen.

9. The compound according to claim 7, wherein:

Z is phenyl.

10. The compound according to claim 6, wherein:

R is 1-(1,3-dithiopropanyl).

11. A compound having the formula

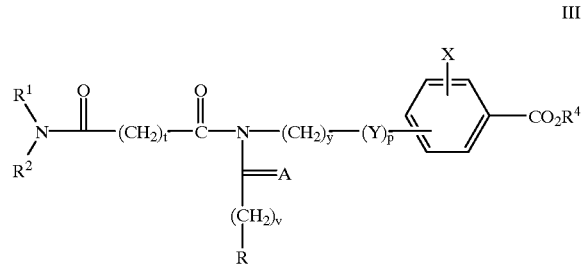

III wherein:

R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

$R^1$ is a member selected from the group consisting of hydrogen, alkyl, arylalkyl and aryl;

$R^2$ is a member selected from the group consisting of hydrogen, alkyl, arylalkyl, and aryl;

$R^4$ is a member selected from the group consisting hydrogen and alkyl;

A is a member selected from the group consisting of oxygen or, together with the carbon to which it is bound is a methylene group;

X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

t is an integer from 1 to 5 inclusive;

v is an integer from 2 to 8 inclusive;

y is an integer from 2 to 4 inclusive; and p is 0 or 1.

12. The compound according to claim 11, wherein:

R is 1,2-dithiolan-3-yl;

$R^1$ is $(C_1–C_6)$alkyl;

$R^2$ is $(C_1–C_6)$alkyl;

$R^4$ is $(C_1–C_6)$alkyl;

A is oxygen;

X is a member selected from the group consisting of meta-substituted hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of a para-substituted oxygen S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

t is 1;

v is 2;

y is 2; and p is 0 or 1.

13. The compound according to claim 12, wherein:

X is a meta-substituted hydrogen; and

Y is a para-substituted oxygen.

14. The compound according to claim 12, wherein:

X is a meta-substituted halogen.

15. The compound according to claim 11, wherein:

R is 1-(1,3-dithiopropanyl).

16. A compound according to claim 1, said compound having the formula

IV

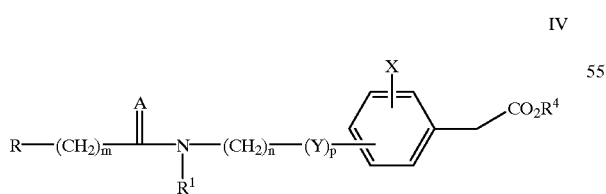

wherein:

R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

$R^1$ is a member selected from the group consisting of hydrogen, alkyl, arylalkyl and aryl;

$R^4$ is a member selected from the group consisting of hydrogen and alkyl;

A is oxygen or together with the carbon to which it is bound is a methylene group;

X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

m is an integer from 1 to 8 inclusive;

n is 0, 2, 3 or 4; and p is 0 or 1, with the proviso that when n is 0 then Y is not O, S, N, resulting in N—O, N—S, and N—N bonds.

17. The compound according to claim 16, wherein:

R is 1,2-dithiolan-3-yl;

$R^1$ is $(C_1–C_6)$alkyl;

$R^4$ is $(C_1–C_6)$alkyl;

A is oxygen;

X is a member selected from the group consisting of meta-substituted hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of a para-substituted oxygen S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

m is 5;

n is 1; and p is 0.

18. The compound according to claim 17, wherein:

X is a meta-substituted hydrogen; and

Y is a para-substituted oxygen.

19. The compound according to claim 16, wherein:

X is a para-substituted hydrogen; and

Y is a meta-substituted oxygen.

20. The compound according to claim 16, wherein:

R is 1,2-dithiolan-3-yl;

R is methyl;

$R^4$ is methyl;

A is oxygen;

X is chlorine m is 5;

n is 1; and p is 0.

21. A compound according to claim 1, said compound having the formula

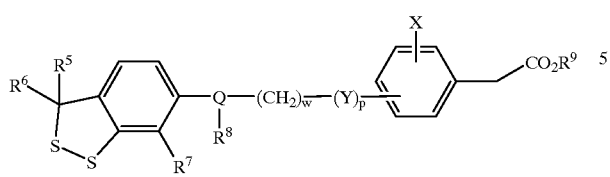

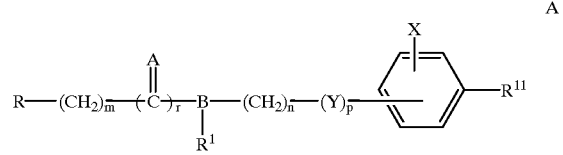

wherein:

- $R^5$ and $R^6$ are each independently a member selected from the group consisting of hydrogen, alkyl, arylalkyl and aryl, and wherein C-3 is either R or S, racemic or achiral;
- $R^7$ is a member selected from the group consisting of hydrogen and alkyl;
- $R^8$ is a member selected from the group consisting of hydrogen and alkyl or is absent;
- or, $R^7$ and $R^8$ and the atoms to which they are bound, join to form a 5-, or 6-membered aryl or heteroaryl ring;
- $R^9$ is a member selected from the group consisting of hydrogen and alkyl;
- Q is a member selected from the group consisting of O, S, NH and $NCH_3$;
- X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;
- Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;
- w is an integer from 2 to 6 inclusive; and
- p is 0 or 1.

22. The compound according to claim 21, wherein:
- $R^5$ and $R^6$ are each alkyl;
- $R^7$ is alkyl;
- $R^9$ is alkyl;
- Q is oxygen;
- X is alkoxy
- Y is oxygen
- w is 3; and
- p is 0 or 1.

23. The compound according to claim 21, wherein:
- $R^5$ is hydrogen;
- $R^6$ is aryl;
- $R^7$ is alkyl;
- $R^9$ is alkyl;
- Q is oxygen;
- X is alkoxy
- Y is oxygen
- w is 3; and
- p is 0 or 1.

24. A pharmaceutical composition comprising a compound having the formula:

wherein:

- R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;
- $R^1$ is a member selected from the group consisting of hydrogen, alkyl, arylalkyl and aryl;
- $R^{11}$ is a member selected from the group consisting of R, S or racemic—$CH_2(Z)CHCO_2R^{12}$, —$CH_2CO_2R^{12}$, —$CO_2 R^{12}$, wherein $R^{12}$ is a member selected from the group consisting of hydrogen, alkyl, arylalkyl and aryl,
- A is oxygen or, together with the carbon to which it is bound is a methylene group;
- B is a member selected from the group consisting of N, O and S, provided that when B is O or S then $R^1$ is absent;
- X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;
- Y is a member selected from the group consisting of oxygen, S, SO, $SO_2$, $SO_2NH$, $SO_2NR^{12}$, $SO_3$, NH, $NR^{12}$, wherein R is a member selected form the group consisting of hydrogen, alkyl, arylalkyl and aryl;
- Z is a member selected from the group consisting of R S-phenyl, S S-phenyl, racemic S-phenyl, $SCH_3$, $SCH_2CH_3$, O-phenyl, $OCH_3$, $SCH_2CH_3$, propyl, butyl, pentyl, hexyl, benzyl, haloalkyl, $NHR^{13}$, $NR^{13}R^{14}$, wherein $R^{13}$ and $R^{14}$ are each independently a member selected from the group consisting of —(CO)alkyl, optionally substituted —(CO)aryl, optionally substituted —(CO)arylalkyl, optionally substituted —(CO)heteroaryl and —CHO;
- m is an integer from 1 to 8 inclusive;
- r is 0 or 1;
- n is 0, 2, 3, 4;
- p is 0 or 1, with the proviso that when n is 0 then Y is not O, S, N, resulting in N—O, N—S, and N—N bonds; and
- a pharmaceutically acceptable carrier therefor.

25. A pharmaceutical composition according to claim 24, said compound having the formula:

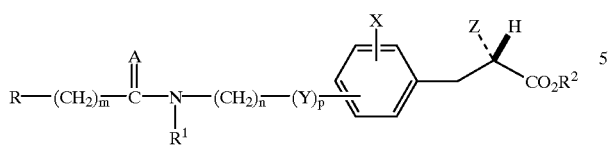

I wherein:
  R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;
  $R^1$ is a member selected from the group consisting of hydrogen, alkyl, arylalkyl and aryl;
  $R^2$ is a member selected from the group consisting of hydrogen, alkyl, arylalkyl and aryl;
  A is oxygen or, together with the carbon to which it is bound is a methylene group;
  X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;
  Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;
  Z is a member selected from the group consisting of R S-phenyl, S S-phenyl, racemic S-phenyl, $SCH_3$, $SCH_2CH_3$, O-phenyl, $OCH_3$, $SCH_2CH_3$, propyl, butyl, pentyl, hexyl, benzyl and haloalkyl;
  m is an integer from 1 to 8 inclusive;
  n is 0, 2, 3, 4; and
  p is 0 or 1, with the proviso that when n is 0 then Y is not O, S, N, resulting in N—O, N—S, and N—N bonds.

26. A pharmaceutical composition according to claim 24, said compound having the formula

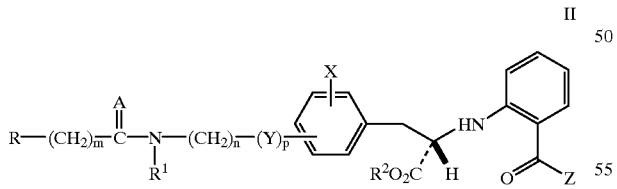

II wherein:
  R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;
  $R^1$ is a member selected from the group consisting of hydrogen, alkyl, arylalkyl and aryl;
  $R^2$ is a member selected from the group consisting of hydrogen, alkyl, arylalkyl and aryl;
  A is oxygen or, together with the carbon to which it is bound is a methylene group;
  X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;
  Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;
  Z is a member selected from the group consisting of R S-phenyl, S S-phenyl, racemic S-phenyl, $SCH_3$, $SCH_2CH_3$, O-phenyl, $OCH_3$, $SCH_2CH_3$, propyl, butyl, pentyl, hexyl, benzyl and haloalkyl;
  m is an integer from 1 to 8 inclusive;
  n is 0, 2, 3 or 4; and
  p is 0 or 1, with the proviso that when n is 0 then Y is not O, S, N, resulting in N—O, N—S, and N—N bonds.

27. A pharmaceutical composition, said composition comprising a compound having the formula

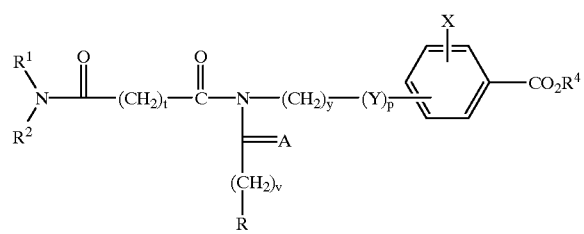

III wherein:
  R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;
  $R^1$ is a member selected from the group consisting of hydrogen, alkyl, arylalkyl and aryl;
  $R^2$ is a member selected from the group consisting of hydrogen, alkyl, arylalkyl, and aryl;
  $R^4$ is a member selected from the group consisting of hydrogen and alkyl;
  A is a member selected from the group consisting of oxygen or, together with the carbon to which it is bound is a methylene group;
  X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;
  Y is a member selected from the group consisting of oxygen, S, SO, $SO_2$, $SO_2NH$, $SO_2NR^3$, $SO_3$, NH, $NR^3$, wherein R³ is a member selected form the group consisting of hydrogen, alkyl, arylalkyl and aryl;

t is an integer from 1 to 5 inclusive;

v is an integer from 2 to 8 inclusive;

y is an integer from 2 to 4 inclusive; and p is 0 or 1.

28. A pharmaceutical composition according to claim 24, said compound having the formula

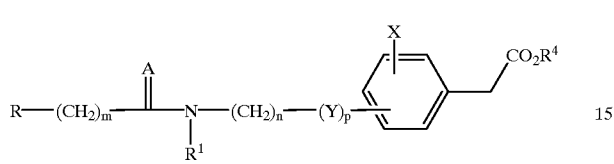

IV wherein:

R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

$R^1$ is a member selected from the group consisting of hydrogen, alkyl, arylalkyl and aryl;

$R^4$ is a member selected from the group consisting of hydrogen and alkyl;

A is oxygen or together with the carbon to which it is bound is a methylene group;

X is a member selected from the group consisting of hydrogen, halogen, OR , $NH_2$, $NHR^3$, $NR^3R^{10}$, $SR^3$, $SOR^3$, $SONH_2$, $SONHR^3$, $SO_2NH^2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

m is an integer from 1 to 8 inclusive;

n is 0, 2, 3 or 4; and p is 0 or 1, with the proviso that when n is 0 then Y is not O, S, N, resulting in N—O, N—S, and N—N bonds, or a pharmaceutical acceptable salt or solvate thereof; and a pharmaceutical acceptable carrier.

29. A pharmaceutical composition according to claim 24, said compound having the formula

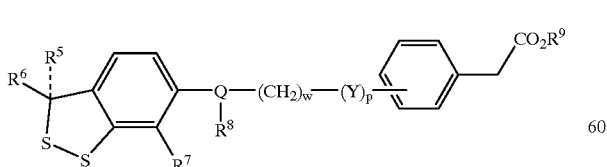

V wherein:

$R^5$ and $R^6$ are each independently a member selected from the group consisting of hydrogen, alkyl, arylalkyl and aryl, wherein C-3 is either R, S, racemic or achiral;

$R^7$ is a member selected from the group consisting of hydrogen and alkyl;

$R^8$ is a member selected from the group consisting of hydrogen and alkyl or is absent;

or, $R^7$ and $R^8$ and the atoms to which they are bound, join to form a 5-, or 6-membered aryl or heteroaryl ring;

$R^9$ is a member selected from the group consisting of hydrogen and alkyl;

Q is a member selected from the group consisting of O, S, NH and $NCH_3$;

X is a member selected from the group consisting of hydrogen, halogen, $OR^3$, $NH_2$, $NHR_3$, $NR^3R^{10}$, $SR^3$, $SOR^3$, $SONH_2$, $SONHR^3$, $SO_2NH^2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

w is an integer from 2 to 6 inclusive; and p is 0 or 1.

30. A method of treating a PPARγ or PPARα mediated disease or oxidative stress, said method comprising administering to a subject a therapeutically effective amount of a compound of the formula

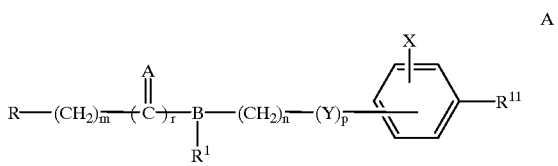

A wherein:

R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

$R^1$ is a member selected from the group consisting of hydrogen, alkyl, arylalkyl and aryl;

$R^{11}$ is a member selected from the group consisting of R, S or racemic—$CH_2(Z)CHCO_2R^{12}$, —$CH_2CO_2R^{12}$, —$CO_2R^{12}$, wherein $R^{12}$ is a member selected from the group consisting of hydrogen, alkyl, arylalkyl and aryl, A is oxygen or, together with the carbon to which it is bound is a methylene group;

B is a member selected from the group consisting of N, O and S, provided that when B is O or S then $R^1$ is absent;

X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^{12}$, $SO_3$, NH, $NR^{12}$, wherein $R^{12}$ is a member selected form the group consisting of hydrogen, alkyl, arylalkyl and aryl;

Z is a member selected from the group consisting of R S-phenyl, S S-phenyl, racemic S-phenyl, SCH$_3$, SCH$_2$CH$_3$, O-phenyl, OCH$_3$, SCH$_2$CH$_3$, propyl, butyl, pentyl, hexyl, benzyl, haloalkyl, NHR$^{13}$, NR$^{13}$R$^{14}$, wherein R$^{13}$ and R$^{14}$ are each independently a member selected from the group consisting of —(CO)alkyl, optionally substituted —(CO)aryl, optionally substituted —(CO)arylalkyl, optionally substituted —(CO)heteroaryl and —CHO;

m is an integer from 1 to 8 inclusive;

r is 0 or 1;

n is 0, 2, 3, 4; and p is 0 or 1, with the proviso that when n is 0 then Y is not O, S, N, resulting in N—O, N—S, and N—N bonds or a pharmaceutical acceptable salt or solvate thereof, thereby treating said PPARγ or PPARα mediated disease or oxidative stress.

31. A method of treating a PPARγ or PPARα mediated disease or oxidative stress according to claim 30, said compound having the formula

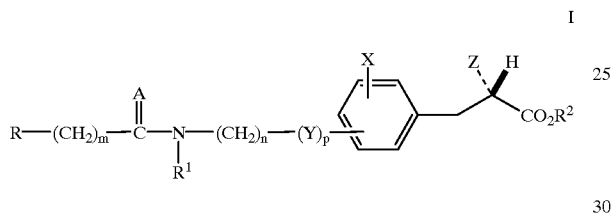

I wherein:

R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

R$^1$ is a member selected from the group consisting of hydrogen, alkyl, arylalkyl and aryl;

R$^2$ is a member selected from the group consisting of hydrogen, alkyl, arylalkyl and aryl;

A is oxygen or, together with the carbon to which it is bound is a methylene group;

X is a member selected from the group consisting of hydrogen, halogen, OR$^3$, NH$_2$, NHR$^3$, NR$^3$R$^{10}$, SR$^3$, SOR$^3$, SONH$_2$, SONHR$^3$, SO$_2$NH$_2$, SO$_2$R$^3$, SO$_2$NHR$^3$ and SO$_3$R$^3$ wherein R$^3$ and R$^{10}$ are each independently a member selected form the group consisting of hydrogen, alkyl, arylalkyl and aryl;

Y is a member selected from the group consisting of oxygen, S, SO, SO$_2$, SO$_2$NH, SO$_2$NR$^3$, SO$_3$, NH, NR$^3$, wherein R$^3$ is a member selected form the group consisting of hydrogen, alkyl, arylalkyl and aryl;

Z is a member selected from the group consisting of R S-phenyl, S S-phenyl, racemic S-phenyl, SCH$_3$, SCH$_2$CH$_3$, O-phenyl, OCH$_3$, SCH$_2$CH$_3$, propyl, butyl, pentyl, hexyl, benzyl and haloalkyl;

m is an integer from 1 to 8 inclusive;

n is 0, 2, 3, 4; and p is 0 or 1, with the proviso that when n is 0 then Y is not O, S, N, resulting in N—O, N—S, and N—N bonds, or a pharmaceutical acceptable salt or solvate thereof, thereby treating said PPARγ or PPARα mediated disease or oxidative stress.

32. A method of treating a PPARγ or PPARα mediated disease or oxidative stress according to claim 30, said compound having the formula

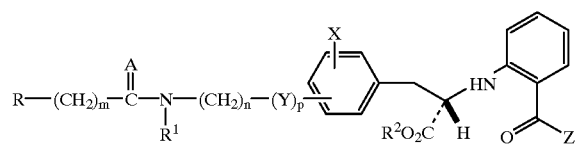

II wherein:

R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

R$^1$ is a member selected from the group consisting of hydrogen, alkyl, arylalkyl and aryl;

R$^2$ is a member selected from the group consisting of hydrogen, alkyl, arylalkyl and aryl;

A is oxygen or, together with the carbon to which it is bound is a methylene group;

X is a member selected from the group consisting of hydrogen, halogen, OR$^3$, NH$_2$, NHR$^3$, NR$^3$R$^{10}$, SR$^3$, SOR$^3$, SONH$_2$, SONHR$^3$, SO$_2$NH$_2$, SO$_2$R$^3$, SO$_2$NHR$^3$ and SO$_3$R$^3$ wherein R$^3$ and R$^{10}$ are each independently a member selected form the group consisting of hydrogen, alkyl, arylalkyl and aryl;

Y is a member selected from the group consisting of oxygen, S, SO, SO$_2$, SO$_2$NH, SO$_2$NR$^3$, SO$_3$, NH, NR$^3$, wherein R$^3$ is a member selected form the group consisting of hydrogen, alkyl, arylalkyl and aryl;

Z is a member selected from the group consisting of R S-phenyl, S S-phenyl, racemic S-phenyl, SCH$_3$, SCH$_2$CH$_3$, O-phenyl, OCH$_3$, SCH$_2$CH$_3$, propyl, butyl, pentyl, hexyl, benzyl and haloalkyl;

m is an integer from 1 to 8 inclusive;

n is 0, 2, 3 or 4; and p is 0 or 1, with the proviso that when n is 0 then Y is not O, S, N, resulting in N—O, N—S, and N—N bonds, or a pharmaceutical acceptable salt or solvate thereof, thereby treating said PPARγ or PPARα mediated disease or oxidative stress.

33. A method of treating a PPARγ or PPARα mediated disease or oxidative stress, said method comprising administering to a subject a therapeutically effective amount of a compound of the formula

III

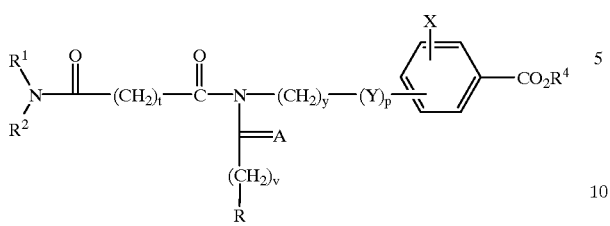

wherein:
R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

$R^1$ is a member selected from the group consisting of hydrogen, alkyl, arylalkyl and aryl;

$R^2$ is a member selected from the group consisting of hydrogen, alkyl, arylalkyl, and aryl;

$R^4$ is a member selected from the group consisting hydrogen and alkyl;

A is a member selected from the group consisting of oxygen or, together with the carbon to which it is bound is a methylene group;

X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

t is an integer from 1 to 5 inclusive;
v is an integer from 2 to 8 inclusive;
y is an integer from 2 to 4 inclusive; and
p is 0 or 1, or a pharmaceutical acceptable salt or solvate thereof, thereby treating said PPARγ or PPARα mediated disease or oxidative stress.

34. A method of treating a PPARγ or PPARα mediated disease or oxidative stress according to claim 30, said compound having the formula

IV

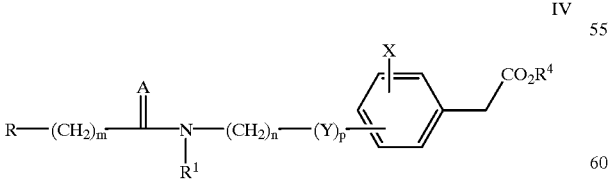

wherein:
R is a member selected from the group consisting of R or S or racemic 1,2-dithiolan-3-yl, or achiral 1,2-dithiolan-4-yl, R or S or racemic 1-(1,3-dithiopropanyl), R or S or racemic S,S'-diacyl-[1-(1,3-dithiopropanyl)], R or S or racemic or achiral 2-(1,3-dithiopropanyl), R or S or racemic or achiral S,S'-diacyl-[2-(1,3-dithiopropanyl)]; and optionally substituted 3R or 3S or racemic 3H-benzo[d]1,2-dithiolen-6-yl;

$R^1$ is a member selected from the group consisting of hydrogen, alkyl, arylalkyl and aryl;

$R^4$ is a member selected from the group consisting of hydrogen and alkyl;

A is oxygen or together with the carbon to which it is bound is a methylene group;

X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^3$, $SO_3$, NH, $NR^3$, wherein $R^3$ is a member selected form the group consisting of hydrogen, alkyl, arylalkyl and aryl;

m is an integer from 1 to 8 inclusive;
n is 0, 2, 3 or 4; and
p is 0 or 1, with the proviso that when n is 0 then Y is not O, S, N, resulting in N—O, N—S, and N—N bonds, or a pharmaceutical acceptable salt or solvate thereof, thereby treating said PPARγ or PPARα mediated disease or oxidative stress, acceptable carrier.

35. A method of treating a PPARγ or PPARα mediated disease or oxidative stress according to claim 30, said compound having the formula:

V

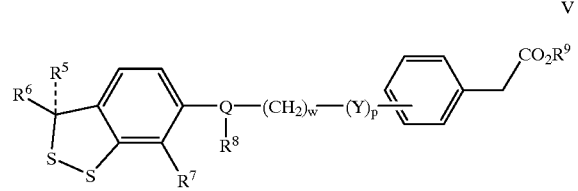

wherein:
$R^5$ and $R^6$ are each independently a member selected from the group consisting of hydrogen, alkyl, arylalkyl and aryl, wherein C-3 is either R, S, racemic or achiral;

$R^7$ is a member selected from the group consisting of hydrogen and alkyl;

$R^8$ is a member selected from the group consisting of hydrogen and alkyl or is absent;

or, $R^7$ and $R^8$ and the atoms to which they are bound, join to form a 5-, or 6-membered aryl or heteroaryl ring;

$R^9$ is a member selected from the group consisting of hydrogen and alkyl;

Q is a member selected from the group consisting of O, S, NH and $NCH_3$;

X is a member selected from the group consisting of hydrogen, halogen, $OR^3$, $NH_2$, $NHR^3$, $NR^3R^{10}$, $SR^3$, $SOR^3$, $SONH_2$, $SONHR^3$, $SO_2NH_2$, $SO_2R^3$, $SO_2NHR^3$ and $SO_3R^3$ wherein $R^3$ and $R^{10}$ are each independently a member selected form the group consisting of hydrogen, alkyl, arylalkyl and aryl;

Y is a member selected from the group consisting of oxygen, S, SO, $SO_2$, $SO_2NH$, $SO_2NR^3$, $SO_3$, NH, $NR^3$, wherein R³ is a member selected form the group consisting of hydrogen, alkyl, arylalkyl and aryl;

w is an integer from 2 to 6 inclusive; and p is 0 or 1, or a pharmaceutical acceptable salt or solvate thereof; and a pharmaceutical acceptable carrier, thereby treating said PPARγ or PPARα mediated disease or oxidative stress.

36. A method for treating an inflammatory and or degenerative disease of mammalian tissues, said method comprising:

administering to a mammal in need thereof a therapeutic amount of a PPARα ligand, and a second agent selected from the group consisting of a PPARγ ligand, an RXR ligand, a PPARγ/RXR ligand and Vitamin D or an analog thereof effective to reverse, slow, stop, or prevent the pathological inflammatory and or degenerative process.

37. The method in accordance with claim 36, wherein the PPARγ ligand is a dithiolane derivative.

38. The method in accordance with claim 37, wherein the PPARγ ligand is a dithiolane derivative, said dithiolane derivative is a member selected from the group consisting of formula A, formula I, formula II, formula III, formula IV, and formula V.

39. The method in accordance with claim 36, wherein said PPARα ligand is a PPARα agonist selected from the group consisting of a saturated or unsaturated fatty acid, an eicosanoid, leukotriene or other arachidonic acid derivative, a fibrate, or a ureido-thioisobutyric acid derivative.

40. The method in accordance with claim 36, wherein said degenerative disease is ophthalmic, confined to the retina and neuro-retina.

41. The method in accordance with claim 40, wherein said disease is a member selected from the group consisting of retinitis, infectious retinitis, uveoretinitis, vitreitis, chorioretinitis, choroiditis, retinitis pigrnentosa optic neuritis, ischemic retinopathy, glaucomatous retinopathy, retinovascular retinopathies, diabetic retinopathy, hypertensive retinopathy, choroidal retinopathy, age-related-macular degeneration, white dot syndromes, and neovascularization of the choroid, retina, subretina and iris.

42. The method in accordance with claim 36, wherein said disease is an inflammatory or degenerative skin disease and includes psoriasis, keratitis, hidradenitis, ichthyosis, acne, rosacea, verrucae and other HPV infections, atopic dermatitis, allergic dermatitis, chemical (irritant) dermatitis, seborrheic dermatitis, solar dermatitis, acute and chronic eczema, seborrheic keratosis, senile keratosis, actinic keratosis, photo-induced keratosis, skin aging, thinning skin, dry skin, wrinkle formation, photo-induced skin aging, keloids, lichen planus.

* * * * *